(12) United States Patent
Wei et al.

(10) Patent No.: US 7,186,716 B2
(45) Date of Patent: Mar. 6, 2007

(54) 3-PYRROL-PYRIDOPYRAZOLES AND 3-PYRROLYL-INDAZOLES AS NOVEL KINASE INHIBITORS

(75) Inventors: Chung Chen Wei, Foster City, CA (US); Ping Huang, Mountain View, CA (US); Yi Xia, Foster City, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 10/638,468

(22) Filed: Aug. 12, 2003

(65) Prior Publication Data

US 2004/0092546 A1 May 13, 2004

Related U.S. Application Data

(60) Provisional application No. 60/445,552, filed on Feb. 6, 2003, provisional application No. 60/406,334, filed on Aug. 28, 2002, provisional application No. 60/402,547, filed on Aug. 12, 2002.

(51) Int. Cl.
*A61K 31/535* (2006.01)

(52) U.S. Cl. .............................. 514/234.2; 514/253.04; 514/303; 544/127; 544/362; 546/119

(58) Field of Classification Search ................ 546/119; 514/303, 234.2, 253.04; 544/127, 362
See application file for complete search history.

(56) References Cited

U.S. PATENT DOCUMENTS

| 6,531,491 B1 | 3/2003 | Kania et al. |
| 6,660,763 B2 | 12/2003 | Tang et al. |
| 2003/0187026 A1 | 10/2003 | Li et al. |
| 2003/0199511 A1 | 10/2003 | Li et al. |

FOREIGN PATENT DOCUMENTS

| DE | 19744027 A1 * | 4/1999 |
| JP | 1190681 | 7/1989 |
| WO | WO 01/02369 A2 | 1/2001 |
| WO | WO 01/47922 A2 | 7/2001 |
| WO | WO 01/53268 A2 | 7/2001 |
| WO | WO 02/083648 A1 | 10/2002 |
| WO | WO 03/000688 A1 | 1/2003 |
| WO | WO 03/014116 A1 | 2/2003 |
| WO | WO 03/024969 A1 | 3/2003 |
| WO | WO 03/051366 A2 | 6/2003 |
| WO | WO 03/068754 A1 | 8/2003 |

OTHER PUBLICATIONS

Ranson, ZD1839 (IressaTM): for more than just non-small cell lung cancer, The Oncologist 2002; 7(suppl 4):16-24.*
Ben-Bassat, inhibitors of tyrosine kinases in the treatment of psoriasis, Current Pharmaceutical Design, 2000, 5, 933-942.*
Poreba et al., "Synthesis and Antiproliferative Activity in Vitro of New Derivatives of 3-Aminopyrazolo[3,4-*b*]pyridine, Part 1. Reaction of 3-Aminopyrazolo[3,4-*b*]pyridine with 1,3- 1,4-Diketones and α,β-Unsaturated Ketones," *Arch. Pharm. Pharm. Med. Chem.*, 2001, pp. 219-223, vol. 334, Wiley-Vch, Germany.
Servi et al., A Novel and Efficient Synthesis of 3-Aryl and 3-Heteroaryl Substituted-1*H*-Indazoles and Their Mannich Derivatives, *Synthetic Communications*, 2002, pp. 3399-3405, vol. 32, No. 22, Marcel Dekker, Inc.

* cited by examiner

*Primary Examiner*—Amelia A. Owens
(74) *Attorney, Agent, or Firm*—Bryan C. Zielinski; Vincent P. Liptak

(57) ABSTRACT

Compounds of Formula I are useful as mediators of protein kinases and have activity as cell proliferation inhibitors:

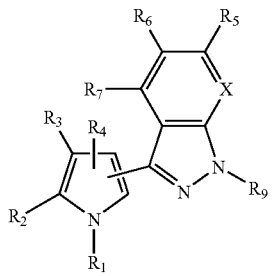

where X, $R_1$–$R_7$ and $R_9$ are as defined herein.

12 Claims, No Drawings

3-PYRROL-PYRIDOPYRAZOLES AND 3-PYRROLYL-INDAZOLES AS NOVEL KINASE INHIBITORS

CROSS-REFERENCE TO RELATED APPLICATIONS

This application claims the benefit under 35 U.S.C. § 119(e) of U.S. Provisional Application Ser. No. 60/402,547, filed Aug. 12, 2002; U.S. Provisional Application Ser. No. 60/406,334, filed Aug. 28, 2002; and U.S. Provisional Application Ser. No. 60/445,552, filed Feb. 6, 2003, the disclosure of which applications is incorporated herein by reference in their entirety.

BACKGROUND OF THE INVENTION

The following is offered as background information only and is not admitted to be prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently broken down into two classes, the protein tyrosine kinases (PTKs) and the serine-threonine kinases (STKs).

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes. At present there are four groups of STK's; Ste (sterile 20, sterile 11 and sterile 7); camk (calmodulin regulated kinases and related kinases); AGC (protein kinase A, protein kinase G and protein kinase C) and CMGC (cdk, map kinase, glycogen synthetase kinase and clk). The sterile 20 kinases inlcude PAK and CZ.

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, Neuron 9:303–391 (1992), which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated a subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1-4, and seven ligands, FGF1-7. While not yet well defined, it appears that the receptors consist of a glycosylated extracellular domain containing a variable number of immunoglobulin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

Still another member of the tyrosine kinase growth factor receptor family is MET, often referred to as c-Met. c-Met is thought to play a role in primary tumor growth and metastasis.

A more complete listing of the known RTK subfamilies is described in Plowman et al., DN&P, 7(6):334–339 (1994), which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appears so far to be the largest group of CTKs and includes Src, Yes, Fyn, Lyn, Lck, Blk, Hck, Fgr and Yrk. For a more detailed discussion of CTKs, see Bolen, Oncogene, 8:2025–2031 (1993), which is incorporated by reference, including any drawings, as if fully set forth herein.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. application Ser. No. 4,966,849); soluble receptors and antibodies (Application No. WO 94/10202, Kendall and Thomas, Proc. Nat'l Acad. Sci., 90:10705–10709 (1994), Kim, et al., Nature, 362: 841–844 (1993)); RNA ligands (Jelinek, et al., Biochemistry, 33:10450–56); Takano, et al., Mol. Bio. Cell, 4:358A (1993); Kinsella, et al., Exp. Cell Res., 199:56–62 (1992); Wright, et al., J. Cellular Phys., 152:448–57) and tyrosine kinase inhibitors (WO 94/03427; WO 92/21660; WO 91/15495; WO 94/14808; U.S. Pat. No. 5,330,992; Mariani, et al., Proc. Am. Assoc. Cancer Res., 35:2268 (1994)).

In addition to the above, attempts have been made to identify small molecules which act as PK inhibitors. For example, bis-monocylic, bicyclic and heteroalicyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP Application No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

Recently, Reich et al. (WO 01/53268) have prepared indazole compounds which have been shown to be useful in mediating and inhibiting cell proliferation. The compounds disclosed therein are known to have activity as mediators of protein kinase activity.

Similarly, Cox et al. (WO 01/47922) disclosed azaindazole compounds useful as protein kinase inhibitors. Kania et al. (WO 01/02369) also disclose indazole compounds with indole substituents which are useful as inhibitors of protein kinases. Oe et al. (JP 01190681) discloses pyrazolo[3,4-b]-pyridines as antitumor agents and immunostimulents.

The compounds of the prior art fail to provide pyrrole substitued pyridopyrazole compounds which are useful for treating cell proliferative disorders by mediating protein kinases.

SUMMARY OF THE INVENTION

A family of novel pyrrole-substituted pyridopyrazole compounds and pyrrole-substituted indazole compounds has been discovered which exhibit PK modulating ability and have a salutary effect against disorders related to abnormal PK activity. It has been demonstrated that this family of compounds modulates the catalytic activity of receptor tyrosine kinases (RTKs), non-receptor protein tyrosine kinases (CTKs) and serine/threonine protein kinases (STKs).

For example, the catalytic activity of STKs such as, without limitation, PAK and ZC1 may be modulated with pyrrole-substituted pyridopyrazole compounds, in particular PAK may be modulated. By affecting the catalytic activity of RTKs, CTKs and/or STKs, such compounds can interfere with the signals transduced by such proteins.

Chemistry

In one aspect, the present invention relates to compounds having the following chemical structure (Formula I):

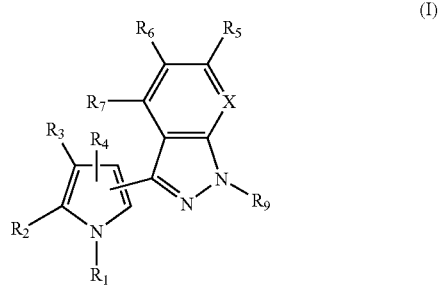

wherein X is N or $CR_8$;

$R_1$ and $R_9$ are independently H, alkyl, aryl, arylsulfonyl, alkylsulfonyl or a prodrug group selected from the group consisting of C(O)NRR', C(O)OR', $SO_2R$ and C(O)R' or moiety which is hydrolyzable under physiological conditions;

$R_2$, $R_3$ and $R_4$ are independently selected from the group consisting of H, alkyl, aryl, heteroaryl, halogen, cyano, $NO_2$, NHR', C(O)R, NHC(O)R, $NHSO_2R'$, $(CH_2)_mSO_2(CH_2)_nR$, $(CH_2)_mSO_2N(R)(CH_2)_nR'$, C(O)NHNRR', $(CH_2)_nCO_2R$, $(CH_2)_nC(O)NRR'$, NHC(O)NHR, $(CH_2)_nNRR'$, $(CH_2)_nOR'$ or $(CH_2)_nOC(O)R'$ wherein said alkyl, aryl or heteroaryl may be further substituted with halogen, $NO_2$, hydroxy, carboxylic acid, amino or a heteroalicyclic;

$R_5$, $R_6$, $R_7$ and $R_8$ are independently selected from the group consisting of H, alkyl, alkoxy, aryl, aryloxy, heteroaryl, halogen, cyano, $NO_2$, NRR', C(O)R, NHC(O)R, $(CH_2)_mSO_2(CH_2)_nR$, $(CH_2)_nSO_2NRR'$, $NHSO_2R'$, $(CH_2)_nCO_2R'$, $(CH_2)_nC(O)NRR'$, NHC(O)NHR, $(CH_2)_nNRR'$, $(CH_2)_nOR'$ trihalomethyl or $(CH_2)_nOC(O)R'$;

n is 0–3;

m is 0–3; and

R and R' are independently H, alkyl, heteroaryl or aryl, wherein alkyl or aryl may be further substituted with halogen, $NO_2$, $(CH_2)_nN(R'')_2$, $(CH_2)_nCO_2R''$, $(CH_2)_nOR''$, $(CH_2)_nOC(O)R''$, alkoxycarbonyl, aryloxycarbonyl, aminocarbonyl, a heteroalicyclic ring, aryl, alkyl, alkoxy, $—CZ_3$, $—OCZ_3$, aryloxy, $C(O)NH_2$ or heteroaryl;

R" is H, alkyl or aryl;

Z is a halogen;

alternatively, NRR' may represent a 5–7 membered heteroalicyclic ring, a 5–6 membered heteroaryl ring, wherein the heteroalicyclic ring may contain N, O or S and the cyclic structure formed about NRR' may be substituted with a moiety selected from the group consisting of alkyl, haloalkyl, alkoxy, hydroxy and halo;

where $R_4$ is bonded to either the 2 or 3 position of the pyrrole ring and the pyrazole ring is bonded to the 2 or 3 position, provided that both $R_4$ and the pyrazole ring are not bonded to the same position;

provided that (1) $R_6$ is not pyridyl, $NO_2$, or $NH_2$, when $R_1$–$R_4$, $R_9$, $R_5$, $R_7$ and $R_8$ are hydrogen and X is $CR_8$ and (2) $R_9$ is not phenyl when $R_1$–$R_4$, $R_5$, $R_6$, $R_7$ and $R_8$ are hydrogen and X is $CR_8$.

In another aspect, the present invention relates to compounds having the following chemical structure (Formula I):

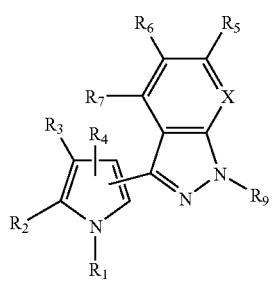

(I)

wherein X is N or $CR_8$;

$R_1$ and $R_9$ are independently H, alkyl, aryl, arylsulfonyl, alkylsulfonyl or a prodrug group selected from the group consisting of C(O)NRR', C(O)OR', $SO_2R$ and C(O)R' or moiety which is hydrolyzable under physiological conditions;

$R_2$, $R_3$ and $R_4$ are independently selected from the group consisting of H, alkyl, aryl, heteroaryl, halogen, cyano, $NO_2$, NHR', C(O)R, NHC(O)R, $NHSO_2R'$, $(CH_2)_mSO_2(CH_2)_nR$, $(CH_2)_mSO_2N(R)(CH_2)_nR'$, C(O)NHNRR', $(CH_2)_nCO_2R$, $(CH_2)_nC(O)NRR'$, NHC(O)NHR, $(CH_2)_nNRR'$, $(CH_2)_nOR'$ or $(CH_2)_nOC(O)R'$ wherein said alkyl, aryl or heteroaryl may be further substituted with halogen, $NO_2$, hydroxy, carboxylic acid, amino or a heteroalicyclic;

$R_5$, $R_6$, $R_7$ and $R_8$ are independently selected from the group consisting of H, alkyl, alkoxy, aryl, aryloxy, heteroaryl, halogen, cyano, $NO_2$, NRR', C(O)R, NHC(O)R, $(CH_2)_mSO_2(CH_2)_nR$, $(CH_2)_nSO_2NRR'$, $NHSO_2R'$, $(CH_2)_nCO_2R'$, $(CH_2)_nC(O)NRR'$, NHC(O)NHR, $(CH_2)_nNRR'$, $(CH_2)_nOR'$ trihalomethyl or $(CH_2)_nOC(O)R'$;

n is 0–3;

m is 0–3; and

R and R' are independently H, alkyl, heteroaryl, heteroalicyclic or aryl, wherein alkyl or aryl may be further substituted with halogen, $NO_2$, $(CH_2)_n(R")_2$, $(CH_2)_nCO_2R"$, $(CH_2)_nOR"$, $(CH_2)_nOC(O)R"$, alkoxycarbonyl, aryloxycarbonyl, aminocarbonyl, a heteroalicyclic ring, aryl, alkyl, alkoxy, —$CZ_3$, —$OCZ_3$, aryloxy, $C(O)NH_2$ or heteroaryl;

R" is H, alkyl or aryl;

Z is a halogen;

alternatively, NRR' may represent a 5–7 membered heteroalicyclic ring, a 5–6 membered heteroaryl ring, wherein the heteroalicyclic ring may contain N, O or S and the cyclic structure formed about NRR' may be substituted with a moiety selected from the group consisting of alkyl, haloalkyl, alkoxy, hydroxy and halo;

where $R_4$ is bonded to either the 2 or 3 position of the pyrrole ring and the pyrazole ring is bonded to the 2 or 3 position, provided that both $R_4$ and the pyrazole ring are not bonded to the same position;

provided that (1) $R_6$ is not pyridyl, $NO_2$, or $NH_2$, when $R_1$–$R_4$, $R_9$, $R_5$, $R_7$ and $R_8$ are hydrogen and X is $CR_8$ and (2) $R_9$ is not phenyl when $R_1$–$R_4$, $R_5$, $R_6$, $R_7$ and $R_8$ are hydrogen and X is $CR_8$.

The preferred embodiments of the present invention also relate to a method of treating an abnormal condition associated with protein kinase activity comprising administering to a patient in need thereof, an effective amount of a compound of formula I or II (formula II is set forth below).

The preferred embodiments of the present invention further relate to a pharmaceutical composition comprising a compound of formula I or II and a pharmaceutically acceptable carrier.

The preferred embodiments of the present invention relate to a method of treating cell proliferation, differentiation or apoptosis associated with protein kinase activity comprising administering to a patient in need thereof, an effective amount of a compound of formula I or II.

The preferred embodiments of the present invention also relate to a method of inhibiting protein kinase signal transduction comprising administering to a patient in need thereof an effective amount of a compound of formula I or II.

Finally, the preferred embodiments of the present invention relate to a method of activating protein kinase signal transduction comprising administering to a patient in need thereof an effective amount of a compound of formula I or II.

Compounds—Preferred Structural Features

In one embodiment are compounds of formula (I), wherein X is $CR_8$. In the other embodiment are compounds of formula (I) where X is N. In a preferred embodiment are compounds of formula (I) wherein $R_2$ and $R_3$ are independently selected from the group consisting of halogen, $NO_2$, C(O)R, NHC(O)R, $(CH_2)_mSO_2N(R)(CH_2)_nR'$, $(CH_2)_mSO_2(CH_2)_nR$, $(CH_2)_nCO_2R$, and $(CH_2)_nC(O)NRR'$. In yet another preferred embodiment are compounds of formula (I) where $R_6$ is selected from the group consisting of NHC(O)R, $(CH_2)_mSO_2(CH_2)_nR$, trihalomethyl and $NO_2$. In still another preferred embodiment are compounds of formula (I) where $R_5$ is halogen, amino or heteroalicyclic ring. In yet another preferred embodiment are compounds of formula (I) where $R_1$ and $R_9$ are selected from the group consisting of H, alkyl, C(O)OR' or $SO_2R$. In yet another embodiment are compounds of formula (I) wherein $R_3$ is selected from the group consisting of halogen, C(O)R, NHC(O)R, $(CH_2)_mSO_2(CH_2)_n$ R, $(CH_2)_mSO_2N(R)(CH_2)_nR'$, $(CH_2)_nCO_2R$, and $(CH_2)_nC(O)NRR'$. In still another embodiment are compounds of the formula (I) wherein $R_6$ is selected from the group consisting of NHC(O)R and $NO_2$.

A preferred aspect of the invention relates to compounds of Formula II

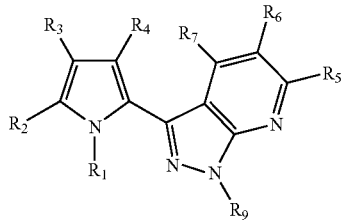

(II)

$R_1$ and $R_9$ are independently H, alkyl, aryl, arylsulfonyl, alkylsulfonyl or a prodrug group selected from the group consisting of C(O)NRR', C(O)OR', SO$_2$R and C(O)R' or moiety which is hydrolyzable under physiological conditions;

$R_2$, $R_3$ and $R_4$ are independently selected from the group consisting of H, alkyl, aryl, heteroaryl, halogen, cyano, NO$_2$, NHR', C(O)R, NHC(O)R, NHSO$_2$R', (CH$_2$)$_m$SO$_2$(CH$_2$)$_n$R, (CH$_2$)$_m$SO$_2$N(R)(CH$_2$)$_n$R', C(O)NHNRR', (CH$_2$)$_n$CO$_2$R, (CH$_2$)$_n$C(O)NRR', NHC(O)NHR, (CH$_2$)$_n$NRR', (CH$_2$)$_n$OR' or (CH$_2$)$_n$OC(O)R' wherein said alkyl, aryl or heteroaryl may be further substituted with halogen, NO$_2$, hydroxy, carboxylic acid, amino or a heteroalicyclic;

$R_5$, $R_6$, $R_7$ and $R_8$ are independently selected from the group consisting of H, alkyl, alkoxy, aryl, aryloxy, heteroaryl, halogen, cyano, NO$_2$, NRR', C(O)R, NHC(O)R, (CH$_2$)$_m$SO$_2$(CH$_2$)$_n$R, (CH$_2$)$_n$SO$_2$NRR', NHSO$_2$R', (CH$_2$)$_n$CO$_2$R', (CH$_2$)$_n$C(O)NRR', NHC(O)NHR, (CH$_2$)$_n$NRR', (CH$_2$)$_n$OR' trihalomethyl or (CH$_2$)$_n$OC(O)R';

n is 0–3;

m is 0–3; and

R and R' are independently H, alkyl, heteroaryl or aryl, wherein alkyl or aryl may be further substituted with halogen, NO$_2$, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, a heteroalicyclic ring, aryl, alkyl, alkoxy, —CZ$_3$, —OCZ$_3$, aryloxy, C(O)NH$_2$ or heteroaryl;

R" is H, alkyl or aryl; and

Z is a halogen;

alternatively, NRR' may represent a 5–7 membered heteroalicyclic ring, a 5–6 membered heteroaryl ring, wherein the heteroalicyclic ring may contain N, O or S and the cyclic structure formed about NRR' may be substituted with a moiety selected from the group consisting of alkyl, haloalkyl, alkoxy, hydroxy and halo.

The compounds presented herein are exemplary only and are not to be construed as limiting the scope of this invention in any manner.

In addition, the formulae referred to herein may also exhibit stereoisomerism, in which such compounds may adopt an R or S configuration at chiral centers. Thus, this invention also encompasses any stereoisomeric form, their corresponding enantiomers (d- and l- or (+) and (−) isomers) and diastereomers thereof, and mixtures thereof, which possess the ability to modulate RTK, CTK and/or STK activity and is not limited to any one stereoisomeric form.

Table 1 show the chemical structures of the preferred compounds of the invention.

| Ex. No. | Structure | Name |
|---|---|---|
| 1 | 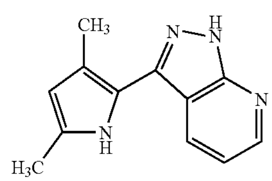 | 3-(3,5-Dimethyl-1H-pyrrol-2-yl)-1H-pyrazolo[3,4-b]pyridine |
| 2 | 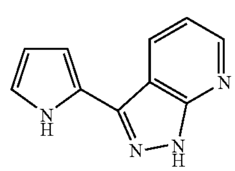 | 3-(1H-Pyrrol-2-yl)-1H-pyrazolo[3,4-b]pyridine |
| 3 | 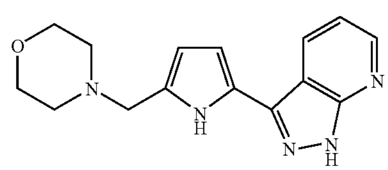 | 3-(5-Morpholin-4-ylmethyl-1H-pyrrol-2-yl)-1H-pyrazolo[3,4-b]pyridine |
| 4 | 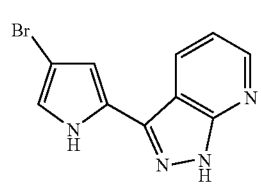 | 3-(4-Bromo-1H-pyrrol-2-yl)-1H-pyrazolo[3,4-b]pyridine |

-continued
| Ex. No. | Structure | Name |
|---|---|---|
| 5 | 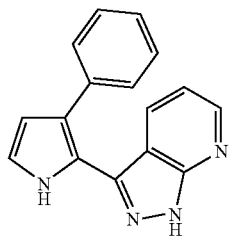 | 3-(3-Phenyl-1H-pyrrol-2-yl)-1H-pyrazolo[3,4-b]pyridine |
| 6 | 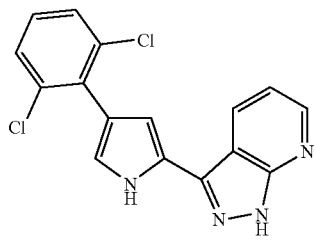 | 3-[4-(2,6-Dichloro-phenyl)-1H-pyrrol-2-yl]-1H-pyrazolo[3,4-b]pyridine |
| 7 | 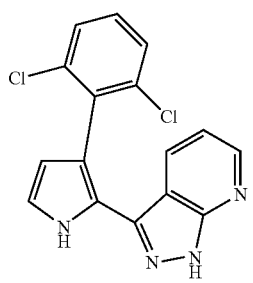 | 3-[3-(2,6-Dichloro-phenyl)-1H-pyrrol-2-yl]-1H-pyrazolo[3,4-b]pyridine |
| 8 | 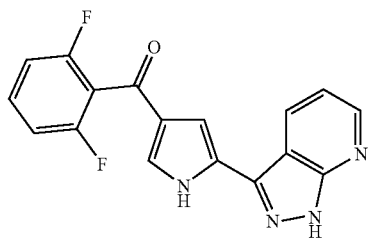 | (2,6-Difluoro-phenyl)-[5-(1H-pyrazolo [3,4-b]pyridin-3-yl)-1H-pyrrol-3-yl]-methanone |
| 9 | 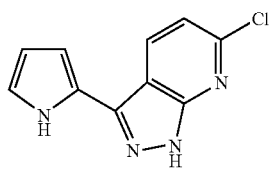 | 6-Chloro-3-(1H-pyrrol-2-yl)-1H-pyrazolo[3,4-b]pyridine |
| 10 | 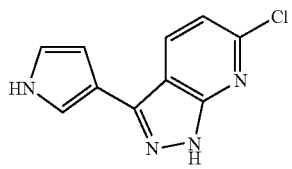 | 6-Chloro-3-(1H-pyrrol-3-yl)-1H-pyrazolo[3,4-b]pyridine |

-continued

| Ex. No. | Structure | Name |
|---|---|---|
| 11 | 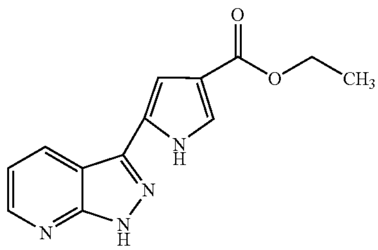 | 5-(1H-Pyrazolo[3,4-b]pyridin-3-yl)-1H-pyrrole-3-carboxylic acid ethyl ester |
| 12 | 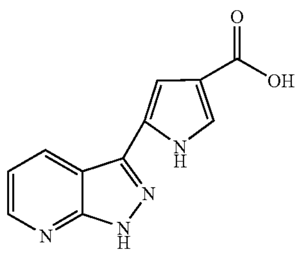 | 5-(1H-Pyrazolo[3,4-b]pyridin-3-yl)-1H-pyrrole-3-carboxylic acid |
| 13 | 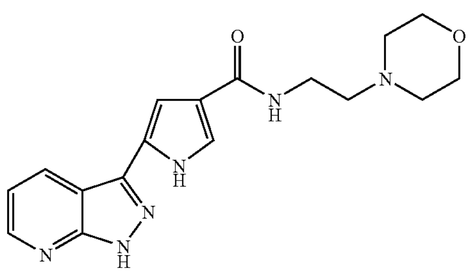 | 5-(1H-Pyrazolo[3,4-b]pyridin-3-yl)-1H-pyrrole-3-carboxylic acid (2-morpholin-4-yl-ethyl)-amide |
| 14 | 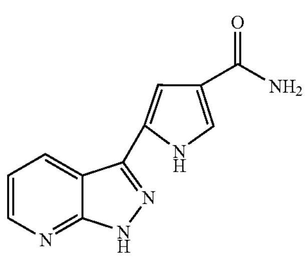 | 5-(1H-Pyrazolo[3,4-b]pyridin-3-yl)-1H-pyrrole-3-carboxylic acid amide |
| 15 | 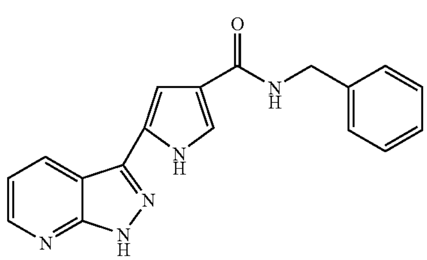 | 5-(1H-Pyrazolo[3,4-b]pyridin-3-yl)-1H-pyrrole-3-carboxylic acid benzylamide |
| 16 | 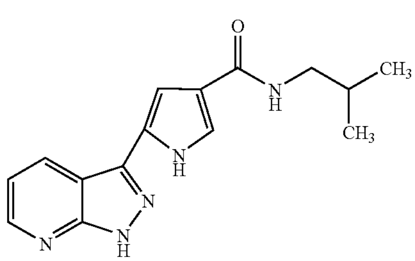 | 5-(1H-Pyrazolo[3,4-b]pyridin-3-yl)-1H-pyrrole-3-carboxylic acid isobutyl-amide |

-continued

| Ex. No. | Structure | Name |
|---|---|---|
| 17 | 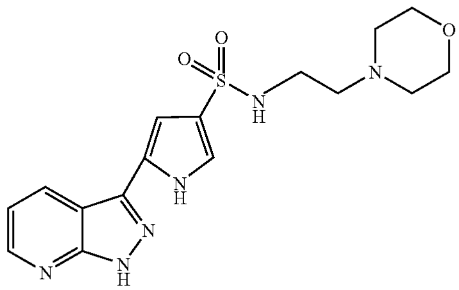 | 5-(1H-Pyrazolo[3,4-b]pyridin-3-yl)-1H-pyrrole-3-sulfonic acid (2-morpholin-4-yl-ethyl)-amide |
| 18 | 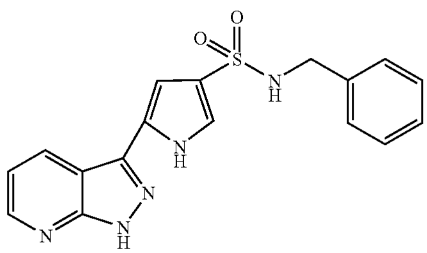 | 5-(1H-Pyrazolo[3,4-b]pyridin-3-yl)-1H-pyrrole-3-sulfonic acid benzylamide |
| 19 | 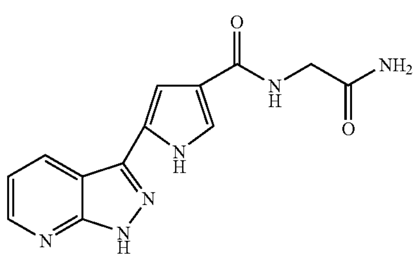 | 5-(1H-Pyrazolo[3,4-b]pyridin-3-yl)1H-pyrrole-3-carboxylic acid carbamoylmethyl-amide |
| 20 | 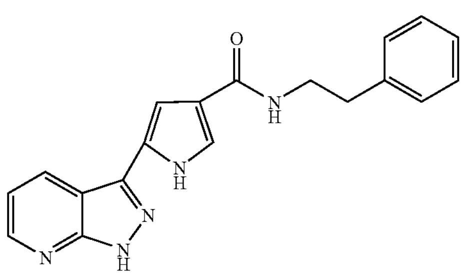 | 5-(1H-Pyrazolo[3,4-b]pyridin-3-yl)-1H-pyrrole-3-carboxylic acid phenethyl-amide |
| 21 | 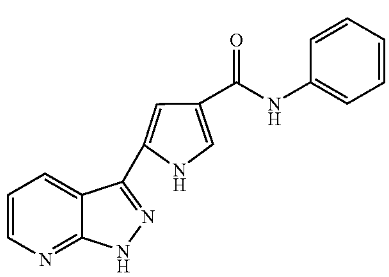 | 5-(1H-Pyrazolo[3,4-b]pyridin-3-yl)-1H-pyrrole-3-carboxylic acid phenylamide |

-continued

| Ex. No. | Structure | Name |
|---|---|---|
| 22 | 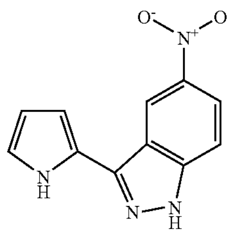 | 5-Nitro-3-(1H-pyrrol-2-yl)-1H-indazole |
| 23 | 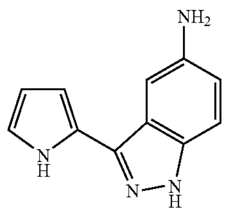 | 3-(1H-Pyrrol-2-yl)-1H-indazol-5-ylamine |
| 24 | 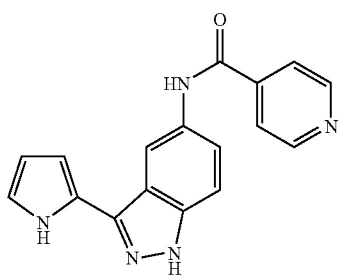 | N-[3-(1H-Pyrrol-2-yl)-1H-indazol-5-yl]-isonicotinamide |
| 25 | 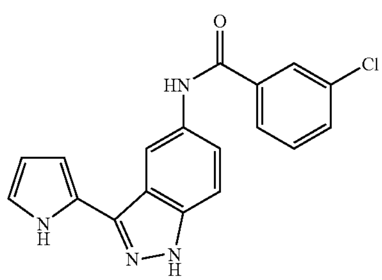 | 3-Chloro-N-[3-(1H-pyrrol-2-yl)-H-indazol-5-yl]-benzamide |
| 26 | 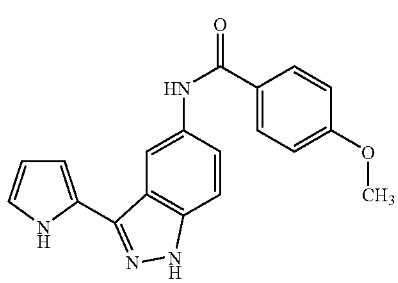 | 4-Methoxy-N-[3-(1H-pyrrol-2-yl)-1H-indazol-5-yl]-benzamide |
| 27 | 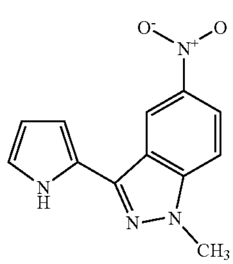 | 1-Methyl-5-nitro-3-(1H-pyrrol-2-yl)-1H-indazole |

-continued

| Ex. No. | Structure | Name |
|---|---|---|
| 28 | 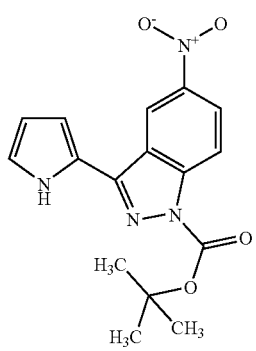 | 5-Nitro-3-(1H-pyrrol-2-yl)-indazole-1-carboxylic acid tert-butyl ester |
| 29 | 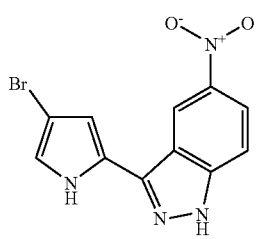 | 3-(4-Bromo-1H-pyrrol-2-yl)-5-nitro-1H-indazole |
| 30 | 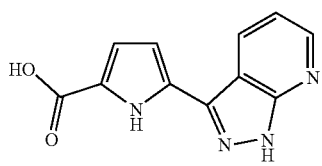 | 5-(1H-Pyrazolo[3,4-b]pyridin-3-yl)-1H-pyrrole-2-carboxylic acid |
| 31 | 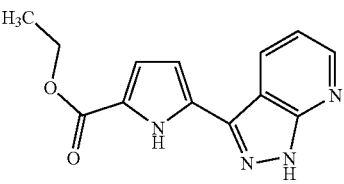 | 5-(1H-Pyrazolo[3,4-b]pyridin-3-yl)-1H-pyrrole-2-carboxylic acid ethyl ester |
| 32 | 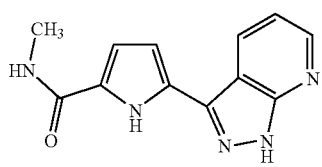 | 5-(1H-Pyrazolo[3,4-b]pyridin-3-yl)-1H-pyrrole-2-carboxylic acid methylamide |
| 33 | 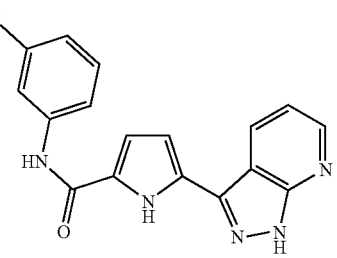 | 5-(1H-Pyrazolo[3,4-b]pyridin-3-yl)-1H-pyrrole-2-carboxylic acid (3-fluoro-phenyl)-amide |

-continued

| Ex. No. | Structure | Name |
|---|---|---|
| 34 | 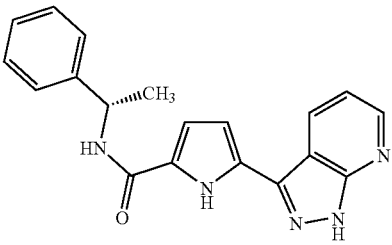 Chiral | 5-(1H-Pyrazolo[3,4-b]pyridin-3-yl)-1H-pyrrole-2-carboxylic acid ((S)-1-phenyl-ethyl)-amide |
| 35 | 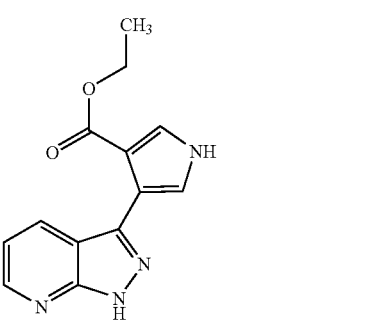 | 4-(1H-Pyrazolo[3,4-b]pyridin-3-yl)-1H-pyrrole-3-carboxylic acid ethyl ester |
| 36 | 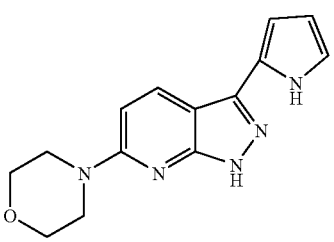 | 6-Morpholin-4-yl-3-(1H-pyrrol-2-yl)-1H-pyrazolo[3,4-b]pyridine |
| 37 | 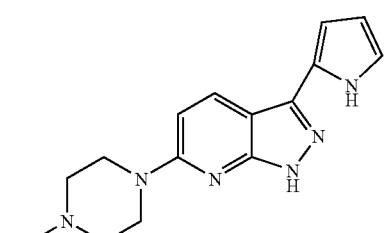 | 6-(4-Methyl-piperazin-1-yl)-3-(1H-pyrrol-2-yl)-1H-pyrazolo[3,4-b]pyridine |
| 38 | 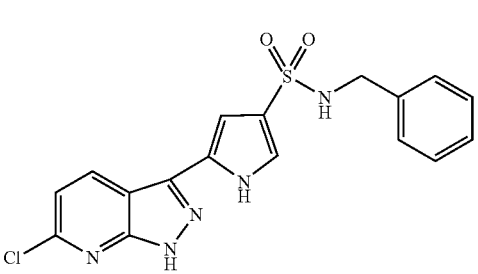 | 5-(6-Chloro-1H-pyrazolo[3,4-b]pyridin-3-yl)-1H-pyrrole-3-sulfonic acid benzylamide |
| 39 | 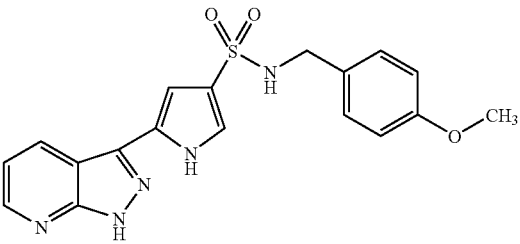 | 5-(1H-Pyrazolo[3,4-b]pyridin-3-yl)-1H-pyrrole-3-sulfonic acid 4-methoxy-benzylamide |

-continued

| Ex. No. | Structure | Name |
|---|---|---|
| 40 | 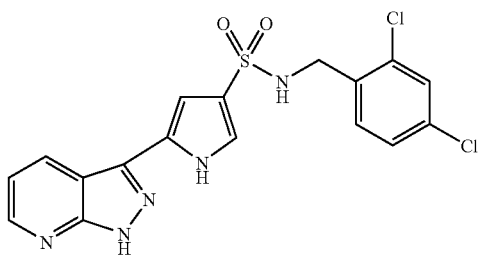 | 5-(1H-Pyrazolo[3,4-b]pyridin-3-yl)-1H-pyrrole-3-sulfonic acid 2,4-dichloro-benzylamide |
| 41 | 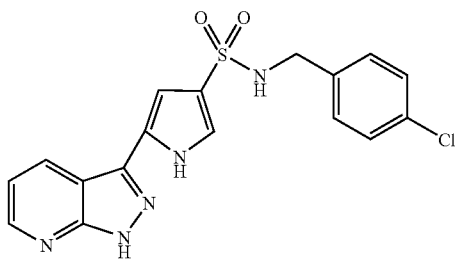 | 5-(1H-Pyrazolo[3,4-b]pyridin-3-yl)-1H-pyrrole-3-sulfonic acid 4-chloro-benzylamide |
| 42 | 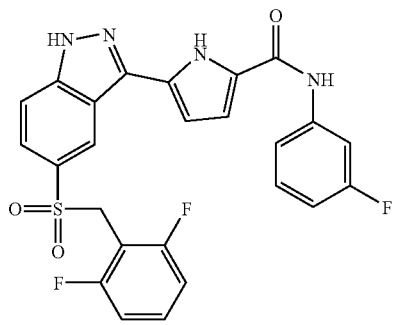 | 5-[5-(2,6-Difluoro-phenylmethanesulfonyl)-1H-indazol-3-yl]-1H-pyrrole-2-carboxylic acid (3-fluoro-phenyl)-amide |
| 43 | 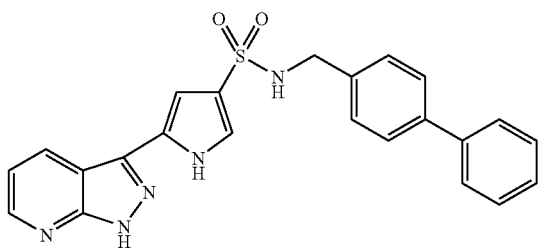 | 5-(1H-Pyrazolo[3,4-b]pyridin-3-yl)-1H-pyrrole-3-sulfonic acid (biphenyl-4-ylmethyl)-amide |
| 44 | 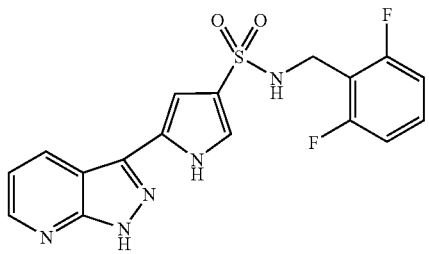 | 5-(1H-Pyrazolo[3,4-b]pyridin-3-yl)-1H-pyrrole-3-sulfonic acid 2,6-difluoro-benzylamide |

-continued

| Ex. No. | Structure | Name |
|---|---|---|
| 45 | 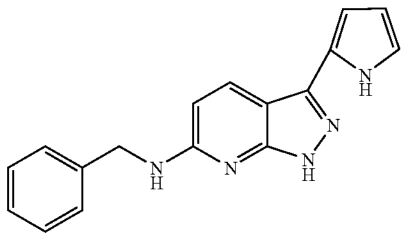 | Benzyl-[3-(1H-pyrrol-2-yl)-1H-pyrazolo[3,4-b]pyridin-6-yl]-amine |
| 46 | 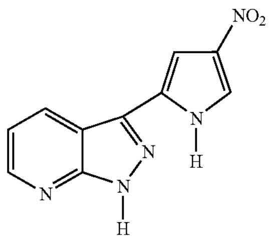 | 3-(4-Nitro-1H-pyrrol-2-yl)-1H-pyrazolo[3,4-b]pyridine |
| 47 | 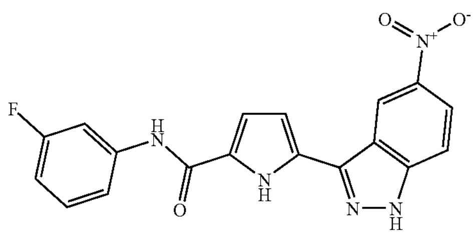 | 5-(5-Nitro-1H-indazol-3-yl)-1H-pyrrole-2-carboxylic acid (3-fluoro-phenyl)-amide |
| 48 | 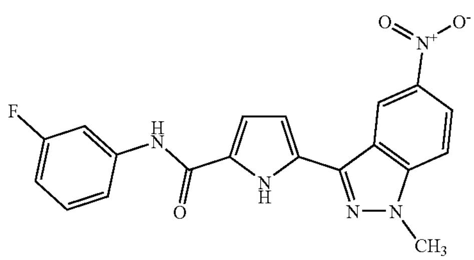 | 5-(1-Methyl-5-nitro-1H-indazol-3-yl)-1H-pyrrole-2-carboxylic acid (3-fluoro-phenyl)-amide |
| 49 | 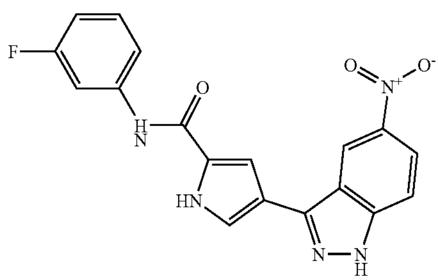 | 4-(5-Nitro-1H-indazol-3-yl)-1H-pyrrole-2-carboxylic acid (3-fluoro-phenyl)-amide |
| 50 | 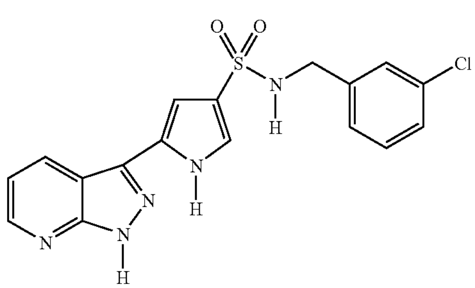 | 5-(1H-Pyrazolo[3,4-b]pyridin-3-yl)-1H-pyrrole-3-sulfonic acid 3-chloro-benzylamide |

-continued

| Ex. No. | Structure | Name |
|---|---|---|
| 51 | 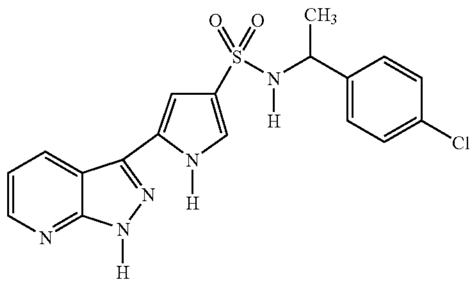 | 5-(1H-Pyrazolo[3,4-b]pyridin-3-yl)-1H-pyrrole-3-sulfonic acid [1-(4-chloro-phenyl)-ethyl]-amide |
| 52 | 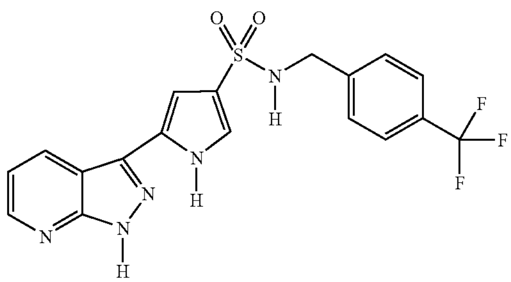 | 5-(1H-Pyrazolo[3,4-b]pyridin-3-yl)-1H-pyrrole-3-sulfonic acid 4-trifluoromethyl-benzylamide |
| 53 | 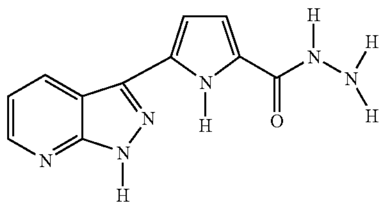 | 5-(1H-Pyrazolo[3,4-b]pyridin-3-yl)-1H-pyrrole-2-carboxylic acid hydrazide |
| 54 | 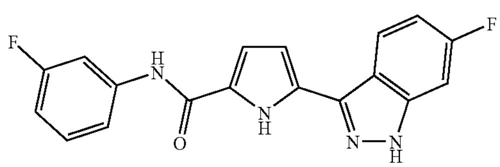 | 5-(6-Fluoro-1H-indazol-3-yl)-1H-pyrrole-2-carboxylic acid (3-fluoro-phenyl)-amide |
| 55 | 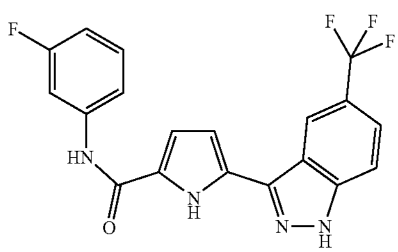 | 5-(5-Trifluoromethyl-1H-indazol-3-yl)-1H-pyrrole-2-carboxylic acid (3-fluoro-phenyl)-amide |
| 56 | 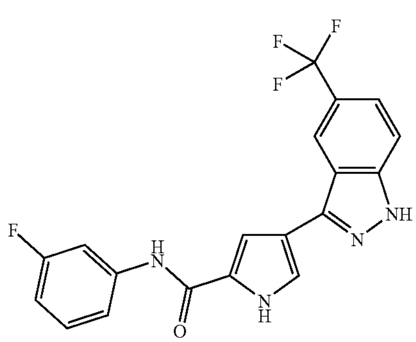 | 4-(5-Trifluoromethyl-1H-indazol-yl)-1H-pyrrole-2-carboxylic acid (3-fluoro-phenyl)-amide |

-continued

| Ex. No. | Structure | Name |
|---|---|---|
| 57 | 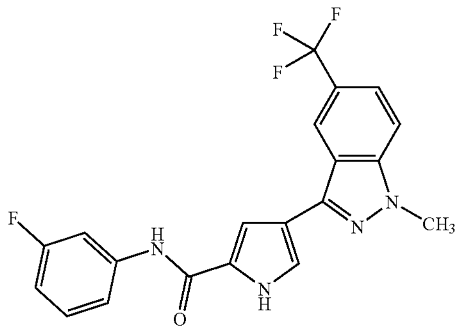 | 4-(1-Methyl-5-trifluoromethyl-1H-indazol-3-yl)-1H-pyrrole-2-carboxylic acid (3-fluoro-phenyl)-amide |
| 58 | 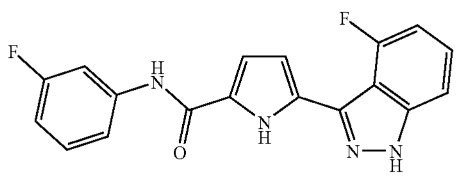 | 5-(4-Fluoro-1H-indazol-3-yl)-1H-pyrrole-2-carboxylic acid (3-fluoro-phenyl)-amide |
| 59 | 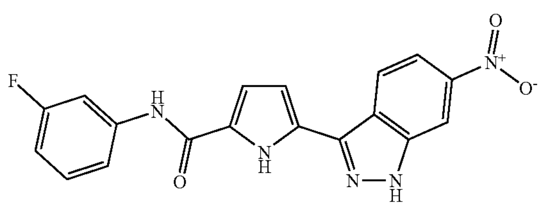 | 5-(6-Nitro-1H-indazol-3-yl)-1H-pyrrole-2-carboxylic acid (3-fluoro-phenyl)-amide |
| 60 | 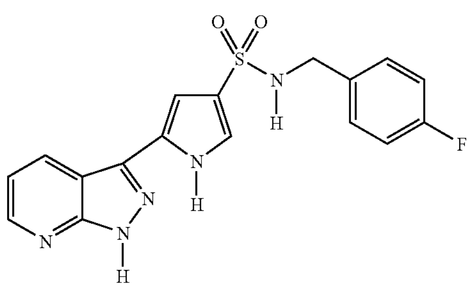 | 5-(1H-Pyrazolo[3,4-b]pyridin-3-yl)-1H-pyrrole-3-sulfonic acid 4-fluoro-benzylamide |
| 61 | 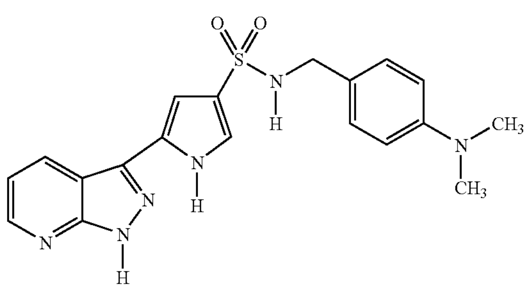 | 5-(1H-Pyrazolo[3,4-b]pyridin-3-yl)-1H-pyrrole-3-sulfonic acid 4-dimethylamino-benzylamide |
| 62 | 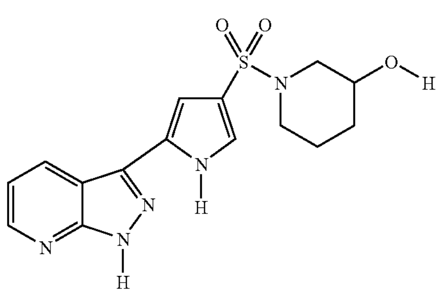 | 1-[5-(1H-Pyrazolo[3,4-b]pyridin-3-yl)-1H-pyrrole-3-sulfonyl]-piperidin-3-ol |

-continued
| Ex. No. | Structure | Name |
|---|---|---|
| 63 | 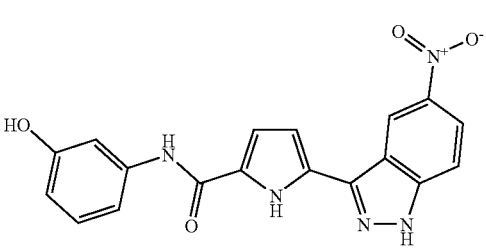 | 5-(5-Nitro-1H-indazol-3-yl)-1H-pyrrole-2-carboxylic acid (3-hydroxy-phenyl)-amide |
| 64 | 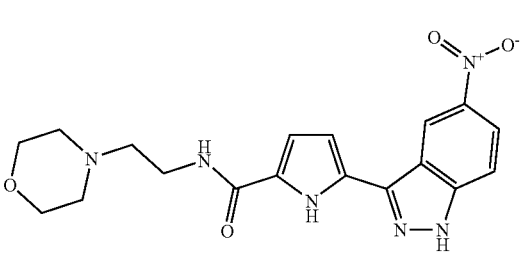 | 5-(5-Nitro-1H-indazol-3-yl)-1H-pyrrole-2-carboxylic acid (2-morpholin-4-yl-ethyl)-amide |
| 65 | 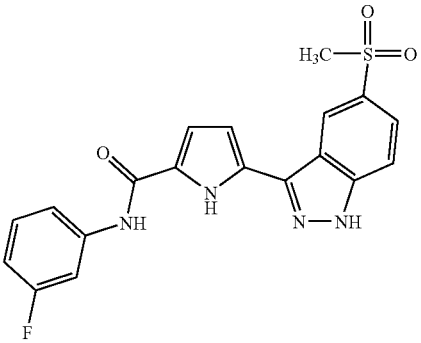 | 5-(5-Methanesulfonyl-1H-indazol-3-yl)-1H-pyrrole-2-carboxylic acid (3-fluoro-phenyl)-amide |
| 66 | 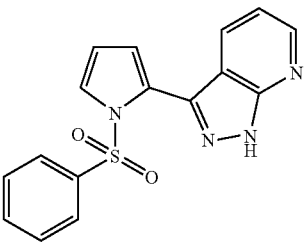 | 3-(1-Benzenesulfonyl-1H-pyrrol-2-yl)-1H-pyrazolo[3,4-b]pyridine |
| 67 | 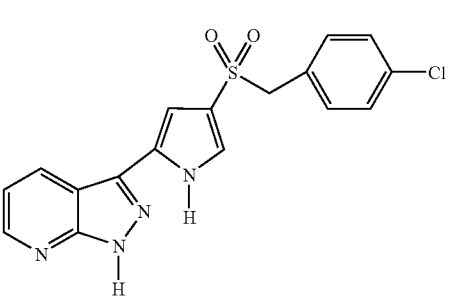 | 3-[4-(4-Chloro-phenylmethanesulfonyl)-1H-pyrrol-2-yl]-1H-pyrazolo[3,4-b]pyridine |

| Ex. No. | Structure | Name |
|---|---|---|
| 68 | 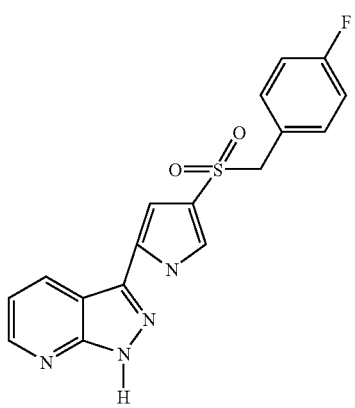 | 3-[4-(4-Fluoro-phenylmethanesulfonyl)-1H-pyrrol-2-yl]-1H-pyrazolo[3,4-b]pyridine |
| 69 | 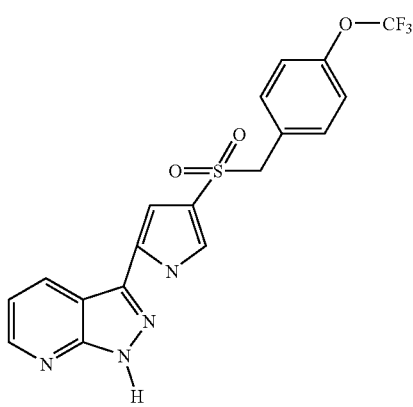 | 3-[4-(4-Trifluoromethoxy-phenylmethanesulfonyl)-1H-pyrrol-2-yl]-1H-pyrazolo[3,4-b]pyridine |
| 70 | 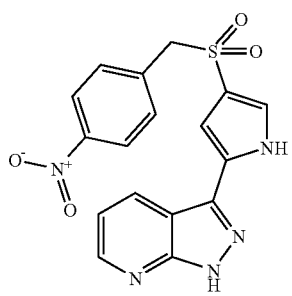 | 3-[4-(4-Nitro-phenylmethanesulfonyl)-1H-pyrrol-2-yl]-1H-pyrazolo[3,4-b]pyridine |
| 71 | 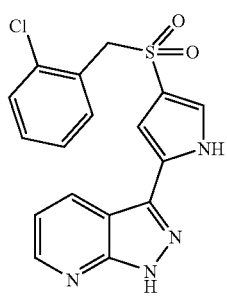 | 3-[4-(2-Chloro-phenylmethanesulfonyl)-1H-pyrrol-2-yl]-1H-pyrazolo[3,4-b]pyridine |

| Ex. No. | Structure | Name |
|---|---|---|
| 72 | 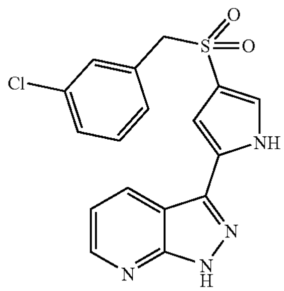 | 3-[4-(3-Chloro-phenylmethanesulfonyl)-1H-pyrrol-2-yl]-1H-pyrazolo[3,4-b]pyridine |
| 73 | 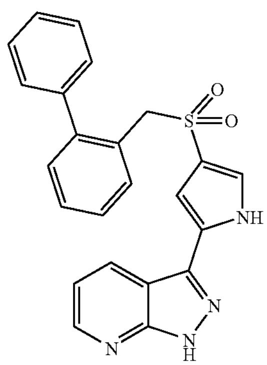 | 3-[4-(Biphenyl-2-ylmethanesulfonyl)-1H-pyrrol-2-yl]-1H-pyrazolo[3,4-b]pyridine |
| 74 | 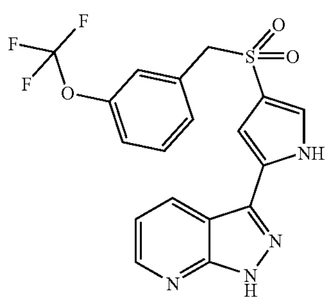 | 3-[4-(3-Trifluoromethoxy-phenylmethanesulfonyl)-1H-pyrrol-2-yl]-1H-pyrazolo[3,4-b]pyridine |
| 75 | 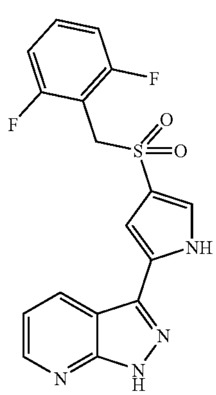 | 3-[4-(2,6-Difluoro-phenylmethanesulfonyl)-1H-pyrrol-2-yl]-1H-pyrazolo[3,4-b]pyridine |

| Ex. No. | Structure | Name |
|---|---|---|
| 76 | 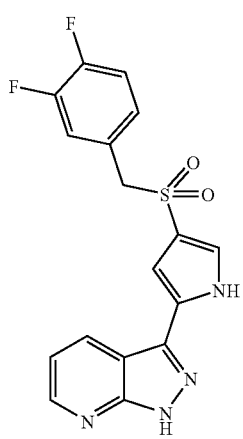 | 3-[4-(3,4-Difluoro-phenylmethanesulfonyl)-1H-pyrrol-2-yl]-1H-pyrazolo[3,4-b]pyridine |
| 77 | 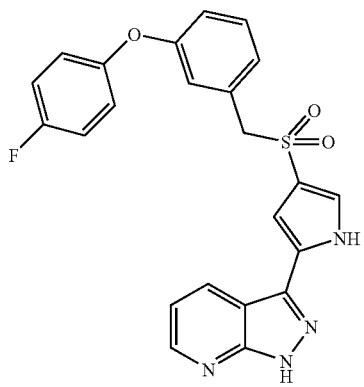 | 3-{4-[3-(4-Fluoro-phenoxy)-phenylmethanesulfonyl]-1H-pyrrol-2-yl}-1H-pyrazolo[3,4-b]pyridine |
| 78 | 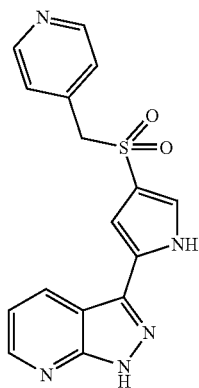 | 3-[4-(Pyridin-4-ylmethanesulfonyl)-1H-pyrrol-2-yl]-1H-pyrazolo[3,4-b]pyridine |

-continued

| Ex. No. | Structure | Name |
|---|---|---|
| 79 | 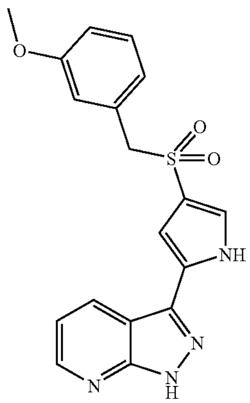 | 3-[4-(3-Methoxy-phenylmethanesulfonyl)-1H-pyrrol-2-yl]-1H-pyrazolo[3,4-b]pyridine |
| 80 | 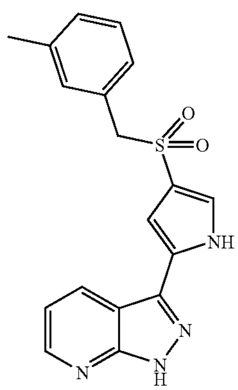 | 3-(4-m-Tolylmethanesulfonyl-1H-pyrrol-2-yl)-1H-pyrazolo[3,4-b]pyridine |
| 81 | 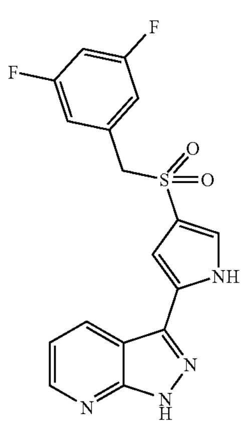 | 3-[4-(3,5-Difluoro-phenylmethanesulfonyl)-1H-pyrrol-2-yl]-1H-pyrazolo[3,4-b]pyridine |
| 82 | 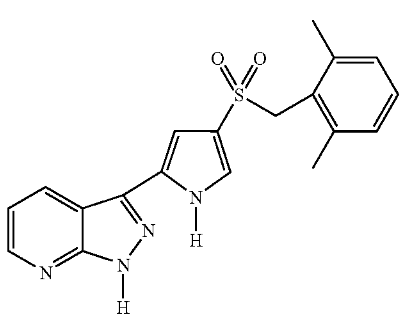 | 3-[4-(2,6-Dimethyl-phenylmethanesulfonyl)-1H-pyrrol-2-yl]-1H-pyrazolo[3,4-b]pyridine |

| Ex. No. | Structure | Name |
|---|---|---|
| 83 | 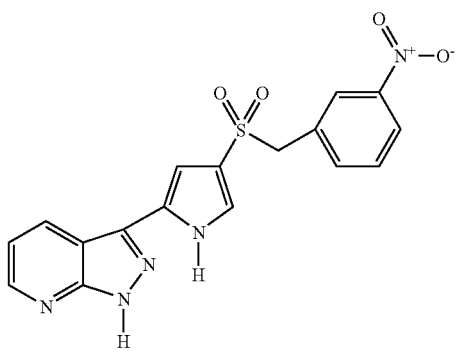 | 3-[4-(3-Nitro-phenylmethanesulfonyl)-1H-pyrrol-2-yl]-1H-pyrazolo[3,4-b]pyridine |
| 84 | 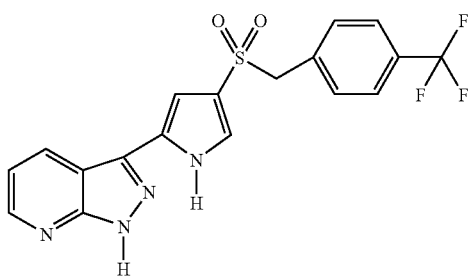 | 3-[4-(4-Trifluoromethyl-phenylmethanesulfonyl)-1H-pyrrol-2-yl]-1H-pyrazolo[3,4-b]pyridine |
| 85 | 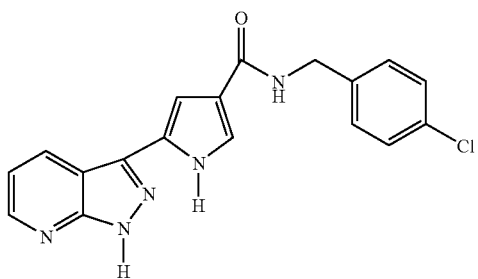 | 5-(1H-pyrazolo[3,4-b]pyridin-3-yl)-1H-pyrrole-3-carboxylic acid, 4-chlorobenzylamide |
| 86 | 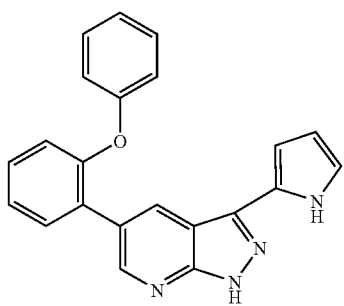 | 5-(2-phenoxyphenyl)-3-(1H-pyrrol-2-yl)-1H-pyrazolo[3,4-b]pyridine |
| 87 | 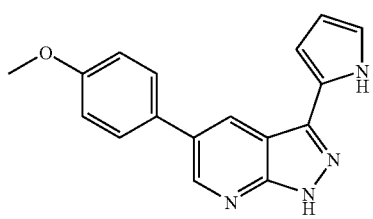 | 5-(4-methoxyphenyl)-3-(1H-pyrrol-2-yl)-1H-pyrazolo[3,4-b]pyridine |

| Ex. No. | Structure | Name |
|---|---|---|
| 88 | 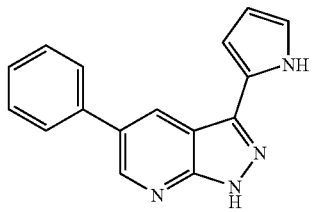 | 5-phenyl-3-(1H-pyrrol-2-yl)-1H-pyrazolo[3,4-b]pyridine |
| 89 | 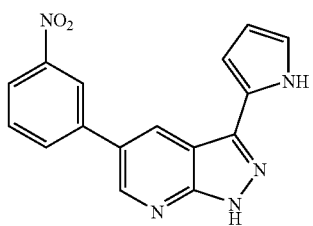 | 5-(3-nitrophenyl)-3-(1H-pyrrol-2-yl)-1H-pyrazolo[3,4-b]pyridine |
| 90 | 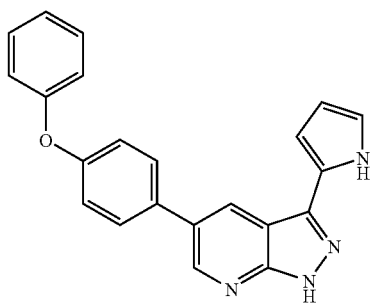 | 5-(4-phenoxyphenyl)-3-(1H-pyrrol-2-yl)-1H-pyrazolo[3,4-b]pyridine |
| 91 | 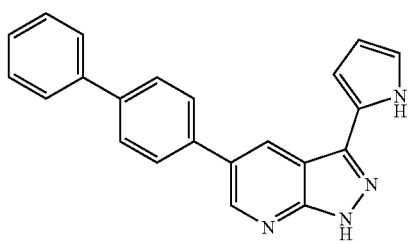 | 5-(1,1'-biphenyl-4-yl)-3-(1H-pyrrol-2-yl)-1H-pyrazolo[3,4-b]pyridine |
| 92 | 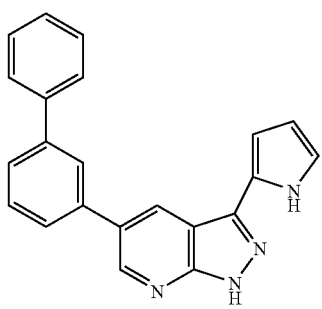 | 5-(1,1'-biphenyl-3-yl)-3-(1H-pyrrol-2-yl)-1H-pyrazolo[3,4-b]pyridine |

-continued
| Ex. No. | Structure | Name |
|---|---|---|
| 93 | 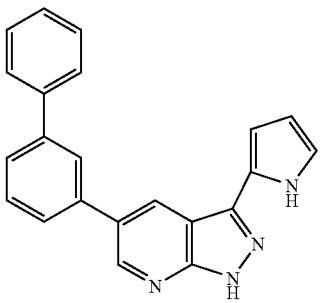 | 5-(1,1'-biphenyl-2-yl)-3-(1H-pyrrol-2-yl)-1H-pyrazolo[3,4-b]pyridine |
| 94 | 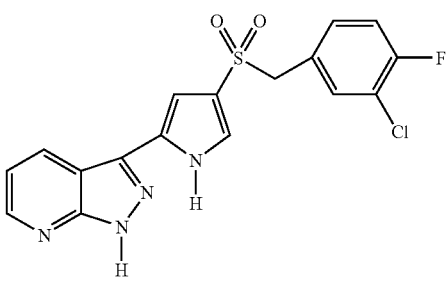 | 3-{4-[(3-chloro-4-fluorobenzyl)sulfonyl]-1H-pyrrol-2-yl}-1H-pyrazolo[3,4-b]pyridine |
| 95 | 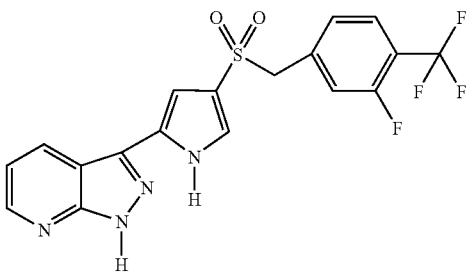 | 3-(4-{[3-fluoro-4-(trifluoromethyl)benzyl]sulfonyl}1H-pyrrol-2-yl)-1H-pyrazolo[3,4-b]pyridine |
| 96 | 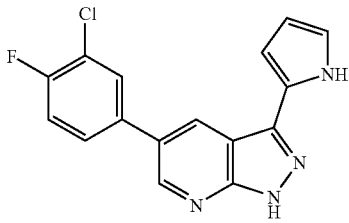 | 5-(3-chloro-4-fluorophenyl)-3-(1H-pyrrol-2-yl)-1H-pyrazolo[3,4-b]pyridine |
| 97 | 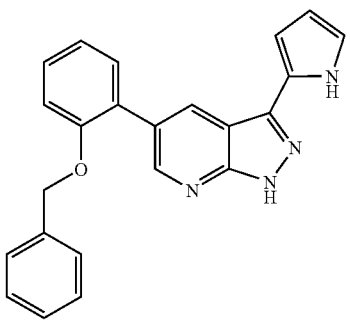 | 5-[2-(benzyloxy)phenyl]-3-(1H-pyrrol-2-yl)-1H-pyrazolo[3,4-b]pyridine |

| Ex. No. | Structure | Name |
|---|---|---|
| 98 | 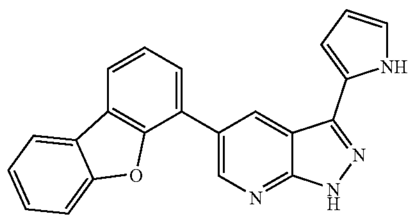 | 5-dibenzo[b,d]furan-4-yl-3-(1H-pyrrol-2-yl)-1H-pyrazolo[3,4-b]pyridine |
| 99 | 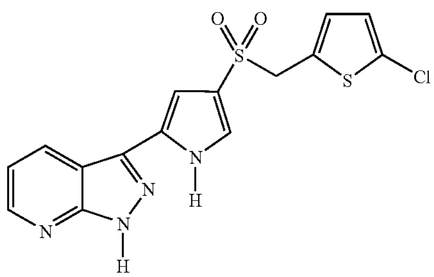 | 3-(4-{[(5-chlorothien-2-yl)methyl]sulfonyl}-1H-pyrrol-2-yl)-1H-pyrazolo[3,4-b]pyridine |
| 100 | 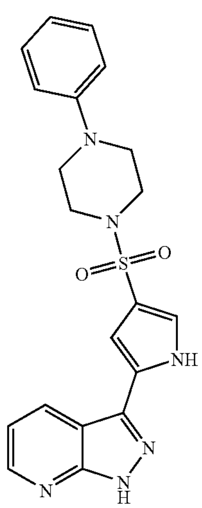 | 3-{4-[(4-phenylpiperazin-1-yl)sulfonyl]-1H-pyrrol-2-yl}-1H-pyrazolo[3,4-b]pyridine |
| 101 | 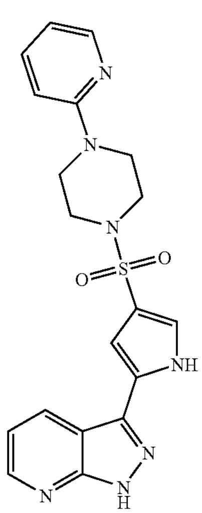 | 3-{4-[(4-pyridin-2-ylpiperazin-1-yl)sulfonyl]-1H-pyrrol-2-yl}-1H-pyrazolo[3,4-b]pyridine |

| Ex. No. | Structure | Name |
|---|---|---|
| 102 | 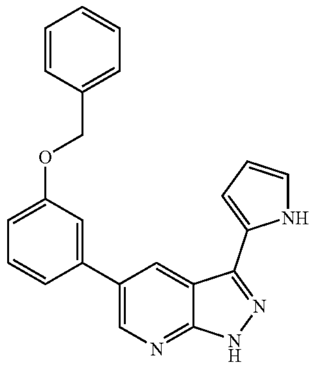 | 5-[3-(benzyloxy)phenyl]-3-(1H-pyrrol-2-yl)-1H-pyrazolo[3,4-b]pyridine |
| 103 | 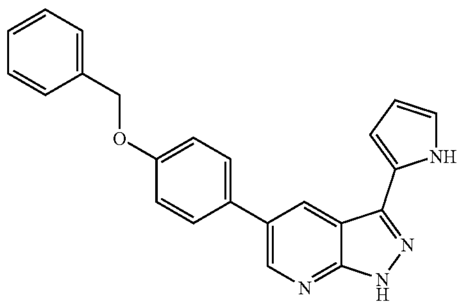 | 5-[4-(benzyloxy)phenyl]-3-(1H-pyrrol-2-yl)-1H-pyrazolo[3,4-b]pyridine |
| 104 | 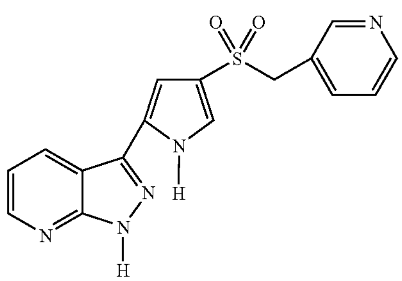 | 5-[4-(benzyloxy)phenyl]-3-(1H-pyrrol-2-yl)-1H-pyrazolo[3,4-b]pyridine |
| 105 | 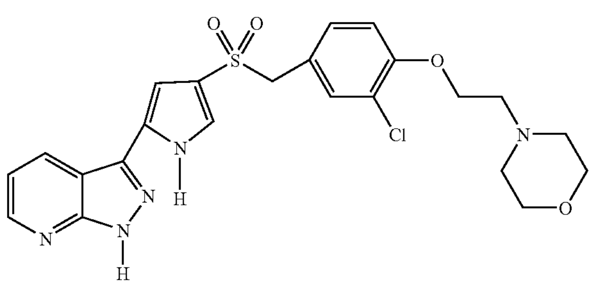 | 3-{4-[3-chloro-4-(2-morpholin-4-yl-ethoxy)-phenylmethanesulfonyl)-1H-pyrrol-2-yl}-1H-pyrazolo[3,4-b]pyridine |

| Ex. No. | Structure | Name |
|---|---|---|
| 106 | 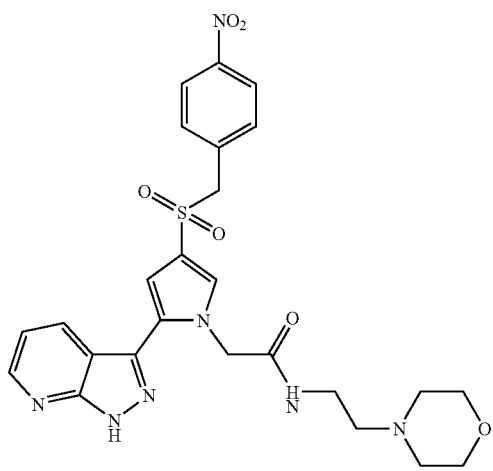 | 2-[4-(4-nitro-phenylmethanesulfonyl)-2-(1H-pyrazolo[3,4-b]pyridin-3-yl)-pyrrol-1-yl]-N-(2-morpholin-4-yl-ethyl)-acetamide |
| 107 | 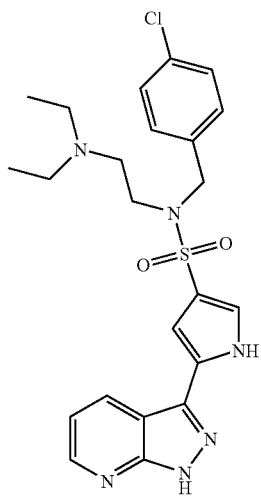 | 5-(1H-Pyrazolo[3,4-b]pyridin-3-yl)-1H-pyrrole-3-sulfonic acid (4-chloro-benzyl)-(2-diethylamino-ethyl)-amide |
| 108 | 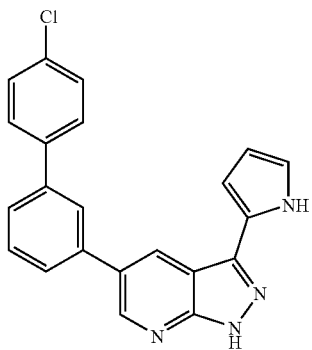 | 5-(4'-chloro-1,1'-biphenyl-3-yl)-3-(1H-pyrrol-2-yl)-1H-pyrazolo[3,4-b]pyridine |

-continued

| Ex. No. | Structure | Name |
|---|---|---|
| 109 | 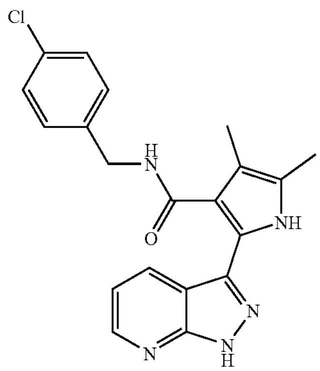 | N-(4-chlorobenzyl)-4,5-dimethyl-2-(1H-pyrazolo[3,4-b]pyridin-3-yl)-1H-pyrrole-3-carboxamide |
| 110 | 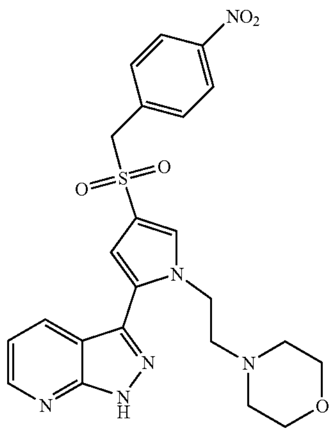 | 3-{1-(2-morpholin-4-ylethyl)-4-[(4-nitrobenzyl)sulfonyl]-1H-pyrrol-2-yl}-1H-pyrazolo[3,4-b]pyridine |

In a second aspect, this inventions is directed to a pharmaceutical composition comprising one or more compounds of formula (I) or a pharmaceutically acceptable salt thereof and a pharmaceutically acceptable excipient.

Biochemistry

Another aspect of this invention relates to a method for the modulation of the catalytic activity of a PK by contacting a PK with a compound of this invention or a pharmaceutically acceptable salt thereof.

A further aspect of this invention is that the modulation of the catalytic activity of PKs using a compound of this invention may be carried out in vitro or in vivo.

A still further aspect of this invention is that the protein kinase whose catalytic activity is being modulated by a compound of this invention is selected from the group consisting of receptor protein tyrosine kinases, cellular tyrosine kinases and serine-threonine kinases.

It is an aspect of this invention that the receptor tyrosine protein kinase whose catalytic activity is modulated by a compound of this invention is advantageously selected from the group consisting of C-Kit, C-fms, Flk-1R, Flk4, KDR/Flk-1, Flt-1, FGFR-1R, FGFR-2R, FGFR-3R, FGFR-4R, MET, DDR-1 and DDR-2.

In addition, it is an aspect of this invention that the cellular tyrosine kinase whose catalytic activity is modulated by a compound of this invention is advantageously selected from the group consisting of Src, Frk, Btk, Csk, Abl, ZAP70, Fes/Fps, Fak, Jak, Ack, Yes, Fyn, Lyn, Lck, Blk, Hck, Fgr and Yrk.

Another aspect of this invention is that the serine-threonine protein kinase whose catalytic activity is modulated by a compound of this invention is advantageously selected from the group consisting of PAK, ZC, CDK2, Raf, NEK and BUB1.

Another aspect of this inventions relates to a method for treating or preventing a protein kinase related disorder in an organism comprising administering a therapeutically effective amount of a compound or a salt thereof of Formula 1 to an organism.

It is an aspect of this invention that the above-referenced protein kinase related disorder is selected from the group consisting of a receptor protein tyrosine kinase related disorder, a cellular tyrosine kinase disorder and a serine-threonine kinase related disorder.

In yet another aspect of this invention, the above referenced protein kinase related disorder is selected from the group consisting of a Ste 20 related disorder, a Met related disorder, a PDGFR related disorder, an IGFR related disorder and a flk related disorder.

The above referenced protein kinase related disorders include by way of example and not limitation, cancers such as lung cancer, NSCLC (non small cell lung cancer), small cell lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, laryngeal cancer, cancer of the small intestine, cancer of the endocrine system (e.g., cancer of the thyroid, parathyroid or adrenal glands), sarcomas of soft tissues, cancer of the urethra, cancer of the penis, prostate cancer, testicular cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem glioma or pituitary adenomas), Barrett's esophagus (pre-malignant syndrome), neoplastic cutaneous disease, psoriasis, mycoses fungoides and benign prostatic hypertrophy, diabetes related diseases such as diabetic retinopathy, retinal ischemia and retinal neovascularization, hepatic cirrhosis, cardiovascular disease such as atherosclerosis, immunological disease such as autoimmune disease (e.g., AIDS and lupus) and renal disease. In a specific embodiment, the disease is pancreatic cancer, breast cancer, lung cancer, laryngeal cancer, ovarian cancer, uterine cancer, skin cancer, prostate cancer, kidney cancer, colon cancer and testicular cancer. In addition to primary cancers, the compounds of the present invention may be useful in treating mestastasis.

The above referenced protein kinase related disorder also includes disorders selected from the group consisting of diabetes, a hyper-proliferation disorder, hyperproliferative disorders of the kidney, von Hippel-Lindau disease, restenosis, fibrosis, psoriasis, osteoarthritis, rheumatoid arthritis, an inflammatory disorder and angiogenesis, in yet another aspect of this invention.

It is an aspect of this invention that the protein kinase related disorder being treated or prevented by administration of a compound of this invention is a PAK or ZC related disorder.

The organism in which the protein kinase related disorder is being treated or prevented is a human being, in yet another aspect of this invention.

It is an aspect of this invention that a chemical compound that modulates the catalytic activity of a protein kinase may be identified by contacting cells expressing said protein kinase with a compound or a salt thereof of Formula I and then monitoring said cells for an effect.

The above-referenced effect is selected from a change or an absence of change in a cell phenotype, a change or absence of change in the catalytic activity of said protein kinase or a change or absence of change in the interaction of said protein kinase with a natural binding partner, in another aspect of this invention.

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with antitumor agents such as, without limitation, camptosar (irinotecan HCl; U.S. Pat. No. 4,604,463).

A compound or salt of this invention might also be expected to prove efficacious in combination with an agent such as, without limitation, aromasin (exomestane; U.S. Pat. Nos. 4,808,616 and 4,904,650).

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone, paclitaxel or docetaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxy-carbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R,3R)1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R)3-[4-(4-chloro-phenoxy)-benzenesulfonylamino]-tetrahydro-pyran-3-carboxylic acid hydroxyamide; (2R,3R)1-[4-(4-fluoro-2-methyl-benzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1] octane-3-carboxylic acid hydroxyamide; 3-endo-3-[4-(4-fluoro-phenoxy)-benzenesulfonylamino]-8-oxa-bicyclo [3.2.1]octane-3-carboxylic acid hydroxyamide; and (R)3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

A compound of Formula (I) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™. (Genentech, Inc. of South San Francisco, Calif., USA). EGFR inhibitors are described, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors can also be combined with a compound of Formula (I). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compound of Formula (I) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with a compound of Formula (I), in accordance with the present invention.

A compound of Formula (I) can also be used with other agents useful in treating cancer, including, but not limited to, agents capable of enhancing antitumor immune responses, such as CTLA4 (cytotoxic lymphocite antigen 4) antibodies, and other agents capable of blocking CTLA4; and antiproliferative agents such as other farnesyl protein transferase inhibitors, for example the farnesyl protein transferase inhibitors described in the references cited in the "Background" section, of U.S. Pat. No, 6,258,824 B1. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The above method can be also be carried out in combination with radiation therapy, wherein the amount of a compound of Formula (I) administered in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

Another aspect of the invention is directed ot the use of a compound of Formula (I) in the preparation of a medicament, which is useful in the treatment of a disease mediated by abnormal Met kinase activity.

DETAILED DESCRIPTION OF THE INVENTION

Definitions

Pyridopyrazole refers to a molecule having as a portion of the chemical structure, the following:

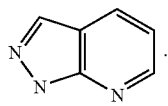

Indazole refer to a molcule having as a portion of the chemical structure, the following:

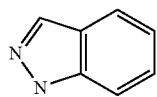

"Pyrrole" refers to a molecule having the chemical structure:

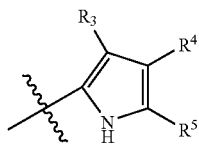

"Pharmaceutically acceptable salt" or "pharmaceutically acceptable salt thereof" refers to those salts which retain the biological effectiveness and properties of the free bases and which are obtained by reaction with inorganic or organic acids, such as hydrochloric acid, hydrobromic acid, hydroiodic acid, sulfuric acid, nitric acid, phosphoric acid, methanesulfonic acid, ethanesulfonic acid, p-toluenesulfonic acid, salicylic acid, acetic acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, and the like.

A "pharmaceutical composition" refers to a mixture of one or more of the compounds described herein, or pharmaceutically acceptable salts thereof, with other chemical components, such as pharmaceutically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives (including microcrystalline cellulose), gelatin, vegetable oils, polyethylene glycols, diluents, granulating agents, lubricants, binders, disintegrating agents, and the like.

"Alkyl" refers to a saturated aliphatic hydrocarbon including straight chain, branched chain or cyclic groups. Preferably, the alkyl group has 1 to 20 carbon atoms (whenever a numerical range; e.g., "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted with halogen, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, a heteroalicyclic ring, aryl, alkoxy, —OCZ$_3$, aryloxy, C(O)NH$_2$ or heteroaryl. R" is H, alkyl or aryl.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2–20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. The alkenyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2–20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. The alkynyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, each substituted group is preferably one or more selected halogen, hydroxy, alkoxy, aryloxy, —COR', —COOR', OCOR', —CONRR', —RNCOR', —NRR', —CN, —NO$_2$, —CZ$_3$, —OCZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine, benzofuran and carbazole. The heteroaryl group may be substituted or unsubstituted. When substituted, each substituted group is preferably one or more selected from halogen, -hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl, where Z is halogen. Wherein R and R' are defined herein.

A "heteroalicyclic ring" or "heteroalicycle" group refers to a monocyclic or fused ring group having in the ring(s) one or more atoms selected from the group consisting of nitrogen, oxygen and sulfur. The rings may also have one or more double bonds. However, the rings may not have a completely conjugated pi-electron system. The heteroalicyclic ring may be substituted or unsubstituted. The heteroalicyclic ring may contain one or more oxo groups. When substituted, the substituted group(s) is preferably one or more selected halogen, hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

Z refers to a halogen group selected from the group consisting of fluorine, chlorine, bromine and iodine.

A "hydroxy" group refers to an —OH group.

An "alkoxy" group refers to both an —O-alkyl and an —O-cycloalkyl group, as defined herein.

An "alkoxycarbonyl" refers to a —C(O)—OR.

An "aminocarbonyl" refers to a —C(O)—NRR'.

An "aryloxycarbonyl" refers to —C(O)—Oaryl.

An "aryloxy" group refers to both an —O-aryl and an —O-heteroaryl group, as defined herein.

An "arylsulfonyl" group refers to a —S(O)n-aryl, wherein n is 0–2.

An "alkylsulfonyl" group refer to a —S(O)n-alkyl, wherein n is 0–2.

A "heteroaryloxyl" group refers to a heteroaryl-O— group with heteroaryl as defined herein.

A "heteroalicycloxy" group refers to a heteroalicyclic-O— group with heteroalicyclic as defined herein.

A "carbonyl" group refers to a —C(=O)—R.

An "aldehyde" group refers to a carbonyl group where R is hydrogen.

A "thiocarbonyl" group refers to a —C(=S)—R group.

A "trihalomethanecarbonyl" group refers to a Z$_3$C—C(O)— group.

A "C-carboxyl" group refers to a —C(O)O—R groups.

An "O-carboxyl" group refers to a R—C(O)O— group.

A "carboxylic acid" group refers to a C-carboxyl group in which R is hydrogen.

A "halo" group refers to fluorine, chlorine, bromine or iodine.

A "trihalomethyl" group refers to a —CZ$_3$ group.

A "trihalomethanesulfonyl" group refers to a Z$_3$CS(O)$_2$ group.

A "trihalomethanesulfonamido" group refers to a Z$_3$CS(O)$_2$NR— group.

A "sulfinyl" group refers to a —S(O)—R group.

A "sulfonyl" group refers to a —S(O)$_2$R group.

An "S-sulfonamido" group refers to a —S(O)$_2$NRR' group.

An "N-Sulfonamido" group refers to a —NR—S(O)$_2$R group.

An "O-carbamyl" group refers to a —OC(O)NRR' group.

An "N-carbamyl" group refers to a ROC(O)NRR' group.

An "O-thiocarbamyl" group refers to a —OC(S)NRR' group.

An "N-thiocarbamyl" group refers to a ROC(S)NR'— group.

An "amino" group refers to an —NH$_2$ or an —NRR' group.

A "C-amido" group refers to a —C(O)NRR' group.

An "N-amido" group refers to a R'C(O)NR— group.

A "nitro" group refers to a —NO$_2$ group.

A "cyano" group refers to a —C≡N group.

A "silyl" group refers to a —Si(R)$_3$ group.

A "phosphonyl" group refers to a P(=O)(OR)$_2$ group.

The definitions of $R_1$–$R_9$, R, R' and R" are defined in the present specification.

Compounds that have the same molecular formula but differ in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^6$ substituent in a compound of formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

It is contemplated that a compound of Formula (I) would be metabolized by enzymes in the body of the organism such as human being to generate a metabolite that can modulate the activity of the protein kinases. Such metabolites are within the scope of the present invention.

As used herein, "PK" refers to receptor protein tyrosine kinase (RTKs), non-receptor or "cellular" tyrosine kinase (CTKs) and serine-threonine kinases (STKs).

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of RTKs, CTKs and STKs. In particular, modulating refers to the activation or inhibition of the catalytic activity of RTKs, CTKs and STKs, depending on the concentration of the compound or salt to which the RTK, CTK or STK is exposed or, preferably, the inhibition of the catalytic activity of RTKs, CTKs and STKs.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished in vitro, i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, an isolated PK may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

As used herein, the terms "prevent", "preventing" and "prevention" refer to a method for barring an organism from acquiring a PK related disorder in the first place.

As used herein, the terms "treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. For example, the catalytic activity of a PK may be observed by determining the rate or amount of phosphorylation of a target molecule.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

As used herein, "administer" or "administration" refers to the delivery of a compound or salt of the present invention or of a pharmaceutical composition containing a compound or salt of this invention to an organism for the purpose of prevention or treatment of a PK-related disorder.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts, which retain the biological effectiveness and properties of the parent compound. Such salts include:

(1) acid addition salt which is obtained by reaction of the free base of the parent compound with inorganic acids such as hydrochloric acid, hydrobromic acid, nitric acid, phosphoric acid, sulfuric acid, and perhcloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of Formula (I) may also act as a prodrug. A "prodrug" refers to an agent which bears a "prodrug group" which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), carbamate or urea. Preferred prodrug groups include, but are not limited to C(O)NRR', C(O)OR', $SO_2R$ and C(O)R' or moiety which is hydrolyzable under physiological conditions.

Indications

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction, is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, *Neuron*, 9:303–391 (1992).

It has been shown that tyrosine phosphorylation sites on growth factor receptors function as high-affinity binding sites for SH2 (src homology) domains of signaling molecules. Fantl et al., *Cell*, 69:413–423 (1992), Songyang et al., *Mol. Cell. Biol.*, 14:2777–2785 (1994), Songyang et al., *Cell*, 72:767–778 (1993), and Koch et al., *Science*, 252: 668–678 (1991). Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., *Cell*, 72:767–778 (1993). The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., *Cell*, 72:767–778 (1993). These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of the invention, in particular, the compounds generated in vivo from the compounds of the invention, inhibit PKs is not required in order to practice the present invention. However, while not hereby being bound to any particular mechanism or theory, it is believed that the compounds interact with the amino acids in the catalytic region of PKs.

In another aspect, this invention relates to a method for treating or preventing a PK related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a PK related disorder.

This invention is therefore directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders, metabolic disorders and infectious diseases.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, *J. Biological Chem.*, 267(16):10931–10934 (1992). Uncontrolled vasculogenesis and/or angiogenesis has been associated with diseases such as diabetes as well as with malignant solid tumors that rely on vascularization for growth. Klagsbum & Soker, *Current Biology*, 3(10):699–702 (1993); Folkham, *J. Natl. Cancer Inst.*, 82:4–6 (1991); Weidner, et al., *New Engl. J. Med.*, 324:1–5 (1991).

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., *Kidney International*, 43:47S–54S (1993).

STKs have been implicated in many types of cancer including, notably, breast cancer (Cance, et al., *Int. J. Cancer*, 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., *DN&P*, 7:334–339 (1994).

As noted previously, not only RTKs but CTKs including, but not limited to, src, abl, fps, yes, fyn, lyn, lck, blk, hck, fgr and yrk (reviewed by Bolen et al., *FASEB J.*, 6:3403–3409 (1992)) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v\text{-}src}$) in chicken. Moreover, its cellular homolog, the proto-oncogene $pp60^{c\text{-}src}$ transmits oncogenic signals of many receptors. Over-expression of EGFR or HER2/neu in tumors leads to the constitutive activation of $pp60^{c\text{ }src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

Finally, both RTKs and CTKs are currently suspected as being involved in hyperimmune disorders.

A method for identifying a chemical compound that modulates the catalytic activity of one or more of the above discussed protein kinases is another aspect of this invention. The method involves contacting cells expressing the desired protein kinase with a compound of this invention (or its salt) and monitoring the cells for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of the protein kinase in the cells or a change or absence of change in the interaction of the protein kinase with a natural binding partner.

Pharmaceutical Compositions and Use

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more pharmaceutically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono- di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80™, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as pharmaceutically acceptable salts wherein the claimed compound may form the negatively or the positively charged species. Examples of salts in which the compound forms the positively charged moiety include, without limitation, quaternary ammonium salts such as the hydrochloride, sulfate, carbonate, lactate, tartrate, maleate, malate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide (Ca(OH)$_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%. At present, the therapeutically effective amounts of compounds of Formula (I) may range from approximately 25 mg/m² to 150 mg/m² perday. Even more preferably 25 mg/m² to 1000 mg/m².

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

EXAMPLES

Compound Synthesis

The compounds of this invention may be readily synthesized using techniques well known in the chemical arts. It will be appreciated by those skilled in the art that other synthetic pathways for forming the compounds of the invention are available and that the following is offered by way of example and not limitation.

The following syntheses of representative compounds of this invention are shown by way of example only and are not to be construed as limiting the scope of this invention as to synthetic approach or as to the compounds whose syntheses are exemplified.

It will be clear to those skilled in the art, based both on known general principles of organic synthesis and on the disclosures herein appropriate changes and modifications to the following syntheses that may be effected without departing from the scope or spirit of the invention as defined in the appended claims.

HPLC data was obtained with a Zorbax SB C18 column (4.6 mm ID×7.5 cm), a Perkin Elmer series 200 pump programmed to run from 10% acetonitrile/water 0.1% TFA (solvent A) to 90% acetonitrile/water (solvent B) with a flow rate of 1.5 mL/min. After 0.1 min on solvent A, a 5 min linear program to solvent B was run, followed by 3 min on solvent B, before recycling to solvent A (2 min). Detection was with a Perkin Elmer diode array detector recording at 215 and 280 nM). NMR spectra were recorded on a Bruker instrument at 300 MHz.

General Synthetic Procedure

The following general methodology may be employed to prepare the compounds of this invention:

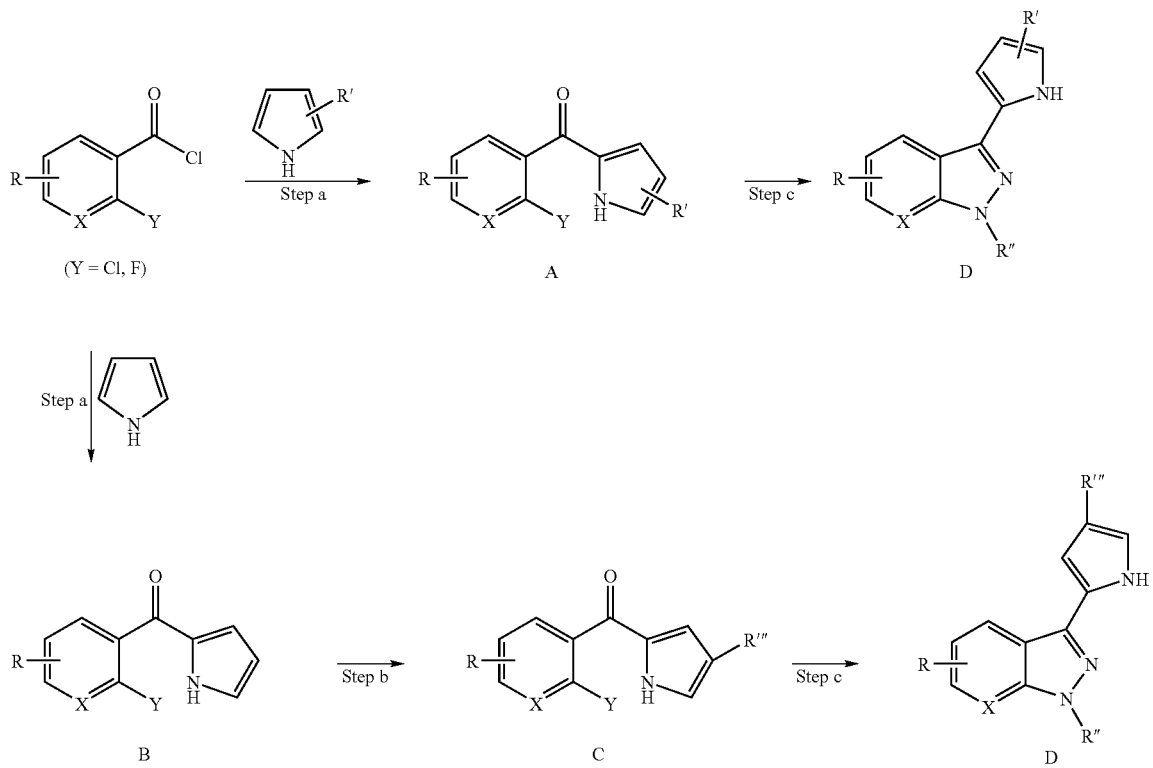

In route shown above, the intermediate diaryl ketone A or B is formed by acylation on the pyrrole ring in the presence of aluminum chloride, tin(IV)chloride or trifluoro sulfonic acid (step a). The reaction is generally carried out from 0° C. to 100° C. in benzene or dichloromethane as solvent. In step b, acylation or sulfonation at 0° C. can afford acylated or sulfonated intermediate C. An annulation of A or C with hydrazine or substituted hydrazine in methanol, ethanol, or toluene at temperatures from 20° C. to 150° C. (step c) provides 3-pyrrolyl-pyridopyrazoles and 3-pyrrolyl-indazoles D.

Example 1

3-(3,5-Dimethyl-1H-pyrrol-2-yl)-1H-pyrazolo[3,4-b]pyridine

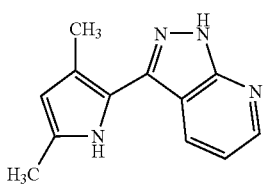

2-Chloronicotinoyl chloride (3.4 g, 20 mmol) (Aldrich, Milwaukee, Wis.) was added to a solution of aluminum chloride (2.7 g, 20 mmol) (Aldrich, Milwaukee, Wis.) in dichloromethane (100 mL) at 0° C., followed by a solution of 2,4-dimethylpyrrole (2.9 g, 30 mmol) in dichloromethane (20 mL). The mixture was then stirred at room temperature for one hour. The reaction was diluted with ethyl acetate, washed with brine, dried and concentrated. The residue was purified on a silica gel column to give 2.9 g (62%) of (2-chloro-pyridin-3-yl)-(3,5-dimethyl-1H-pyrrol-2-yl)-methanone.

A mixture of (2-chloro-pyridin-3-yl)-(3,5-dimethyl-1H-pyrrol-2-yl)-methanone (240 mg, 1 mmol) and hydrazine hydrate (0.7 mL) in ethanol (2 mL) was heated at 100–110° C. for overnight. The reaction was concentrated and purified on a silica gel column to give 97 mg (46%) of the titled compound as a light yellow solid.

$^1$HNMR (400 MHz, DMSO-d$_6$) δ 13.47 (br s, 1H, NH), 10.67 (s, 1H, NH), 8.50 (d, J=4 Hz, 1H), 8.33 (d, J=8 Hz, 1H), 7.19 (dd, 1H), 5.73 (d, J=2 Hz, 1H), 2.22 (s, 3H, CH$_3$), 2.20 (s, 3H, CH$_3$).

MS m/z 213 [M$^+$+1].

Example 2

3-(1H-Pyrrol-2-yl)-1H-pyrazolo[3,4-b]pyridine

A solution of 2-chloronicotinoyl chloride (1 eq.) in dichloromethane (10 mL) was added slowly to a mixture of pyrrole (1.5 eq.) (Aldrich, Milwaukee, Wis.) and aluminum chloride (3.5 g, 1 eq.) in dichloromethane (8 mL) at 0° C. The mixture was stirred at 0° C. for 10 mins and at room temperature for 30 mins. The reaction was diluted with ethyl acetate, washed with brine, dried and concentrated. The residue was purified on a silica gel column to give 2.27 g of (2-chloro-pyridin-3-yl)-(1H-pyrrol-2-yl)-methanone.

A mixture of (2-chloro-pyridin-3-yl)-(1H-pyrrol-2-yl)-methanone (1 g, 4.8 mmol) and hydrazine hydrate (0.5 mL) in ethanol (15 mL) was heated to reflux for overnight. The reaction was concentrated and the residue was triturated with dichloromethane (to remove any unreacted starting material. The solid was filtered, washed wit water and dried to give 720 mg (81%) of the titled compound as a light yellow solid.

$^1$HNMR (400 MHz, DMSO-d$_6$) δ 13.45 (br s, 1H, NH), 11.45 (br s, 1H, NH), 8.52 (dd, 1H), 8.50 (dd, 1H), 7.21 (dd, 1H), 6.87 (m, 1H), 6.77 (m, 1H), 6.18 (m, 1H).

MS m/z 185 [M$^+$+1].

Example 3

3-(5-Morpholin-4-ylmethyl-1H-pyrrol-2-yl)-1H-pyrazolo[3,4-b]pyridine

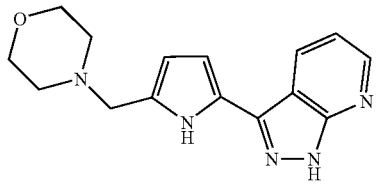

Benzyl chloroformate (150 mg) (Aldrich, Milwaukee, Wis.) was added to a mixture of 3-(1H-pyrrol-2-yl)-1H-pyrazolo[3,4-b]pyridine (120 mg) (from Example 2) and triethylamine (3 drops) in dichloromethane (DCM). After stirring at room temperature for one hour, the reaction was concentrated and purified on a silica gel column to give 3-(1H-pyrrol-2-yl)-pyrazolo[3,4-b]pyridine-1-carboxylic acid benzyl ester. It was then combined with di-morpholine methane (300 mg) (Aldrich, Milwaukee, Wis.), THF (2 mL), water (0.2 mL) and acetic acid (2 drops). The mixture was heated at 90° C. for 20 hours. The reaction was concentrated and purified on a silica gel column to give 30 mg of the titled compound as a white solid.

$^1$HNMR (400 MHz, DMSO-d$_6$) δ 13.44 (s, 1H, NH), 11.24 (s, 1H, NH), 8.50 (d, J=3 Hz, 1H), 8.45 (d, J=8 Hz, 1H), 7.19 (m, 1H), 6.68 (s, 1H), 6.02 (s, 1H), 3.54 (m, 4H), 3.48 (s, 2H, CH$_2$), 2.37 (m, 4H).

MS m/z 282 [M−1].

Example 4

3-(4-Bromo-1H-pyrrol-2-yl)-1H-pyrazolo[3,4-b]pyridine

A mixture of (2-chloro-pyridin-3-yl)-(1H-pyrrol-2-yl)-methanone (210 mg, 1 mmol) and N-bromosuccinimide (NBS) (200 mg) in THF (10 mL) was stirred at room temperature for overnight. More NBS (58 mg) was added and stirring was continued for another 5 hours until the reaction completed. The reaction was concentrated and the residue was purified on a silica gel column to give 370 mg of (4-bromo-1H-pyrrol-2-yl)-(2-chloro-phenyl)-methanone.

$^1$HNMR (400 MHz, DMSO-d$_6$) δ 12.65 (br s, 1H, NH), 8.54 (dd, 1H), 8.01 (dd, J=2 & 8 Hz, 1H), 7.54 (m, 1H), 7.45 (m, 1H), 6.63 (m, 1H).

MS m/z 283 [M−1].

A mixture of (4-bromo-1H-pyrrol-2-yl)-(2-chloro-phenyl)-methanone (250 mg) and hydrazine hydrate (6 drops) in ethanol (7 mL) was heated at 90–100° C. for overnight. The reaction was concentrated, the residue was washed with water and recrystallized from ethanol to give 78 mg of the titled compound as a off-white solid.

$^1$HNMR (400 MHz, DMSO-d$_6$) δ 13.61 (s, 1H, NH), 11.80 (br s, 1H, NH), 8.53 (s, 1H), 8.51 (m, 1H), 7.21 (m, 1H), 6.96 (m, 1H), 6.85 (m, 1H).

MS m/z 261 [M−1].

Example 5

3-(3-Phenyl-1H-pyrrol-2-yl)-1H-pyrazolo[3,4-b]pyridine

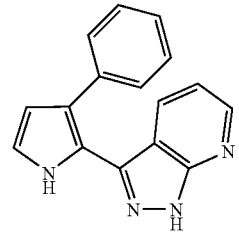

Aluminum chloride (1.33 g, 10 mmol) was added to a mixture of 3-phenyl-1H-pyrrole (1.35 g, 9.4 mmol, prepared as described in *Journal of Organic Chemistry*, 62: 2650 (1997) (incorporated herein by reference) and 2-chloronicotinoyl chloride (1.65 g, 9.4 mmol) in DCM (15 mL) at 0° C. The mixture was stirred at 0° C. for 30 mins and at room temperature for one hour. The reaction was diluted with ethyl acetate and washed with brine, 2N NaOH, brine, dried and concentrated. The residue was purified on silica gel column to give 0.682 g (26%) of (2-chloro-pyridin-3-yl)-(3-phenyl-1H-pyrrol-2-yl)-methanone.

$^1$HNMR (400 MHz, CDCl$_3$) δ 9.75 (br s, 1H, NH), 8.14 (m, 1H), 7.30 (dd, J=2 & 8 Hz, 1H), 7.26 (s, 1H), 7.20 (m, 1H), 7.04 (m, 5H), 6.81 (m, 1H), 6.36 (t, 1H).

MS m/z 283 [M$^+$+1].

A mixture of (2-chloro-pyridin-3-yl)-(3-phenyl-1H-pyrrol-2-yl)-methanone (150 mg, 0.53 mmol) from above and hydrazine hydrate (0.5 mL) in ethanol (6 mL) was heated at 90° C. for 24 hours. The reaction was concentrated, the residue was triturated with DCM, filtered to give 77 mg (56%) of the titled compound.

$^1$HNMR (400 MHz, DMSO-d$_6$) δ 13.68 (s, 1H, NH), 11.38 (br s, 1H, NH), 8.41 (dd, 1H), 7.27 (m, 2H), 7.19 (m, 3H), 7.12 (m, 1H), 6.94 (t, 1H), 6.90 (m, 1H), 6.37 (t, 1H).

MS m/z 261 [M$^+$+1].

Example 6

3-[4-(2,6-Dichloro-phenyl)-1H-pyrrol-2-yl]-1H-pyrazolo[3,4-b]pyridine

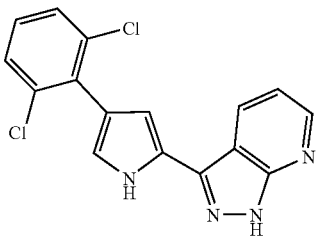

Aluminum chloride (1.4 g, 10.5 mmol) was added to a mixture of 3-(2,6-dichloro-phenyl)-1H-pyrrole (2 g, prepared as described in *Journal of Organic Chemistry*, 62: 2650 (1997) (incorporated herein by reference) and 2-chloronicotinoyl chloride (1.8 g, 10.5 mmol) in DCM (55 mL) at 0° C. The mixture was stirred at 0° C. for 30 mins and at room temperature for 1.5 hours. The reaction was diluted with ethyl acetate and washed with brine, 2N NaOH, brine, dried and concentrated. The residue was purified on silica gel column to give 168 mg of (2-chloro-pyridin-3-yl)-[4-(2,6-dichloro-phenyl)-1H-pyrrol-2-yl]-methanone.

$^1$HNMR (400 MHz, DMSO-$d_6$) δ 12.6 (br s, 1H, NH), 8.53 (dd, J=2 & 5 Hz, 1H), 8.02 (dd, J=2 & 8 Hz, 1H), 7.54 (dd, 1H), 7.51 (s, 1H), 7.49 (s, 1H), 7.45 (m, 1H), 7.31 (dd, 1H), 6.60 (m, 1H).

MS m/z 351 [M$^+$+1].

A mixture of (2-chloro-pyridin-3-yl)-[4-(2,6-dichloro-phenyl)-1H-pyrrol-2-yl]-methanone (150 mg) from above and hydrazine hydrate (0.5 mL) in ethanol (7 mL) was heated at 90–100° C. for overnight. The reaction was concentrated, the residue was washed with water, dried and triturated with ethyl acetate-hexane mixture to give 71 mg of the titled compound.

$^1$HNMR (400 MHz, DMSO-$d_6$) δ 13.55 (br s, 1H, NH), 11.75 (br s, 1H, NH), 8.52 (dd, 1H), 8.49 (dd, 1H), 7.53 (s, 1H), 7.51 (s, 1H), 7.30 (m, 1H), 7.20 (dd, 1H), 6.96 (m, 1H), 6.85 (m, 1H).

MS m/z 329 [M$^+$+1].

Example 7

3-[3-(2,6-Dichloro-phenyl)-1H-pyrrol-2-yl]-1H-pyrazolo[3,4-b]pyridine

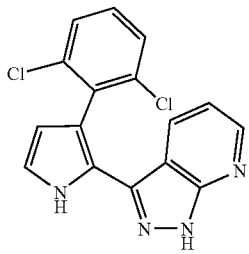

Aluminum chloride (1.4 g, 10.5 mmol) was added to a mixture of 3-(2,6-dichloro-phenyl)-1H-pyrrole (2 g, prepared according to JOC, 62, 1997, 2650) and 2-chloronicotinoyl chloride (1.8 g, 10.5 mmol) in DCM (55 mL) at 0° C. The mixture was stirred at 0° C. for 30 mins and at room temperature for 1.5 hours. The reaction was diluted with ethyl acetate and washed with brine, 2N NaOH, brine, dried and concentrated. The residue was purified on silica gel column to give 160 mg of (2-chloro-pyridin-3-yl)-[3-(2,6-dichloro-phenyl)-1H-pyrrol-2-yl]-methanone.

$^1$HNMR (400 MHz, DMSO-$d_6$) δ 12.4 (br s, 1H, NH), 8.20 (dd, 1H), 7.60 (dd, J=2 & 8 Hz, 1H), 7.36 (t, 1H), 7.26 (s, 1H), 7.24 (s, 1H), 7.13 (dd, 1H), 7.10 (dd, 1H), 6.20 (t, 1H).

MS m/z 351 [M$^+$+1].

A mixture of (2-chloro-pyridin-3-yl)-[3-(2,6-dichloro-phenyl)-1H-pyrrol-2-yl]-methanone (160 mg) and hydrazine hydrate (0.5 mL) in ethanol (8 mL) was heated at 90–100° C. for 24 hours. The reaction was concentrated, the residue was purified on a silica gel column to give 30 mg of the titled compound.

$^1$HNMR (400 MHz, DMSO-$d_6$) δ 13.54 (br s, 1H, NH), 11.55 (br s, 1H, NH), 8.39 (dd, 1H), 7.45 (d, 1H), 7.43 (s, 1H), 7.36 (dd, 1H), 7.29 (dd, 1H), 6.98 (t, 1H), 6.95 (dd, 1H), 6.15 (t, 1H).

MS m/z 329 [M$^+$+1].

Example 8

(2,6-Difluoro-phenyl)-[5-(1H-pyrazolo[3,4-b]pyridin-3-yl)-1H-pyrrol-3-yl]-methanone

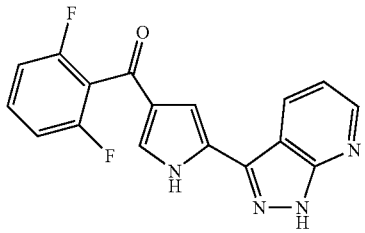

Aluminum chloride (650 mg, 4.9 mmol) was added to a mixture of (2-chloro-pyridin-3-yl)-(1H-pyrrol-2-yl)-methanone (600 mg, 3 mmol) (from Example 2) and 2-chloronicotinoyl chloride (1.2 g, 6.8 mmol) in dichloroethane (15 mL). The mixture was heated at 90–100° C. for 2 hours. The reaction was diluted with ethyl acetate, washed with brine, 1N NaOH (10 mL), dried and concentrated. The residue was purified on a silica gel column to give 340 mg of (2-chloro-pyridin-3-yl)-[4-(2,6-difluoro-benzoyl)-1H-pyrrol-2-yl]-methanone.

A mixture of (2-chloro-pyridin-3-yl)-[4-(2,6-difluoro-benzoyl)-1H-pyrrol-2-yl]-methanone (200 mg) and hydrazine hydrate (8 drops) in ethanol (4 mL) was heated at 90–100° C. for 30 hours. The reaction was concentrated, the residue was purified on a silica gel column to give 73 mg of the titled compound as a white solid.

$^1$HNMR (400 MHz, DMSO-$d_6$) δ 13.78 (br s, 1H, NH), 12.48 (br s, 1H, NH), 8.56 (m, 2H), 7.59 (m, 1H), 7.33 (m, 1H), 7.26 (t, 1H), 7.22–7.24 (m, 2H), 7.18 (m, 1H).

MS m/z 325 [M$^+$+1].

Example 9

6-Chloro-3-(1H-pyrrol-2-yl)-1H-pyrazolo[3,4-b]pyridine

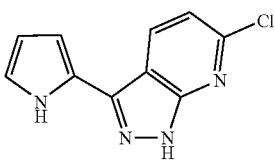

Oxalyl chloride (2M solution, 20 mL) (Aldrich, Milwaukee, Wis.) was added to a mixture of 2,6-dichloronicotinic acid (6.2 g) and N,N-dimethylformamide (DMF) (0.5 mL) in DCM (100 mL) at room temperature. After stirring at room temperature for 2 hours, the reaction was concentrated to give 2,6-dichloro-nicotinoyl chloride (used directly in the next step).

Tin (IV) chloride (Aldrich, Milwaukee, Wis.) in DCM (10 mL) was added dropwise to a mixture of pyrrole (4 g) and 2,6-dichloro-nicotinoyl chloride (6 g) in DCM (150 mL) at 0° C. The mixture was then stirred at room temperature for 30 mins. The reaction was diluted with water, washed with water (200 mL), 2N NaOH (50 mL) and brine, dried and concentrated. The residue was purified on a silica gel column to give 1.8 g of (2,6-dichloro-pyridin-3-yl)-(1H-pyrrol-2-yl)-methanone and 380 mg of (2,6-dichloro-pyridin-3-yl)-(1H-pyrrol-3-yl)-methanone.

$^1$HNMR (400 MHz, DMSO-$d_6$) δ 12.29 (br s, 1H, NH), 8.06 (d, J=8 Hz, 1H), 7.68 (d, J=8 Hz, 1H), 7.30 (m, 1H), 6.62 (m, 1H), 6.25 (m, 1H).

MS m/z 239 [M−1].

A mixture of (2,6-dichloro-pyridin-3-yl)-(1H-pyrrol-2-yl)-methanone (1.8 g) and hydrazine hydrate (0.5 mL) in ethanol (70 mL) was heated at 90° C. for 20 hours. The reaction was concentrated to 40 mL, diluted with water (5 mL) and cooled. The precipitate was collected and dried to give 0.84 g of the titled compound.

MS m/z 219 [M$^+$+1].

Example 10

6-Chloro-3-(1H-pyrrol-3-yl)-1H-pyrazolo[3,4-b]pyridine

Titanium (IV) chloride in DCM (10 mL) was added dropwise to a mixture of pyrrole (4 g) and 2,6-dichloro-nicotinoyl chloride (6 g) in DCM (150 mL) at 0° C. The mixture was then stirred at room temperature for 30 mins. The reaction was diluted with water, washed with water (200 mL), 2N NaOH (50 mL) and brine, dried and concentrated. The residue was purified on a silica gel column to give 1.8 g of (2,6-dichloro-pyridin-3-yl)-(1H-pyrrol-2-yl)-methanone and 380 mg of (2,6-dichloro-pyridin-3-yl)-(1H-pyrrol-3-yl)-methanone.

$^1$HNMR (400 MHz, DMSO-$d_6$) δ 11.74 (br s, 1H, NH), 7.99 (d, J=8 Hz, 1H), 7.65 (d, J=8 Hz, 1H), 7.31 (m, 1H), 6.92 (m, 1H), 6.50 (m, 1H).

MS m/z 239 [M−1].

A mixture of (2,6-dichloro-pyridin-3-yl)-(1H-pyrrol-3-yl)-methanone (300 mg) and hydrazine hydrate (0.2 mL) in ethanol (10 mL) was heated at 90° C. for 20 hours. The reaction was concentrated to 6 mL, diluted with water (2 mL) and cooled. The precipitate was collected and dried to give 160 mg of the titled compound.

MS m/z 219 [M$^+$+1].

Example 11

5-(1H-Pyrazolo[3,4-b]pyridin-3-yl)-1H-pyrrole-3-carboxylic acid ethyl ester

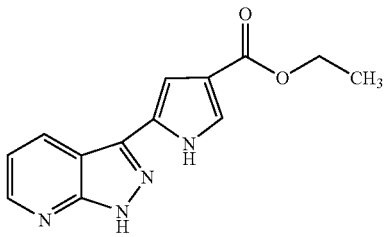

Ethanol (3.2 mL, 54 mmol) and 4-dimethylamino pyridine (DMAP) (54 mg, 0.45 mmol) were added to a mixture of pyrrole-3-carboxylic acid (500 mg, 4.5 mmol) and dicyclohexylcarbodiimide (1.11 g, 5.4 mmol) (Aldrich, Milwaukee, Wis.) in tetrahydrofuran (THF) (15 mL). After heating at 60° C. for 10 hours, the reaction was cooled. The precipitate was filtered off, washed with ethyl acetate, the combined filtrate was concentrated and purified on a silica gel column to give 500 mg (81%) of 1H-pyrrole-3-carboxylic acid ethyl ester as a colorless oil.

$^1$HNMR (400 MHz, DMSO-$d_6$) δ 11.40 (br s, 1H, NH), 7.37 (s, 1H), 6.78 (s, 1H), 6.38 (s, 1H), 4.13 (q, J=7 Hz, 2H), 1.22 (t, J=7 Hz, 3H).

Ms m/z 138 [M−1].

A solution of 2-chloronicotinoyl chloride (493 mg, 2.8 mmol) in benzene (1 mL) was added to a mixture of 1H-pyrrole-3-carboxylic acid ethyl ester (390 mg, 2.8 mmol) in benzene (3 mL), followed by a dropwise addition of tin (IV) chloride (0.5 mL). The mixture was stirred at room temperature under nitrogen for overnight. The reaction was treated with 2N HCl and extracted with ethyl acetate. The combined ethyl acetate was washed, dried and concentrated to give 390 mg (50%) of 5-(2-chloro-pyridine-3-carbonyl)-1H-pyrrole-3-carboxylic acid ethyl ester as a white solid.

$^1$HNMR (400 MHz, DMSO-$d_6$) δ 12.92 (br s, 1H, NH), 8.57 (s, 1H), 8.05 (d, 1H), 7.80 (s, 1H), 7.57 (m, 1H), 6.78 (s, 1H), 4.16 (q, J=7 Hz, 2H), 1.21 (t, J=7 Hz, 3H).

MS m/z 279 [M$^+$+1].

A mixture of 5-(2-chloro-pyridine-3-carbonyl)-1H-pyrrole-3-carboxylic acid ethyl ester (1.2 g, 4.32 mmol) and hydrazine hydrate (6.27 mL) in ethanol (50 mL) was heated at 80° C. for 24 hours. The reaction was concentrated and the residue was neutralized to pH 7 with 1N HCl, extracted with ethyl acetate. The combined ethyl acetate was dried, concentrated and purified on a silica gel column to give the titled compound as a white solid.

$^1$HNMR (400 MHz, DMSO-$d_6$) δ 13.70 (s, 1H, NH), 12.16 (br s, 1H, NH), 8.52 (m, 2H), 7.46 (s, 1H), 7.21 (m, 1H), 7.04 (s, 1H), 4.2 (q, 2H), 1.28 (t, 3H).

MS m/z 257 [M$^+$+1].

Example 12

5-(1H-Pyrazolo[3,4-b]pyridin-3-yl)-1H-pyrrole-3-carboxylic acid

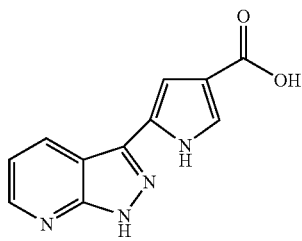

A mixture of 5-(1H-pyrazolo[3,4-b]pyridin-3-yl)-1H-pyrrole-3-carboxylic acid ethyl ester (200 mg, 0.78 mmol) (from Example 11) and 10% NaOH (10 mL) was stirred at room temperature for one hour, at 40° C. for 2 hours and at room temperature for overnight. The reaction was adjusted to pH 6–7 with concentrated HCl. The precipitate was collected by vacuum filtration, washed with water and dried to give 140 mg (79%) of the titled compound.

$^1$HNMR (400 MHz, DMSO-$d_6$) δ 13.64 (s, 1H, NH), 12.16 (br s, 1H, NH), 11.84 (br s, 1H, COOH), 8.52 (m, 2H), 7.39 (m, 1H), 7.23 (m, 1H), 7.04 (m, 1H).

MS m/z 227 [M$^+$+1].

Example 13

5-(1H-Pyrazolo[3,4-b]pyridin-3-yl)-1H-pyrrole-3-carboxylic acid (2-morpholin-4-yl-ethyl)-amide

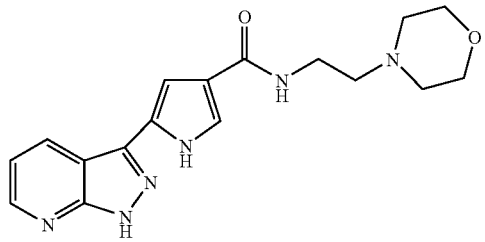

Triethylamine (0.073 mL) was added to a mixture of 5-(1H-pyrazolo[3,4-b]pyridin-3-yl)-1H-pyrrole-3-carboxylic acid (100 mg, 0.44 mmol) (from Example 12) and 4-(2-aminoethyl)morpholine (62.8 mg, 1.1 eq.) (Aldrich, Milwaukee, Wis.) in acetonitrile (1 mL) and DMF (1 mL). The mixture was cooled in an ice bath and to it was added diethyl cyanophosphonate (86 mg, 1.2 eq.). The mixture was allowed to warm up slowly to room temperature and stirred for overnight. The reaction was diluted with DCM, washed with NaHCO$_3$ and water, dried and concentrated. The residue was purified on a silica gel column to give the titled compound.

$^1$HNMR (400 MHz, DMSO-$d_6$) δ 13.59 (s, 1H, NH), 11.82 (br s, 1H, NH), 8.54 (m, 1H), 8.47 (d, J=8 Hz, 1H), 7.84 (br s, 1H, NH), 7.35 (s, 1H), 7.26 (m, 1H), 7.19 (s, 1H), 3.56 (m, 4H), 2.87 (s, 2H), 2.71 (s, 2H), 2.41 (m, 4H).

MS m/z 341 [M$^+$+1].

Example 14

5-(1H-Pyrazolo[3,4-b]pyridin-3-yl)-1H-pyrrole-3-carboxylic acid amide

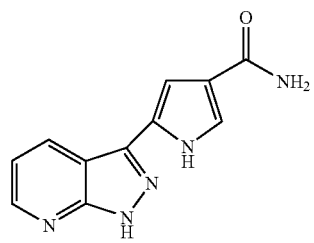

To a mixture of 5-(1H-pyrazolo[3,4-b]pyridin-3-yl)-1H-pyrrole-3-carboxylic acid (80 mg, 0.35 mmol) (from Example 11) and fluoro-N,N,N',N'-tetramethylformamidinium hexafluorophosphate (92.7 mg, 0.35 mmol) (Aldrich, Milwaukee, Wis.) in acetonitrile (6 mL) at 0° C. was added N,N-diisopropylethylamine (DIPEA) (54.28 mg, 0.42 mmol). The mixture was allowed to warm up to room temperature and stirred for one hour. The mixture was then cooled in an ice-bath and charged with ammonia gas. After stirring at room temperature for overnight, the reaction was concentrated, diluted with water and extracted with DCM. The organic layer was concentrated and triturated with DCM to give the titled compound.

$^1$HNMR (400 MHz, DMSO-$d_6$) δ 13.58 (s, 1H, NH), 11.80 (br s, 1H, NH), 8.52 (m, 1H), 8.48 (d, 1H), 7.36 (m, 1H), 7.26 (m, 1H), 7.18 (s, 1H), 2.86 (s, 2H, NH$_2$).

MS m/z 228 [M$^+$+1].

Example 15

5-(1H-Pyrazolo[3,4-b]pyridin-3-yl)-1H-pyrrole-3-carboxylic acid benzylamide

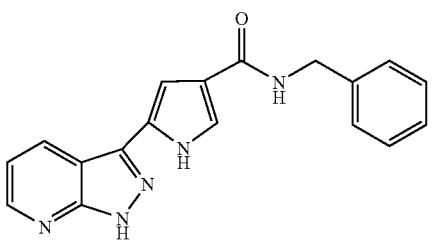

A mixture of 5-(1H-pyrazolo[3,4-b]pyridin-3-yl)-1H-pyrrole-3-carboxylic acid (50 mg, 0.22 mmol) (from example 11), p-hydroxybenzotriazole hydrate (HOBt) (74 mg, 2.5 eq.), 1-(3-dimethylaminopropyl)-3-ethyl carbodiimide hydrochloride (EDAC HCl) (105 mg, 2.5 eq.), benzylamine (94 mg, 4 eq.) and triethylamine (TEA) (0.5 mL) in DMF (1 mL) was heated at 40° C. for overnight. The reaction was concentrated and the residue was purified on a silica gel column to give 40 mg of the titled compound as a white solid.

$^1$HNMR (400 MHz, DMSO-$d_6$) δ 8.4–8.55 (m, 3H), 7.39 (m, 1H), 7.2–7.3 (m, 6H), 4.43 (d, 2H, CH$_2$).

Example 16

5-(1H-Pyrazolo[3,4-b]pyridin-3-yl)-1H-pyrrole-3-carboxylic acid isobutyl-amide

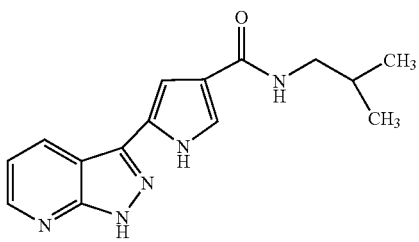

A mixture of 5-(1H-pyrazolo[3,4-b]pyridin-3-yl)-1H-pyrrole-3-carboxylic acid (100 mg, 0.44 mmol) (from Example 11) and thionyl chloride (2M in DCM, 5 mL) was heated to reflux for 2 hours. The reaction was concentrated, the residue was then stirred with isobutyl amine (excess) in DCM at room temperature for 2 hours. The reaction was diluted with DCM, washed with water, dried and concentrated. The residue was purified on a silica gel column to give the titled compound as a white solid.

$^1$HNMR (400 MHz, DMSO-d$_6$) δ 13.57 (s, 1H, NH), 11.8 (br s, 1H, NH), 8.52 (m, 1H), 8.48 (d, J=8 Hz, 1H), 7.83 (m, 1H), 7.35 (m, 1H), 7.24 (m, 2H), 3.0 (m, 2H, CH$_2$), 1.78 (m, 1H, CH), 0.87 (J=6 Hz, 6H, 2×CH$_3$).

Example 17

5-(1H-Pyrazolo[3,4-b]pyridin-3-yl)-1H-pyrrole-3-sulfonic acid (2-morpholin-4-yl-ethyl)-amide

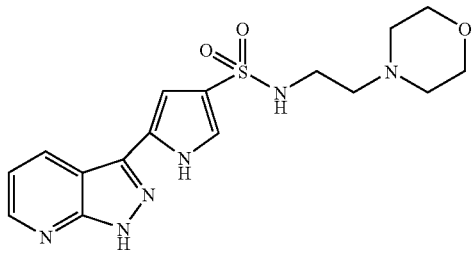

Chlorosulfonic acid (6.6 mL, 100 mL) was added dropwise to (2-chloro-pyridin-3-yl)-(1H-pyrrol-2-yl)-methanone (from Example 2, 2.06 g, 10 mmol) at 0° C. After stirring at 0° C. for 24 hours, the reaction was poured slowly into ice water. The precipitate was collected by vacuum filtration, washed with water and dried to give 2.9 g (95%) of 5-(2-chloro-pyridine-3-carbonyl)-1H-pyrrole-3-sulfonyl chloride as a white solid.

To a solution of 5-(2-chloro-pyridine-3-carbonyl)-1H-pyrrole-3-sulfonyl chloride (500 mg, 1.64 mmol) in DCM (5 mL) was added 4-(2-aminoethyl)morpholine (427 mg, 3.28 mmol) and triethylamine (0.5 mL). The mixture was stirred at room temperature for 4 hours. The reaction was extracted with DCM, the combined DCM was washed with water and brine, dried and concentrated. The residue was purified on a silica gel column to give 450 mg (69%) of 5-(2-chloro-pyridine-3-carbonyl)-1H-pyrrole-3-sulfonic acid (2-morpholin-4-yl-ethyl)-amide as a white solid.

A mixture of 5-(2-chloro-pyridine-3-carbonyl)-1H-pyrrole-3-sulfonic acid (2-morpholin-4-yl-ethyl)-amide (100 mg) and hydrazine hydrate (excess) in ethanol (5 mL) was heated at 80° C. for 48 hours. The reaction was concentrated, diluted with water, acidified to pH 2 with 1N HCl and extracted with DCM. The aqueous layer was adjusted to pH 7 with NaHCO$_3$, the precipitate was collected by vacuum filtration, washed with water to give the titled compound as a white solid.

$^1$HNMR (400 MHz, DMSO-d$_6$) δ 13.74 (s, 1H, NH), 12.22 (br s, 1H, NH), 8.56 (m, 1H), 8.48 (d, 1H), 7.32 (m, 1H), 7.24 (m, 1H), 7.0 (s, 1H), 6.92 (m, 1H, NH), 3.48 (m, 4H), 2.9 (m, 2H), 2.32 (m, 2H), 2.22 (m, 4H).

Example 18

5-(1H-Pyrazolo[3,4-b]pyridin-3-yl)-1H-pyrrole-3-sulfonic acid benzylamide

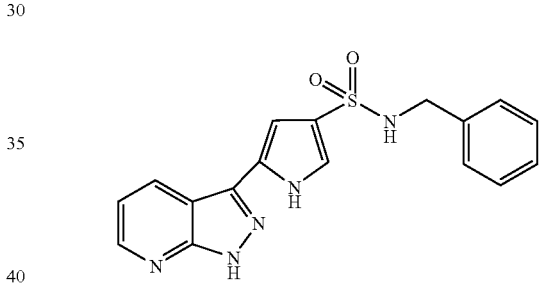

A mixture of 5-(2-chloro-pyridine-3-carbonyl)-1H-pyrrole-3-sulfonyl chloride (500 mg, 1.64 mmol) (from Example 17), benzylamine (351.5 mg, 3.28 mmol) and triethylamine (1 mL) in DCM (5 mL) was stirred at room temperature for 4 hours. The reaction was diluted with DCM, washed with water, dried and concentrated. The residue was purified on a silica gel column to give 5-(2-chloro-pyridine-3-carbonyl)1H-pyrrole-3-sulfonic acid benzylamide.

$^1$HNMR (400 MHz, DMSO-d$_6$) δ 12.98 (br s, 1H, NH), 8.6 (m, 1H), 8.15 (m, 1H), 7.8 (m, 1H, NH), 7.65 (s, 1H), 7.6 (m, 1H), 7.22 (m, 5H), 6.65 (s, 1H), 3.85 (m, 2H, CH$_2$).

A mixture of 5-(2-chloro-pyridine-3-carbonyl)-1H-pyrrole-3-sulfonic acid benzylamide (100 mg), hydrazine hydrate (excess) in ethanol (10 mL) was heated at 80° C. for 48 hours. The reaction was concentrated, mixed with water, the precipitate was filtered off, the filtrate was washed with dilute HCl, water, dried and concentrated to give the titled compound as a light yellow solid.

$^1$HNMR (400 MHz, DMSO-d$_6$) δ 13.74 (s, 1H, NH), 12.22 (br s, 1H, NH), 8.56 (m, 1H), 8.46 (d, 1H), 7.62 (m, 1H, NH), 7.25 (m, 7H), 7.0 (s, 1H), 4.02 (m, 2H, CH$_2$).

Example 19

5-(1H-Pyrazolo[3,4-b]pyridin-3-yl)-1H-pyrrole-3-carboxylic acid carbamoylmethyl-amide

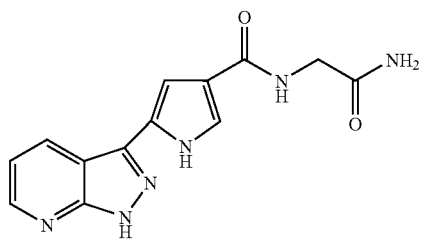

A mixture of 5-(1H-pyrazolo[3,4-b]pyridin-3-yl)-1H-pyrrole-3-carboxylic acid (100 mg, 0.43 mmol) (from Example 11) and thionyl chloride (0.2M in DCM, 10 mL) was heated to reflux for 2 hours. The reaction was concentrated, the residue was dissolved in DCM, to it was added glycinamide hydrochloride (242 mg, 2.19 mmol), followed by TEA. The mixture was then stirred at room temperature until the reaction was completed by TLC. The reaction was diluted with water and extracted with DCM. The combined DCM was concentrated and purified on a silica gel column to give the titled compound.

MS m/z 284 [M$^+$+1].

Example 20

5-(1H-Pyrazolo[3,4-b]pyridin-3-yl)-1H-pyrrole-3-carboxylic acid phenethyl-amide

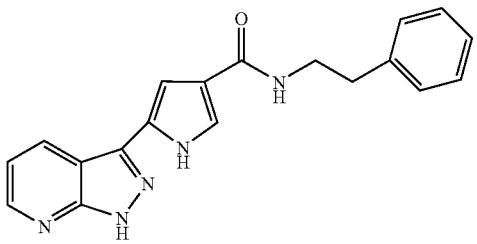

A mixture of 5-(1H-pyrazolo[3,4-b]pyridin-3-yl)-1H-pyrrole-3-carboxylic acid (50 mg, 0.22 mmol) (from Example 11), HOBt (74 mg, 2.5 eq.), EDAC (105 mg, 2.5 eq.), phenethylamine (106 mg, 4 eq.) and TEA (0.5 mL) in DMF (1 mL) was heated at 40° C. for overnight. The reaction was concentrated and purified on a silica gel column to give the titled compound as a white solid.

$^1$HNMR (400 MHz, DMSO-$d_6$) δ 13.60 (s, 1H, NH), 11.81 (brs, 1H, NH), 8.52 (m, 1H), 8.46 (m, 1H), 7.98 (m, 1H), 7.8 (br s, 1H, NH), 7.18–7.34 (m, 7H), 3.4 (m, 2H), 3.0 (m, 2H).

MS m/z 332 [M$^+$+1].

Example 21

5-(1H-Pyrazolo[3,4-b]pyridin-3-yl)-1H-pyrrole-3-carboxylic acid phenylamide

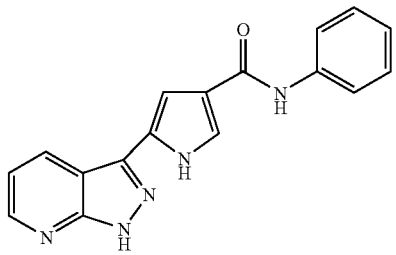

Thionyl chloride (0.2 M in DCM, 10 mL) was added to 5-(1H-pyrazolo[3,4-b]pyridin-3-yl)-1H-pyrrole-3-carboxylic acid (100 mg) (from Example 11) and the mixture was heated to reflux for 4 hours. The reaction was concentrated, diluted with DCM, mixed with aniline (excess), DMAP (cat. amount) and triethylamine. After stirring at room temperature for overnight, the reaction was quenched with water, extracted with DCM and concentrated. The residue was purified on a silica gel column to give the titled compound as a white solid.

$^1$HNMR (400 MHz, DMSO-$d_6$) δ 13.66 (s, 1H, NH), 12.02 (br s, 1H, NH), 9.6 (s, 1H), 8.55 (m, 2H), 7.77 (d, 2H), 7.62 (s, 1H), 7.38 (s, 1H), 7.3 (m, 3H), 7.04 (t, 1H, NH).

Example 22

5-Nitro-3-(1H-pyrrol-2-yl)-1H-indazole

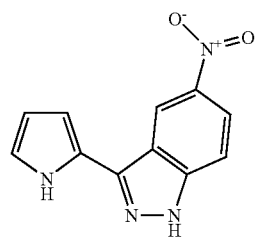

Aluminum chloride (2.6 g, 20 mmol) was added to a mixture of 2-chloro-5-nitro-benzoyl chloride (5 g, 20 mmol) and pyrrole (4 g, 30 mmol) in DCM (100 mL) at 0° C. The mixture was stirred at 0° C. for 30 mins. The reaction was diluted with ethyl acetate, washed with brine, water, NaHCO$_3$, dried and concentrated. The residue was purified on a silica gel column to give 1.5 g (30%) of (2-chloro-5-nitro-phenyl)-(1H-pyrrol-2-yl)-methanone.

A mixture of (2-chloro-5-nitro-phenyl)-(1H-pyrrol-2-yl)-methanone (600 mg) and hydrazine hydrate (0.5 mL) in toluene (20 mL) and DMF (3 mL) was heated at 120° C. for 2 hours. The reaction was concentrated, the residue was washed with water and recrystallized to give 0.42 g (77%) of the titled compound as an orange solid.

$^1$HNMR (400 MHz, DMSO-$d_6$) δ 13.62 (s, 1H, NH), 11.57 (br s, 1H, NH), 8.89 (d, J=2 Hz, 1H), 8.20 (dd, J=2 & 9 Hz, 1H), 7.69 (d, J=9 Hz, 1H), 6.91 (m, 1H), 6.81 (m, 1H), 6.22 (m, 1H).

MS m/z 227 [M−1].

Example 23

3-(1H-Pyrrol-2-yl)-1H-indazol-5-ylamine

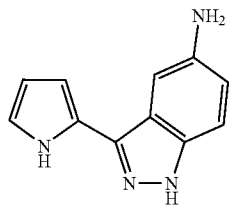

5-Nitro-3-(1H-pyrrol-2-yl)-1H-indazole (37 mg) (from Example 22) was hydrogenated using 5% Pd/C (20 mg) in ethanol (5 mL) for 2 hours. The reaction was filtered and the filtrate was concentrated to give 20 mg of the titled compound.

MS m/z 199 [M$^+$+1].

Example 24

N-[3-(1H-Pyrrol-2-yl)-1H-indazol-5-yl]-isonicotinamide

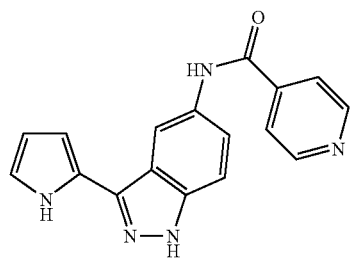

2,2-Dimethyl-propionic acid 5-nitro-3-(1H-pyrrol-2-yl)-indazol-1-yl ester (370 mg, 1.13 mmol) (from Example 28) was hydrogenated using 10% Pd/C in ethanol (35 mL) at room temperature for 2 hours. The reaction was filtered and the filtrate was concentrated to give 2,2-dimethyl-propionic acid 5-amino-3-(1H-pyrrol-2-yl)-indazol-1-yl ester.

2,2-Dimethyl-propionic acid 5-amino-3-(1H-pyrrol-2-yl)-indazol-1-yl ester (0.38 mmol) was coupled with isonicotinoyl chloride (0.4 mmol) (Aldrich, Milwaukee, Wis.) and triethylamine in DCM at 0° C. to give 120 mg of the titled compound as a light yellow solid.

MS m/z 304 [M$^+$+1].

Example 25

3-Chloro-N-[3-(1H-pyrrol-2-yl)-1H-indazol-5-yl]-benzamide

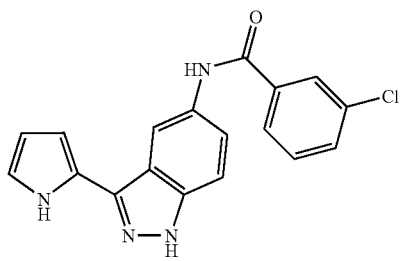

2,2-Dimethyl-propionic acid 5-amino-3-(1H-pyrrol-2-yl)-indazol-1-yl ester (0.38 mmol) (From Example 28) was coupled with 3-chloro-benzoyl chloride (0.4 mmol) and triethylamine in DCM at 0° C. to give 41 mg of the titled compound as a white solid.

MS m/z 337 [M$^+$+1].

Example 26

4-Methoxy-N-[3-(1H-pyrrol-2-yl)-1H-indazol-5-yl]-benzamide

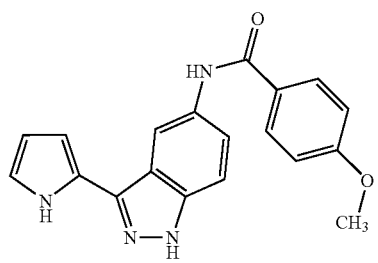

2,2-Dimethyl-propionic acid 5-amino-3-(1H-pyrrol-2-yl)-indazol-1-yl ester (0.38 mmol) (from Example 25) was coupled with 4-methoxy-benzoyl chloride (0.4 mmol) and triethylamine in DCM at 0° C. to give 130 mg of the titled compound as a white solid.

MS m/z 333 [M$^+$+1].

Example 27

1-Methyl-5-nitro-3-(1H-pyrrol-2-yl)-1H-indazole

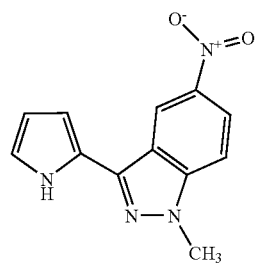

A mixture of (2-chloro-5-nitro-phenyl)-(1H-pyrrol-2-yl)-methanone (110 mg) (from Example 22) and methylhydrazine (3 drops) in toluene (2 mL) and 1-methyl-2-pyrrolidinone (1 mL) was heated at 100–120° C. for 2 hours. The reaction was concentrated, diluted with ethyl acetate (50 mL), washed with brine and concentrated. The residue was purified on a silica gel column to give 145 mg of the titled compound as yellow solid.

MS m/z 241 [M−1].

Example 28

5-Nitro-3-(1H-pyrrol-2-yl)-indazole-1-carboxylic acid tert-butyl ester

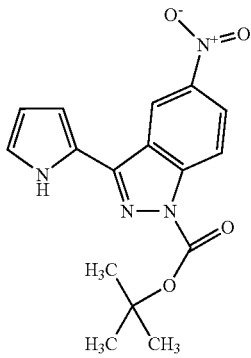

A mixture of 5-nitro-3-(1H-pyrrol-2-yl)-1H-indazole (400 mg, 1.7 mmol), di-tert-butyl-dicarbonate (0.5 g) and triethylamine (0.2 mL) in ethyl acetate-DCM was stirred at room temperature for overnight. The reaction was washed with brine, concentrated and triturated with ethyl acetate-hexane to give 450 mg of 2,2-dimethyl-propionic acid 5-nitro-3-(1H-pyrrol-2-yl)-indazol-1-yl ester as a yellow solid.

MS m/z 327 [M−1].

Example 29

3-(4-Bromo-1H-pyrrol-2-yl)-5-nitro-1H-indazole

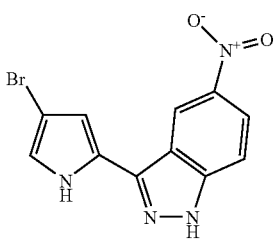

A mixture of (2-chloro-5-nitro-phenyl)-(1H-pyrrol-2-yl)-methanone (600 mg, 2.4 mmol) (from Aldrich, Milwaukee, Wis.) and NBS (504 mg, 2.8 mmol) in THF (60 mL) was stirred at room temperature for overnight. The reaction was concentrated, diluted with ethyl acetate (100 mL), washed wit 1N NaOH, brine and concentrated. The residue was recrystallized to give 310 mg (39%) of (4-bromo-1H-pyrrol-2-yl)-(2-chloro-5-nitro-phenyl)-methanone.

$^1$HNMR (400 MHz, DMSO-$d_6$) δ 12.70 (br s, 1H, NH), 8.35 (m, 2H), 7.87 (d, J=9 Hz, 1H), 7.48 (m, 1H), 6.74 (m, 1H).

MS m/z 329 [M−1].

A mixture of (4-bromo-1H-pyrrol-2-yl)-(2-chloro-5-nitro-phenyl)-methanone (400 mg) and hydrazine hydrate (0.4 mL) in toluene (6 mL) and 1-methyl-2-pyrrolidinone (1.5 mL) was heated at 110° C. for 1 hour. The reaction was concentrated, the residue was triturated with 10% ethyl acetate in DCM to give 210 mg of the titled compound as an orange solid.

$^1$HNMR (400 MHz, DMSO-$d_6$) δ 13.72 (br s, 1H, NH), 11.92 (br s, 1H, NH), 8.92 (d, 1H), 8.21 (dd, J=2 & 9 Hz, 1H), 7.21 (d, J=9 Hz, 1H), 7.04 (m, 1H), 6.93 (m, 1H).

MS m/z 307 [M−1].

Example 30

5-(1H-Pyrazolo[3,4-b]pyridin-3-yl)-1H-pyrrole-2-carboxylic acid

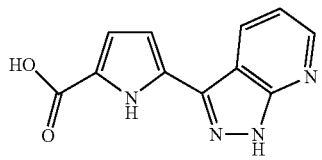

A solution of tin (IV) chloride (3.72 g, 5 mmol) in benzene (10 mL) was added dropwise to a mixture of 2-chloronicotinoyl chloride (2.02 g, 11 mmol) and 1H-pyrrole-2-carboxylic acid ethyl ester (0.73 g; prepared as discussed below) in dry benzene (12 mL) at 0° C. The reaction was allowed to warm up slowly to room temperature and stirred 4 hours. The reaction was concentrated, the residue was dissolved in ethyl acetate and washed with brine, dried and concentrated to give 1.53 g of 5-(2-chloro-pyridine-3-carbonyl)-1H-pyrrole-2-carboxylic acid ethyl ester as a brown solid.

1H-pyrrole-2-carboxylic acid ethyl ester was prepared as follows: to a solution of 1H-pyrrole-2-carboxylic acid (10 mmol; Aldrich, Milwaukee, Wis.) in DCM (15 mL) was added oxalyl chloride (10 mmol) and 3 drops of DMF at 0° C. The solution was stirred at 0° C. for 30 minutes to form 1H-pyrrole-2-carbonyl chloride. Ethanol was added and the mixture was stirred at room temperature for 30 minutes. The mixture was concetrated to afford 1-carboxylic acid ethyl ester.

A mixture of 5-(2-chloro-pyridine-3-carbonyl)-1H-pyrrole-2-carboxylic acid ethyl ester (0.5 g) and hydrazine hydrate (0.7 g) in ethanol was heated at 80° C. for 24 hours. The resulted precipitate was collected by vacuum filtration, washed with water and dried to give 80 mg of the titled compound.

MS m/z 227 [M−1].

Example 31

5-(1H-Pyrazolo[3,4-b]pyridin-3-yl)-1H-pyrrole-2-carboxylic acid ethyl ester

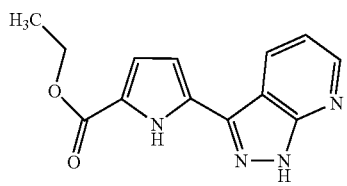

A mixture of 5-(2-chloro-pyridine-3-carbonyl)-1H-pyrrole-2-carboxylic acid ethyl ester (0.5 g) (from Example 30) and hydrazine hydrate (0.7 g) in ethanol was heated at 80° C. for 24 hours. The precipitate was filtered off and the filtrate was concentrated to give 156 mg of the titled compound.

$^1$HNMR (400 MHz, DMSO-$d_6$) δ 13.78 (s, 1H, NH), 12.10 (s, 1H, NH), 8.56 (s, 1H), 8.48 (d, 1H), 7.24 (m, 1H), 6.92 (s, 1H), 6.8 (s, 1H), 4.22 (q, 2H), 1.28 (t, 3H).

Example 32

5-(1H-Pyrazolo[3,4-b]pyridin-3-yl)-1H-pyrrole-2-carboxylic acid methylamide

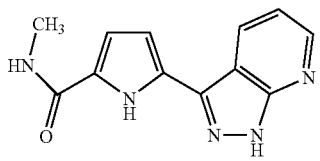

To a solution of 1H-pyrrole-2-carboxylic acid (1 g, 9 mmol) (Aldrich, Milwaukee, Wis.) in DCM (15 mL) was added oxalyl chloride (1.1 mL) and DMF (3 drops). The mixture was stirred at room temperature resulting in 1H-pyrrole-2-carbonyl chloride. Methylamine (30 mmol) was then added to the acid chloride and the mixture was stirred at room temperature. The reaction was diluted with ethyl acetate, washed with brine (2×), NaHCO$_3$, dried and concentrated to give 1H-pyrrole-2-carboxylic acid methylamide.

To a mixture of 1H-pyrrole-2-carboxylic acid methylamide (430 mg, 3.5 mmol) and 2-chloronicotinoyl chloride (0.6 g, 3.4 mmol) in benzene (15 mL) at 0° C. was added a dropwise solution of tin (IV) chloride (1.6 g) in benzene (5 mL). The mixture was allowed to warm up slowly to room temperature and stirred for 4 hours. The reaction was diluted with ethyl acetate, washed with water, brine, dried and concentrated to give 320 mg (35%) of 5-(2-chloro-pyridine-3-carbonyl)-1H-pyrrole-2-carboxylic acid methylamide.

$^1$HNMR (400 MHz, DMSO-d$_6$) δ 12.42 (br s, 1H, NH), 8.76 (s, 1H), 8.38 (m, 1H, NH), 7.98 (d, 1H), 7.52 (m, 1H), 6.76 (s, 1H), 6.58 (s, 1H), 2.76 (d, 3H, CH$_3$).

MS m/z 262 [M−1].

A mixture of 5-(2-chloro-pyridine-3-carbonyl)-1H-pyrrole-2-carboxylic acid methylamide (320 mg, 1.2 mmol) and hydrazine hydrate (2 mL) in ethanol (20 mL). The mixture was heated to at 80° C. for 48 hours. The precipitate was collected by vacuum filtration, washed with ethanol and water, dried to give 80 mg (27%) of the titled compound.

$^1$HNMR (400 MHz, DMSO-d$_6$) δ 13.71 (s, 1H, NH), 11.51 (br s, 1H, NH), 8.54 (d, 1H), 8.49 (d, J=8 Hz, 1H), 8.17 (m, 1H, NH), 7.23 (m, 1H), 6.81 (m, 2H), 2.76 (d, J=5 Hz, 3H).

MS m/z 240 [M−1].

Example 33

5-(1H-Pyrazolo[3,4-b]pyridin-3-yl)-1H-pyrrole-2-carboxylic acid (3-fluoro-phenyl)-amide

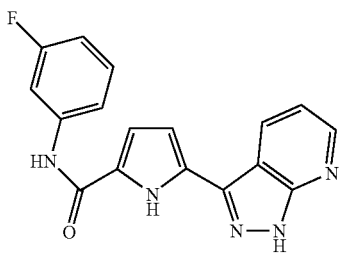

To a solution of 1H-pyrrole-2-carbonyl chloride (1.3 g, 10 mmol) (from Example 30) in DCM (20 mL) was added 3-fluoroaniline (1.2 g, 10.7 mmol) and triethylamine (1.5 mL). The mixture was stirred at room temperature for overnight. The reaction was washed with NaOH, water, brine, dried and concentrated to give 750 mg (37%) of 1H-pyrrole-2-carboxylic acid (3-fluoro-phenyl)-amide.

$^1$HNMR (400 MHz, CDCl$_3$) δ 9.50 (br s, 1H, NH), 7.58 (m, 2H), 7.24 (m, 2H), 7.02 (s, 1H), 6.82 (m, 1H, NH), 6.72 (s, 1H), 6.32 (s, 1H).

MS m/z 203 [M−1].

To a solution of 1H-pyrrole-2-carboxylic acid (3-fluoro-phenyl)-amide (1.56 g, 7.6 mmol) and 2-chloronicotinoyl chloride (1.925 g, 10.9 mmol) in benzene (15 mL) at 0° C. was added dropwise a solution of tin (IV) chloride (3.5 g) in dry benzene (5 mL). The mixture was allowed to warm up slowly to room temperature and stirred for 4 hours. The reaction was added with NaOH (100 mL) and extracted with ethyl acetate, washed with brine (2×), dried and concentrated. The residue was purified on a silica gel column to give 477 mg (18%) of 5-(2-chloro-pyridine-3-carbonyl)-1H-pyrrole-2-carboxylic acid (3-fluoro-phenyl)-amide.

$^1$HNMR (400 MHz, DMSO-d$_6$) δ 12.78 (br s, 1H, NH), 10.36 (s, 1H, NH), 8.58 (m, 1H), 8.06 (d, 1H), 7.72 (d, 1H), 7.58 (m, 1H), 7.46 (dd, 1H), 7.4 (m, 1H), 7.04 (m, 1H), 6.92 (dt, 1H), 6.65 (m, 1H).

MS m/z 342 [M−1].

A mixture of 5-(2-chloro-pyridine-3-carbonyl)-1H-pyrrole-2-carboxylic acid (3-fluoro-phenyl)-amide (477 mg, 1.4 mmol) and hydrazine hydrate (2 mL) in ethanol (30 mL) was heated at 80° C. for 24 hours. The precipitate was collected by vacuum filtration, washed with ethanol and dried to give 200 mg (45%) of the titled compound.

$^1$HNMR (400 MHz, CDCl$_3$) δ 13.83 (s, 1H, NH), 11.98 (s, 1H, NH), 10.14 (s, 1H, NH), 8.55 (m, 2H), 7.73 (d, 1H), 7.46 (d, 1H), 7.36 (m, 1H), 7.27 (m, 1H), 7.11 (s, 1H), 6.91 (m, 2H).

MS m/z 322 [M−1].

Example 34

5-(1H-Pyrazolo[3,4-b]pyridin-3-yl)-1H-pyrrole-2-carboxylic acid ((S)-1-phenyl-ethyl)-amide

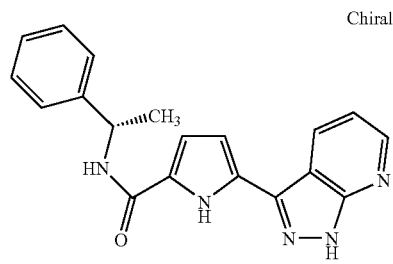

To a solution of 1H-pyrrole-2-carbonyl chloride (1.3 g, 10 mmol) (from Example 30) in DCM (20 mL) was added (S)-1-phenyl-ethylamine (1.4 g, 11.55 mmol) (Aldrich, Milwaukee, Wis.), followed by triethylamine (1.5 mL). The reaction was stirred at room temperature for overnight. The reaction was washed with 1N NaOH, water, brine, dried and concentrated to give 867 mg (40%) of 1H-pyrrole-2-carboxylic acid ((S)-1-phenyl-ethyl)-amide.

$^1$HNMR (400 MHz, CDCl$_3$) δ 9.32 (br s, 1H, NH), 7.36 (m, 5H), 6.9 (s, 1H), 6.52 (s, 1H), 6.22 (m, 1H), 6.02 (br d, 1H, NH), 5.28 (m, 1H), 1.58 (m, 3H, CH$_3$).

MS m/z 213 [M−1].

To a solution of 1H-pyrrole-2-carboxylic acid ((S)-1-phenyl-ethyl)-amide (800 mg, 3.7 mmol) and 2-chloronicotinoyl chloride (95 mg, 5.4 mmol) in dry benzene (10 mL) at 0° C. was added dropwise a solution of tin (IV) chloride (1.75 g) in benzene (5 mL). The mixture was allowed to warm up slowly to room temperature and stirred for overnight. The reaction was concentrated, diluted with ethyl acetate, washed with water, 1N NaOH, brine, dried and concentrated. The residue was purified on a silica gel column to give 458 mg (35%) of 5-(2-chloro-pyridine-3-carbonyl)-1H-pyrrole-2-carboxylic acid ((S)-1-phenyl-ethyl)-amide.

¹HNMR (400 MHz, CDCl₃) δ 10.3 (br s, 1H, NH), 8.64 (m, 1H), 8.54 (m, 1H), 7.78 (dd, 1H), 7.44 (m 1H), 7.36 (m, 5H), 6.55 (m, 1H), 6.2 (m, 1H, NH), 5.32 (m, 1H), 1.62 (d, 3H, CH₃).

MS m/z 352 [M−1].

A mixture of 5-(2-chloro-pyridine-3-carbonyl)-1H-pyrrole-2-carboxylic acid ((S)-1-phenyl-ethyl)-amide (450 mg, 1.3 mmol) and hydrazine hydrate (2 mL) in ethanol (20 mL) was heated at 80° C. for 24 hours. The reaction was concentrated, the residue was triturated with water. The precipitate was collected by vacuum filtration, washed with water and DCM to give 80 mg (19%) of the titled compound.

¹HNMR (400 MHz, DMSO-d₆) δ 13.75 (s, 1H, NH), 11.76 (s, 1H, NH), 8.52 (m, 3H), 7.33 (m, 4H), 7.23 (m, 2H), 6.86 (m, 2H), 5.05 (m, 1H), 1.47 (d, 3H, CH₃).

MS m/z 330 [M−1].

Example 35

4-(1H-Pyrazolo[3,4-b]pyridin-3-yl)-1H-pyrrole-3-carboxylic acid ethyl ester

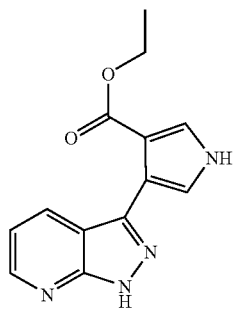

To a mixture of 1H-pyrrole-3-carboxylic acid ethyl ester (2 g, 14.4 mmol) (synthesized from 1H-pyrrole-3-carboxylic acid suing the same procedure as in Example 30) and 2-chloronicotinoyl chloride (4.4 mg, 25 mmol) in dry benzene (10 mL) at 0° C. was added dropwise a solution of tin (IV) chloride (0.7 g) in dry benzene (5 mL). The mixture was allowed to warm up slowly to room temperature and stirred for overnight. The reaction was diluted with ethyl acetate, washed with brine and concentrated. The residue was purified on a silica gel column to give 402 mg (10%) of 4-(2-chloro-pyridine-3-carbonyl)-1H-pyrrole-3-carboxylic acid ethyl ester.

¹HNMR (400 MHz, DMSO-d₆) δ 12.85 (br s, 1H, NH), 8.47 (dd, 1H), 7.83 (dd, 1H), 7.48 (m, 1H), 7.45 (d, 1H), 7.38 (m, 1H), 3.93 (q, J=7 Hz, 2H), 1.06 (t, J=7 Hz, 3H).

MS m/z 277 [M−1].

A mixture of 4-(2-chloro-pyridine-3-carbonyl)-1H-pyrrole-3-carboxylic acid ethyl ester (170 mg, 0.6 mmol) and hydrazine hydrate (0.8 g) in ethanol (10 mL) was heated at 80° C. for 24 hours. The reaction was concentrated, the residue was recrystallized to give 25 mg (16%) of the titled compound.

¹HNMR (400 MHz, DMSO-d₆) δ 13.36 (br s, 1H, NH), 11.7 (br s, 1H, NH), 8.42 (d, 1H), 7.888 (d, 1H), 7.52 (s, 1H), 7.1 (m, 2H), 7.07 (s, 1H), 4.0 (q, 2H), 0.94 (t, 3H).

MS m/z 255 [M−1].

Example 36

6-Morpholin-4-yl-3-(1H-pyrrol-2-yl)-1H-pyrazolo[3,4-b]pyridine

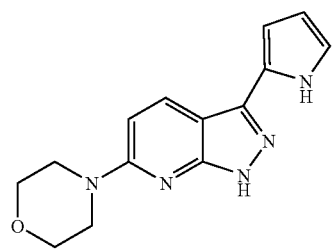

To a solution of 6-chloro-3-(1H-pyrrol-2-yl)-1H-pyrazolo-[3,4,b]-pyridine (Example 9) (100 mg) in ethanol (1 mL) was added morpholine (1 mL; Aldrich, Milwaukee, Wis.). The mixture was refluxed for 12 hours. After concentration, the residue was extracted with DCM, washed with water, brine, dried and purified on silica column to afford the title compound.

¹HNMR (400 MHz, DMSO-d₆) δ 12.75 (s, 1H,NH), 11.25 (s, 1H, NH), 8.15 (d, 1H), 6.79 (s, 1H), 6.77 (d, 1H), 6.62 (s, 1H), 6.12 (s, 1H), 3.71 (m, 4H), 3.54 (m, 4H).

MS m/z 268 [M−1].

Example 37

6-(4-Methyl-piperazin-1-yl)-3-(1H-pyrrol-2-yl)-1H-pyrazolo[3,4-b]pyridine

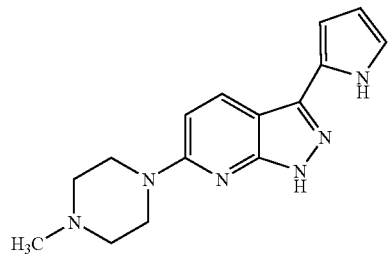

6-chloro-3-(1H-pyrrol-2-yl)-1H-pyrazolo-[3,4,b]-pyridine (Example 9) and N-methyl piperazine using the same metho in Example 36.

¹HNMR (400 MHz, CDCl₃) δ 10.68 (br s, 1H, NH), 9.37 (br s, 1H, NH), 8.03 (d, 1H), 6.89 (s, 1H), 6.70 (s, 1H), 6.65 (d, 1H), 6.33 (s, 1H), 3.72 (m, 4H), 2.55 (m, 4H), 2.36 (s, 3H, CH₃).

Example 38

5-(6-Chloro-1H-pyrazolo[3,4-b]pyridin-3-yl)-1H-pyrrole-3-sulfonic acid benzylamide

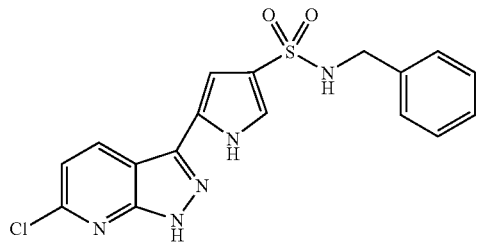

Coupled from 5-(6-chloro-1H-pyrazolo-[3,4,b]-pyridin-3-yl)-1H-pyrrole-3-sulfonyl chloride and benzylamine using the procedure in Example 18.

$^1$HNMR (400 MHz, DMSO-d$_6$) δ 13.93 (s, 1H, NH), 12.28 (br s, 1H, NH), 8.55 (d, 1H), 7.65 (t, 1H, NH), 7.35 (d, 2H), 7.30 (m, 4H), 7.2 (m, 1H), 7.0 (s, 1H), 4.0 (d, 2H, CH$_2$).

MS m/z 386 [M−1].

Example 39

5-(1H-Pyrazolo[3,4-b]pyridin-3-yl)-1H-pyrrole-3-sulfonic acid 4-methoxy-benzylamide

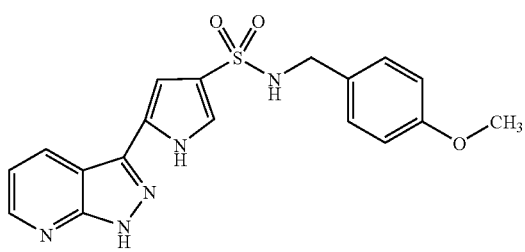

This compound was made using a procedure adapted from that described in Example 18.

$^1$HNMR (400 MHz, DMSO-d$_6$) δ 13.74 (s, 1H, NH), 12.20 (br s, 1H, NH), 8,56 (d, 1H), 8.45 (d, 1H), 7.55 (t, 1H, NH), 7.27 (m, 2H), 7.18 (d, 2H), 6.95 (s, 1H), 6.82 (d, 2H), 3.96 (d, 2H, CH$_2$), 3.65 (s, 3H, OCH$_3$).

MS m/z 382 [M−1].

Example 40

5-(1H-Pyrazolo[3,4-b]pyridin-3-yl)-1H-pyrrole-3-sulfonic acid 2,4-dichloro-benzylamide

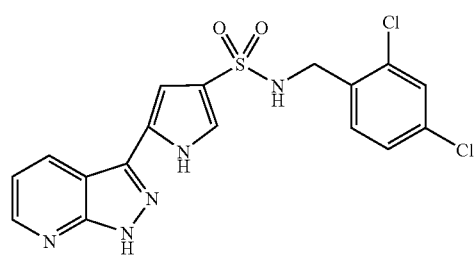

This compound was made using a procedure adapted from that described in Example 18.

$^1$HNMR (400 MHz, DMSO-d$_6$) δ 13.72 (s, 1H, NH), 12.24 (br s, 1H, NH), 8.55 (d, 1H), 8.45 (d, 1H), 7.78 (t, 1H, NH), 7.50 (m, 2H), 7.35 (m, 1H), 7.3 (m, 1H), 7.24 (dd, 1H), 6.95 (s, 1H), 4.06 (d, 2H, CH$_2$).

Example 41

5-[5-(2,6-Difluoro-phenylmethanesulfonyl)-1H-indazol-3-yl]-1H-pyrrole-2-carboxylic acid (3-fluoro-phenyl)-amide

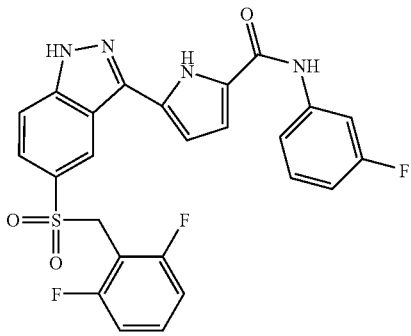

This compound was made using a procedure adapted from that described in Example 18.

White solid

MS m/z 511 [M+1]

Example 42

5-(1H-Pyrazolo[3,4-b]pyridin-3-yl)-1H-pyrrole-3-sulfonic acid 4-chloro-benzylamide

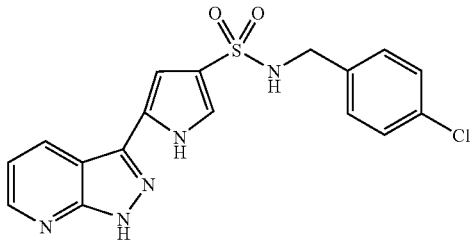

This compound was made using a procedure adapted from that described in Example 18.

$^1$HNMR (400 MHz, DMSO-d$_6$) δ 13.75 (s, 1H, NH), 12.24 (br s, 1H, NH), 8.55 (dd, 1H), 8.45 (dd, 1H), 7.70 (br t, 1H, NH), 7.32 (m, 4H), 7.30 (d, 1H), 7.26 (dd, 1H), 6.96 (d, 1H), 4.02 (d, J=7 Hz, 2H, CH$_2$).

MS m/z 388 [M−1].

Example 43

5-(1H-Pyrazolo[3,4-b]pyridin-3-yl)-1H-pyrrole-3-sulfonic acid (biphenyl-4-ylmethyl)-amide

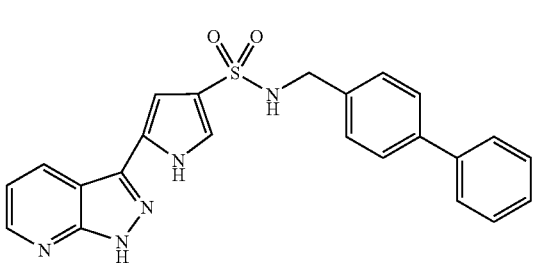

This compound was made using a procedure adapted from that described in Example 18.

¹HNMR (400 MHz, DMSO-d₆) δ 13.72 (s, 1H, NH), 12.2 (br s, 1H, NH), 8.54 (d, 1H), 8.45 (d, 1H), 7.7 (t, 1H, NH), 7.58 (d, 4H), 7.38 (m, 4H), 7.32 (m, 2H), 7.25 (dd, 1H), 6.98 (s, 1H), 4.08 (d, 2H, CH₂).

MS m/z 428 [M−1].

Example 44

5-(1H-Pyrazolo[3,4-b]pyridin-3-yl)-1H-pyrrole-3-sulfonic acid 2,6-difluoro-benzylamide

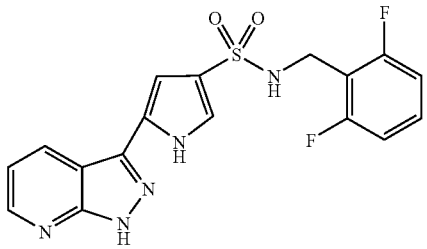

This compound was made using a procedure adapted from that described in Example 18.

MS m/z 388 [M−1].

Example 45

Benzyl-[3-(1H-pyrrol-2-yl)-1H-pyrazolo[3,4-b]pyridin-6-yl]-amine

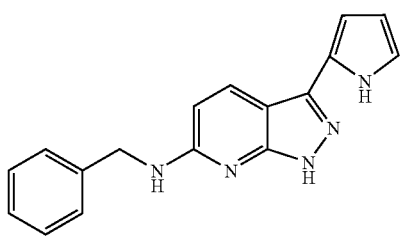

This compound was made using a procedure adapted from that described in Example 36.

¹HNMR (400 MHz, CDCl₃) δ 6 9.3 (br s, 1H, NH), 7.96 (d, 1H), 7.35 (m, 5H), 6.9 (s, 1H), 6.68 (s, 1H), 6.32 (m, 2H), 5.1 (m, 1H, NH), 4.63 (d, 2H, CH₂).

MS m/z 288 [M−1].

Example 46

3-(4-Nitro-1H-pyrrol-2-yl)-1H-pyrazolo[3,4-b]pyridine

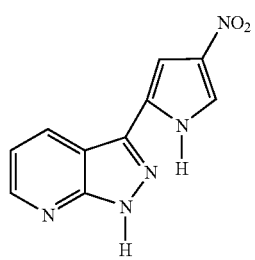

This compound was made using a procedure adapted from that described in Example 2.

¹HNMR (400 MHz, DMSO-d₆) δ 13.88 (s, 1H, NH), 12.78 (br s, 1H, NH), 8.65 (d, 1H), 8.57 (m, 1H), 7.98 (s, 1H), 7.38 (s, 1H), 7.26 (m, 1H).

MS m/z 228 [M−1].

Example 47

5-(5-Nitro-1H-indazol-3-yl)-1H-pyrrole-2-carboxylic acid (3-fluoro-phenyl)-amide

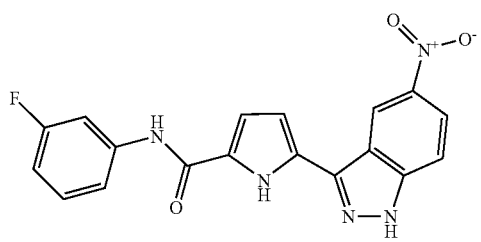

MS m/z 386 [M−1].

A mixture of 5-(2-chloro-5-nitro-benzoyl)-1H-pyrrole-2-carboxylic acid (3-fluoro-phenyl)-amide (250 mg, 0.6 mmol) (made from 5-(2-chloro-5-nitrobenzyl)-1H-pyrrole-2-carboxylic acid using a procedure adapted from that described in Example 32), hydrazine hydrate (0.3 mL), toluene (5 mL) and 1-methyl-pyrrolin-2-one (0.4 mL) was heated at 120° C. for 1.5 hours. The reaction was concentrated, mixed with water and filtered. The solid was washed to give 200 mg of the titled compound as a yellow solid.

MS m/z 364 [M−1].

Example 48

5-(1-Methyl-5-nitro-1H-indazol-3-yl)-1H-pyrrole-2-carboxylic acid (3-fluoro-phenyl)-amide

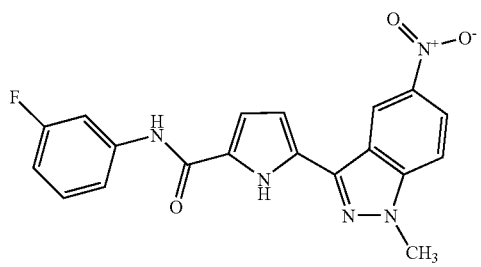

A mixture of 5-(2-chloro-5-nitro-benzoyl)-1H-pyrrole-2-carboxylic acid (3-fluoro-phenyl)-amide (250 mg, 0.6 mmol) (Example 47), methyl hydrazine (4 drops), toluene (0.6 mL) and 1-methyl-pyrrolin-2-one (0.2 mL) was heated at 120° C. for 2 hours. The reaction was concentrated, triturated with DCM and hexane to give 55 mg of the titled compound as a yellow solid.

MS m/z 378 [M−1].

Example 49

4-(5-Nitro-1H-indazol-3-yl)-1H-pyrrole-2-carboxylic acid (3-fluoro-phenyl)-amide

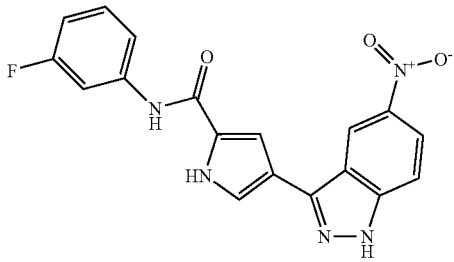

A mixture of 4-(2-chloro-5-nitro-benzoyl)-1H-pyrrole-2-carboxylic acid (3-fluoro-phenyl)-amide (150 mg, 0.39 mmol) (Example 47), hydrazine hydrate (0.2 mL), toluene (5 mL) and 1-methyl-pyrrolin-2-one (0.3 mL) was heated at 120° C. for 1.5 hours. The reaction was concentrated, mixed with water and filtered. The solid was washed to give 125 mg of the titled compound as a yellow solid.

MS m/z 364 [M−1].

Example 50

5-(1H-Pyrazolo[3,4-b]pyridin-3-yl)-1H-pyrrole-3-sulfonic acid 3-chloro-benzylamide

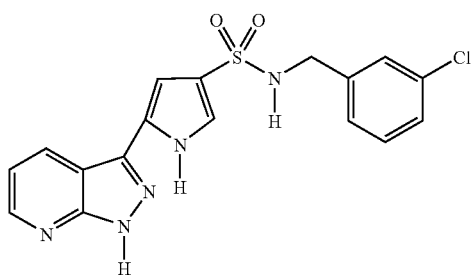

This compound was made using a procedure adapted from that described in Example 18.

$^1$HNMR (400 MHz, DMSO-$d_6$) δ 13.74 (s, 1H, NH), 12.22 (br s, 1H, NH), 8.54 (d, 1H), 8.45 (d, 1H), 7.72 (t, 1H, NH), 7.12 (m, 6H), 6.98 (s, 1H), 4.05 (d, 2H, CH$_2$).

MS m/z 386 [M−1].

Example 51

5-(1H-Pyrazolo[3,4-b]pyridin-3-yl)-1H-pyrrole-3-sulfonic acid [1-(4-chloro-phenyl)-ethyl]-amide

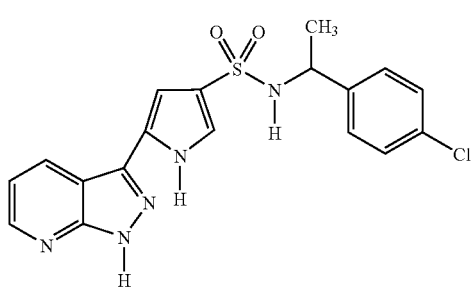

This compound was made using a procedure adapted from that described in Example 2.

$^1$HNMR (400 MHz, DMSO-$d_6$) δ 13.70 (s, 1H, NH), 12.1 (br s, 1H, NH), 8.55 (d, 1H), 8.34 (d, 1H), 7.74 (d, 1H), 7.2 (m, 6H), 6.75 (s, 1H), 4.4 (m, 1H), 1.22 (d, 3H, CH$_3$).

MS m/z 402 [M+1].

Example 52

5-(1H-Pyrazolo[3,4-b]pyridin-3-yl)-1H-pyrrole-3-sulfonic acid 4-trifluoromethyl-benzylamide

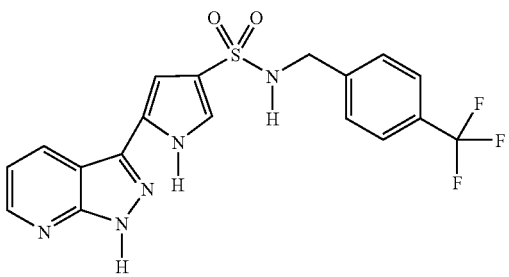

This compound was made using a procedure adapted from that described in Example 18.

$^1$HNMR (400 MHz, DMSO-$d_6$) δ 13.73 (s, 1H, NH), 12.25 (br s, 1H, NH), 8.56 (m, 1H), 8.46 (d, 1H), 7.8 (t, 1H, NH), 7.64 (d, 2H), 7.52 (d, 2H), 7.32 (m, 1H), 7.26 (m, 1H), 6.96 (m, 1H), 4.15 (d, 2H, CH$_2$).

MS m/z 420 [M−1].

Example 53

5-(1H-Pyrazolo[3,4-b]pyridin-3-yl)-1H-pyrrole-2-carboxylic acid hydrazide

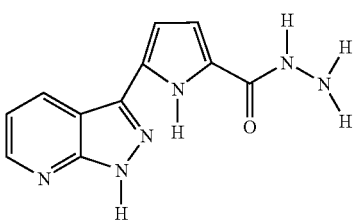

This compound was made using a procedure adapted from that described in Example 30.

$^1$HNMR (400 MHz, DMSO-$d_6$) δ 13.72 (s, 1H, NH), 11.55 (s, 1H, NH), 9.4 (s, 1H, NH), 8.52 (s, 1H), 7.23 (m, 1H), 6.85 (s, 1H), 6.8 (s, 1H), 4.38 (br s, 2H, CH$_2$).

MS m/z 241 [M−1].

Example 54

5-(6-Fluoro-1H-indazol-3-yl)-1H-pyrrole-2-carboxylic acid (3-fluoro-phenyl)-amide

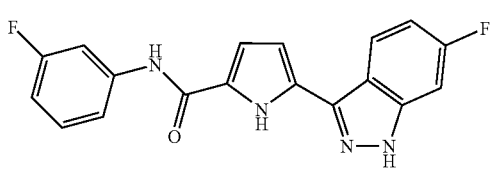

To a mixture of 1H-pyrrole-2-carboxylic acid (3-fluoro-phenyl)-amide (930 mg, 4.6 mmol) (Example 47) and 2,4-difluoro-benzoyl chloride (1.3 g, 7.4 mmol) in benzene (10 mL) at room temperature, was added a solution of tin (IV) chloride (1.5 mL). After stirring at room temperature for overnight and the usual work-up, the residue was purified on a silica gel column to give 180 mg of 5-(2,4-difluoro-benzoyl)-1H-pyrrole-2-carboxylic acid (3-fluoro-phenyl)-amide.

$^1$HNMR (400 MHz, DMSO-$d_6$) δ 12.62 (br s, 1H, NH), 10.32 (s, 1H, NH), 7.72 (m, 1H), 7.7 (dd, 1H), 7.42 (m, 3H), 7.24 (m, 1H), 7.03 (dd, 1H), 6.94 (m, 1H), 6.73 (m, 1H).

MS m/z 345 [M+1].

A mixture of 5-(2,4-difluoro-benzoyl)-1H-pyrrole-2-carboxylic acid (3-fluoro-phenyl)-amide (52 mg, 0.15 mmol), hydrazine hydrate (5 drops), 1-methyl-pyrrolin-2-one (0.3 mL) and toluene (0.8 mL) was heated at 130° C. for 1.5 hours. The reaction was concentrated, triturated with DCM and hexane to give 41 mg of the titled compound as a white solid.

MS m/z 337 [M−1].

Example 55

5-(5-Trifluoromethyl-1H-indazol-3-yl)-1H-pyrrole-2-carboxylic acid (3-fluoro-phenyl)-amide

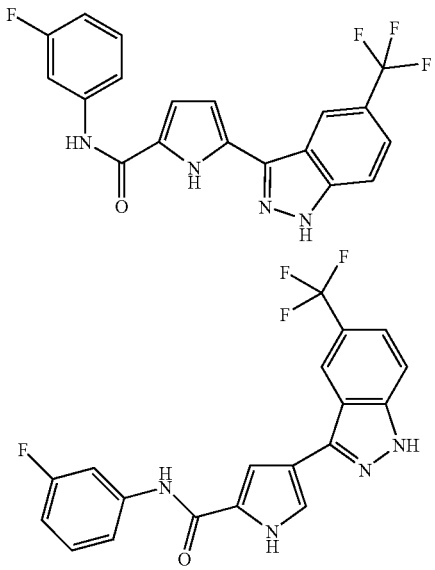

To a mixture of 1H-pyrrole-2-carboxylic acid (3-fluoro-phenyl)-amide (1 g, 4.9 mmol) and 2-fluoro-4-trifluoromethyl-benzoyl chloride (1.3 g, 5.7 mmol) (Example 47) in benzene (10 mL) at room temperature was added a solution of tin (IV) chloride (1.2 mL). After stirring at room temperature for overnight and the usual work-up, the residue was purified on a silica gel column to give 5-(2-fluoro-5-trifluoromethyl-benzoyl)-1H-pyrrole-2-carboxylic acid (3-fluoro-phenyl)-amide and 4-(2-fluoro-5-trifluoromethyl-benzoyl)-1H-pyrrole-2-carboxylic acid (3-fluoro-phenyl)-amide (MS m/z 393 [M−1]).

A mixture of 5-(2-fluoro-5-trifluoromethyl-benzoyl)-1H-pyrrole-2-carboxylic acid (3-fluoro-phenyl)-amide, hydrazine hydrate, 1-methyl-pyrrolin-2-one and toluene was heated at 120° C. for 2 hours. The reaction was concentrated, mixed with water and filtered. The solid was washed to give the titled compound.

MS m/z 387 [M−1].

Example 56

4-(5-Trifluoromethyl-1H-indazol-3-yl)-1H-pyrrole-2-carboxylic acid (3-fluoro-phenyl)-amide A mixture of 4-(2-fluoro-5-trifluoromethyl-benzoyl)-1H-pyrrole-2-carboxylic acid (3-fluoro-phenyl)-amide (45 mg, 0.1 mmol) (Example 55), hydrazine hydrate (5 drops) 1methyl-pyrrolin-2-one (0.3 mL) (Aldrich, Milwaukee, Wis.) and toluene (0.8 mL) was heated at 130° C. for 1.5 hours. The reaction was concentrated, mixed with water and filtered. The solid was washed to give 37 mg of the titled compound as a white solid.

MS m/z 387 [M−1].

Example 57

4-(1-Methyl-5-trifluoromethyl-1H-indazol-3-yl)-1H-pyrrole-2-carboxlic acid (3-fluoro-phenyl)-amide

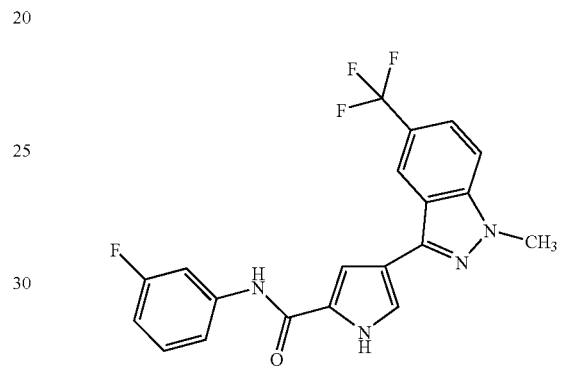

A mixture of 4-(2-fluoro-5-trifluoromethyl-benzoyl)-1H-pyrrole-2-carboxylic acid (3-fluoro-phenyl)-amide (45 mg, 0.1 mmol) (Example 55), methyl hydrazine (5 drops), 1-methyl-pyrrolin-2-one (0.3 mL) and toluene (0.7 mL) was heated at 130° C. for 1.5 hours. The reaction was concentrated, mixed with water and filtered. The solid was washed to give 50 mg of the titled compound as a white solid.

MS m/z 401 [M−1].

Example 58

5-(4-Fluoro-1H-indazol-3-yl)-1H-pyrrole-2-carboxylic acid (3-fluoro-phenyl)-amide

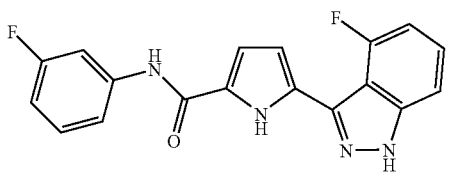

To a mixture of 1H-pyrrole-2-carboxylic acid (3-fluoro-phenyl)-amide (1 g, 4.9 mmol) (Example 55) and 2,6-difluro-benzoyl chloride 1.5 g, 8.8 mmol) (Aldrich, Milwaukee, Wis.) in benzene (10 mL) at room temperature was added a solution of tin (IV) chloride (1 mL, 2.26 g, 8.6 mmol). After stirring at room temperature for overnight, the reaction was diluted with water and ethyl acetate. The organic layer was washed with 2N NaOH, dried and purified on a silica gel column to give 205 mg of 5-(2,6-difluro-benzoyl)-1H-pyrrole-2-carboxylic acid (3-fluoro-phenyl)-amide as a white solid.

MS m/z 343 [M−1].

A mixture of 5-(2,6-difluro-benzoyl)-1H-pyrrole-2-carboxylic acid (3-fluoro-phenyl)-amide (69 mg, 0.2 mmol), hydrazine hydrate (5 drops), 1-methyl-pyrrolin-2-one (0.3 mL) and toluene (0.7 mL) was heated at 130° C. for 1.5 hours. The reaction was concentrated, mixed with water and filtered. The solid was washed to give 50 mg of the titled compound as a white solid.

MS m/z 337 [M−1].

Example 59

5-(6-Nitro-1H-indazol-3-yl)-1H-pyrrole-2-carboxylic acid (3-fluoro-phenyl)-amide

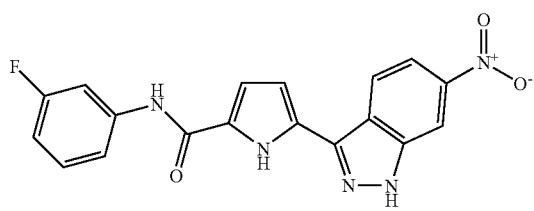

To a mixture of 1H-pyrrole-2-carboxylic acid (3-fluoro-phenyl)-amide (1 g, 4.9 mmol) (Example 55) and 2-chloro-4-nitro-benzoyl chloride (1.5 g, 6.8 mmol) (Aldrich, Milwaukee, Wis.) in benzene (10 mL) at room temperature, was added a solution of tin (IV) chloride (1.4 mL). After stirring at room temperature for 5 hours and the usual work-up, the residue was purified on a silica gel column to give 135 mg of 5-(2-chloro-4-nitro-benzoyl)-1H-pyrrole-2-carboxylic acid (3-fluoro-phenyl)-amide as a white solid.

$^1$HNMR (400 MHz, DMSO-$d_6$) δ 12.82 (br s, 1H, NH), 10.36 (s, 1H, NH), 8.43 (d, 1H), 8.29 (dd, 1H), 7.85 (d, 1H), 7.71 (dt, 1H), 7.47 (m, 1H), 7.4 (m, 1H), 7.03 (dd, 1H), 6.94 (m, 1H), 6.64 (dd, 1H).

MS m/z 386 [M−1].

A mixture of 5-(2-chloro-4-nitro-benzoyl)-1H-pyrrole-2-carboxylic acid (3-fluoro-phenyl)-amide (30 mg), hydrazine hydrate (3 drops), 1-methyl-pyrrolin-2-one (0.3 mL) and toluene (0.7 mL) was heated at 120° C. for 3 hours. The reaction was concentrated, triturated with DCM-hexane and filtered to give 11 mg of the titled compound as a light yellow solid.

MS m/z 364 [M−1].

Example 60

5-(1H-Pyrazolo[3,4-b]pyridin-3-yl)-1H-pyrrole-3-sulfonic acid 4-fluoro-benzylamide

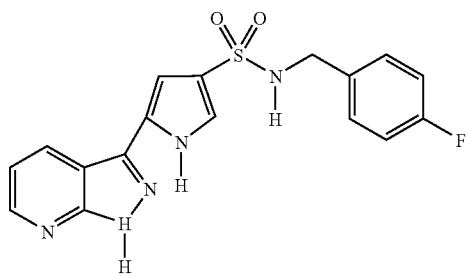

This compound was made using a procedure adapted from that described in Example 18.

$^1$HNMR (400 MHz, DMSO-$d_6$) δ 13.74 (br s, 1H, NH), 12.22 (br s, 1H, NH), 8.58 (dd, 1H), 8.48 (dd, 1H), 7.68 (t, 1H, NH), 7.3 (m, 4H), 7.10 (t, 2H), 6.98 (m, 1H), 4.01 (d, 2H, CH$_2$).

MS m/z 370 [M−1].

Example 61

5-(1H-Pyrazolo[3,4-b]pyridin-3-yl)-1H-pyrrole-3-sulfonic acid 4-dimethylamino-benzylamide

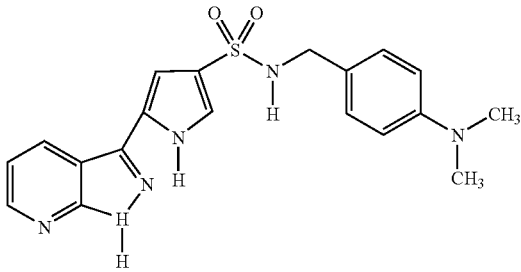

This compound was made using a procedure adapted from that described in Example 18.

$^1$HNMR (400 MHz, DMSO-$d_6$) δ 13.72 (s, 1H, NH), 12.20 (s, 1H, NH), 8.55 (dd, 1H), 8.44 (dd, 1H), 7.42 (t, 1H, NH), 7.28 (dd, 1H), 7.26 (dd, 1H), 7.06 (d, 2H), 6.93 (m, 1H), 6.6 (d, 2H), 3.90 (d, 2H, CH$_2$), 2.78 (s, 6H, 2×CH$_3$).

MS m/z 395 [M−1].

Example 62

1-[5-(1H-Pyrazolo[3,4-b]pyridin-3-yl)-1H-pyrrole-3-sulfonyl]-piperidin-3-ol

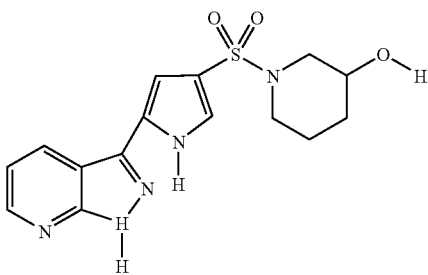

This compound was made using a procedure adapted from that described in Example 18.

$^1$HNMR (400 MHz, DMSO-$d_6$) δ 13.76 (s, 1H, NH), 12.43 (br s, 1H, NH), 8.56 (m, 2H), 7.32 (s, 1H), 7.25 (m, 1H), 6.96 (s, 1H), 4.9 (m, 1H), 3.62 (m, 1H), 3.4 (m, 2H), 2.3 (m, 1H), 2.1 (m, 1H), 1.7 (m, 2H), 1.48 (m, 1H), 1.06 (m, 1H).

MS m/z 346 [M−1].

Example 63

5-(5-Nitro-1H-indazol-3-yl)-1H-pyrrole-2-carboxylic acid (3-hydroxy-phenyl)-amide

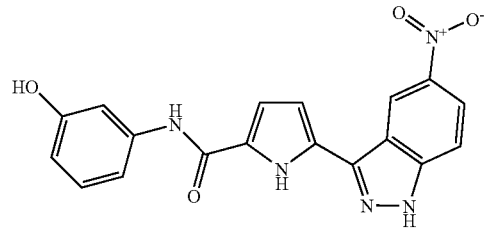

TiCl$_4$ (5 mL) was add to a solution of 1H-pyrrole-2-carboxylic acid ethyl ester (12 g, 46 mmol) in benzene (5 mL) at 0° C. After stirring at room temperature for 2 days, the reaction was diluted with ethyl acetate, washed with 2N NaOH, brine and dried to give 5-(2-chloro-5-nitro-benzoyl)-1H-pyrrole-2-carboxylic acid ethyl ester.

$^1$HNMR (400 MHz, DMSO-d$_6$) δ 13.05 (br s, 1H, NH), 8.37 (s, 1H), 8.36 (d, 1H), 7.88 (d, 1H), 6.84 (m, 1H), 6.67 (m, 1H), 4.27 (q, J=7 Hz, 2H), 1.29 (t, J=7 Hz, 3H).

MS m/z 321 [M−1].

5-(2-Chloro-5-nitro-benzoyl)-1H-pyrrole-2-carboxylic acid ethyl ester was hydrolyzed to give 5-(2-chloro-5-nitro-benzoyl)-1H-pyrrole-2-carboxylic acid.

5-(2-Chloro-5-nitro-benzoyl)-1H-pyrrole-2-carboxylic acid (200 mg) was converted to 5-(2-chloro-5-nitro-benzoyl)-1H-pyrrole-2-carbonyl chloride using oxalyl chloride at room temperature for one hour. It was then condensed with 2-morpholin-4-yl-ethylamine and TEA for one hour at room temperature to give 120 mg of 5-(2-chloro-5-nitro-benzoyl)-1H-pyrrole-2-carboxylic acid (2-morpholin-4-yl-ethyl)-amide.

A mixture of 5-(2-chloro-5-nitro-benzoyl)-1H-pyrrole-2-carboxylic acid (2-morpholin-4-yl-ethyl)-amide (50 mg), hydrazine hydrate (5 drops), 1-methyl-pyrrolin-2-one (0.4 mL), toluene (1.5 mL) and ethanol (0.3 mL) was heated at 130° C. for one hour. The reaction was cooled and the resulted precipitate was collected by vacuum filtration to give 27.8 mg of the titled compound as a yellow solid.

MS m/z 383 [M−1],

Example 64

5-(5-Nitro-1H-indazol-3-yl)-1H-pyrrole-2-carboxylic acid (2-morpholin-4-yl-ethyl)-amide

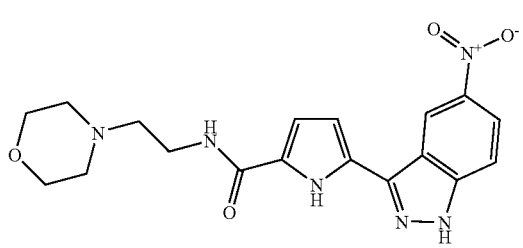

5-(2-Chloro-5-nitro-benzoyl)-1H-pyrrole-2-carboxylic acid (200 mg) (Example 63) was converted to 5-(2-chloro-5-nitro-benzoyl)-1H-pyrrole-2-carbonyl chloride using oxalyl chloride at room temperature for one hour. It was then condensed with 3-amino-phenol (170 mg, 1.7 eq.) and TEA at room temperature for 1.5 hrs to give 135 mg of 5-(2-chloro-5-nitro-benzoyl)-1H-pyrrole-2-carboxylic acid (3-hydroxy-phenyl)-amide.

A mixture of 5-(2-chloro-5-nitro-benzoyl)-1H-pyrrole-2-carboxylic acid (3-hydroxy-phenyl)-amide (50 mg), hydrazine hydrate (5 drops), 1-methyl-pyrrolin-2-one (0.4 mL) and toluene (1.5 mL) was heated to 130° C. for one hour. The reaction was cooled and the resulted solid was collected by vacuum filtration to give 45 mg of the titled compound as a yellow solid.

MS m/z 362 [M−1].

Example 65

5-(5-Methanesulfonyl-1H-indazol-3-yl)-1H-pyrrole-2-carboxylic acid (3-fluoro-phenyl)-amide

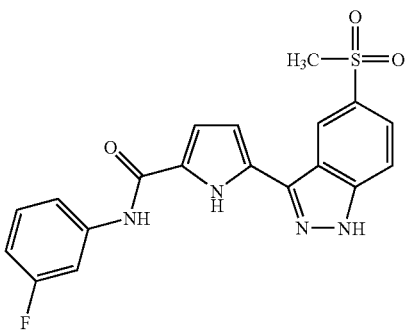

Cream Solid.

This compound was made using a procedure adapted from that described in Example 63.

$^1$HNMR (400 MHz, DMSO-d$_6$) δ 13.78 (s, 1H, NH), 12.12 (s, 1H, NH), 10.16 (s, 1H, NH), 8.56 (s, 1H), 7.89 (dd, 1H), 7.79 (d, 1H), 7.76 (m, 1H), 7.5 (d, 1H), 7.37 (m, 1H), 7.19 (m, 1H), 6.9 (m, 2H), 3.27 (s, 3H, CH$_3$).

MS m/z 399 [M+1].

Example 66

3-(1-Benzenesulfonyl-1H-pyrrol-2-yl)-1H-pyrazolo[3,4-b]pyridine

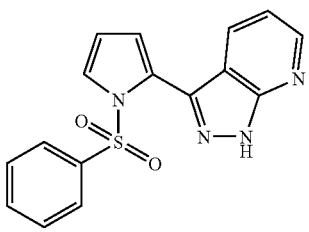

To a solution of 2-chloro-nicotinoyl chloride (1.17 g) (Aldrich, Milwaukee, Wis.) and 1-benzensulfonyl-1H-pyrrole (1 g) (Aldrich) in dichloroethane (15 mL) was added aluminum chloride (1.1 g). After stirring at room temperature for one hour, the reaction was diluted with ethyl acetate, washed with water, base and brine, dried and purified to give 820 mg of (1-benzenesulfonyl-1H-pyrrol-2-yl)-(2-chloro-pyridin-3-yl)-methanone.

$^1$HNMR (400 MHz, CDCl$_3$) δ 8.48 (m, 1H), 8.09 (d, 2H), 7.95 (m, 1H), 7.67 (m, 2H), 7.57 (m, 2H), 7.3 (m, 1H), 6.61 (m, 1H), 6.37 (m, 1H).

A mixture of (1-benzenesulfonyl-1H-pyrrol-2-yl)-(2-chloro-pyridin-3-yl)-methanone (150 mg) and hydrazine hydrate (0.15 mL) in ethanol (3.5 mL) was heated at 90° C. for overnight. The reaction was concentrated, diluted with ethyl acetate, washed with base and water, dried and concentrated to give 75 mg of the titled compound as a white solid.

MS m/z 325 [M+1].

Example 67

3-[4-(4-Chloro-phenylmethanesulfonyl)-1H-pyrrol-2-yl]-1H-pyrazolo[3,4-b]pyridine

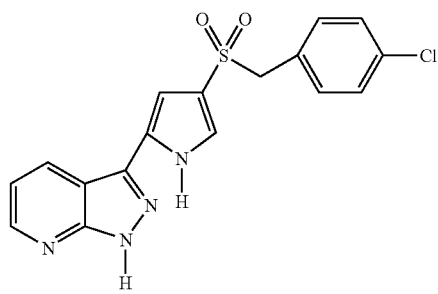

Chlorosulfonic acid (d 1.753) (6.6 ml, 0.1 mol) was added dropwise to (2-chloro-pyridin-3-yl)-(1H-pyrrol-2-yl)-methanone (2.06 g, 10 mmol) (Example 2) at 0° C. The stirred mixture was then allowed to stand at 0° C. for 24 hours, after which it was poured carefully dropwise into ice water. Filter the white precipitate and washed with water. Dried to afford 2.9 g (95% yield) of white solid, 5-[(2-chloropyridin-3-yl)carbonyl]-1H-pyrrole-3-sulfonyl chloride.

5-[(2-chloropyridin-3-yl)carbonyl]-1H-pyrrole-3-sulfonyl chloride (500 mg, 1.64 mmol), $Na_2SO_3$ (413 mg, 3.28 mmol), $Na_2HPO_4$ (233 mg, 1.64 mmol) were mixed in 4 mL of water and heated to 60° C. overnight (16 hour). The initial creamy suspension became clear and then cloudy. A solution of 4-chlorobenzyl bromide (337 mg, 1.64 mmol) in acetone (4 mL) was added to the reaction solution dropwise with stirring. The mixture was stirred at 60° C. for 4 hour and then cooled down to room temperature. Quenched with 4 mL of water and stirred for another 1 hour. Filtered and washed with water and acetone to afford the product, {4-[(4-chlorobenzyl)sulfonyl]-1H-pyrrol-2-yl}(2-chloropyridin-3-yl)methanone as white solid 646 mg (90% yield).

{4-[(4-chlorobenzyl)sulfonyl]-1H-pyrrol-2-yl}(2-chloropyridin-3-yl)methanone (280 mg, 0.711 mmol) and 359 mg of hydrazine monohydrate (7.11 mmol) were mixed in 4 mL of ethanol. The mixture was stirred at 80° C. overnight (16 hour) and then cooled down to room temperature. Water was added and filtered. Washed with additional water and methanol to collect the product, dried to afford 250 mg (95% yield) of the title compound.

$^1$HNMR (400 MHz, DMSO-$d_6$) δ 13.77 (s, 1H, NH), 12.4 (s, 1H, NH), 8.56 (d, 1H), 8.46 (dd, 1H), 7.37 (d, 2H), 7.26 (m, 1H), 7.23 (d, 2H), 7.17 (m, 1H), 6.97 (s, 1H), 4.6 (s, 2H, $CH_2$).

MS m/z 373 [M+1].

Example 68

3-[4-(4-Fluoro-phenylmethanesulfonyl)-1H-pyrrol-2-yl]-1H-pyrazolo[3,4-b]pyridine

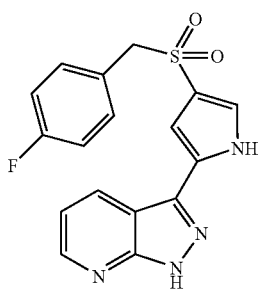

This compound was made using a procedure adapted from that described in Example 67, using 4-fluorobenzylbromide.

$^1$HNMR (400 MHz, DMSO-$d_6$) δ 13.77 (s, 1H, NH), 12.38 (s, 1H, NH), 8.56 (d, 1H), 8.46 (dd, 1H), 7.37 (m, 3H), 7.26 (m, 3H), 7.0 (s, 1H), 4.6 (s, 2H, $CH_2$).

MS m/z 357 [M+1].

Example 69

3-[4-(4-Trifluoromethoxy-phenylmethanesulfonyl)-1H-pyrrol-2-yl]-1H-pyrazolo[3,4-b]pyridine

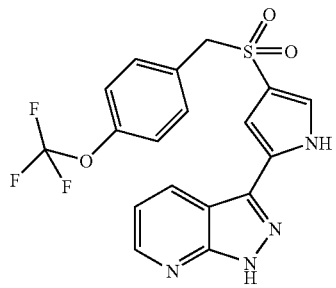

This compound was made using a procedure adapted from that described in Example 67, using 4-trifluoromethoxybenzylbromide.

$^1$HNMR (400 MHz, DMSO-$d_6$) δ 13.77 (s, 1H, NH), 12.4 (s, 1H, NH), 8.58 (d, 1H), 8.46 (dd, 1H), 7.37 (m, 3H), 7.25 (m, 3H), 6.9 (s, 1H), 4.6 (s, 2H, $CH_2$).

MS m/z 423 [M+1].

Example 70

3-[4-(4-Nitro-phenylmethanesulfonyl)-1H-pyrrol-2-yl]-1H-pyrazolo[3,4-b]pyridine

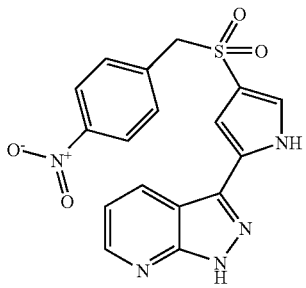

This compound was made using a procedure adapted from that described in Example 67, using 4-nitrobenzylbromide.

$^1$HNMR (400 MHz, DMSO-$d_6$) δ 13.77 (s, 1H, NH), 12.4 (s, 1H, NH), 8.58 (d, 1H), 8.45 (dd, 1H), 8.2 (m, 2H), 7.46 (m, 2H), 7.28 (m, 2H), 7.0 (s, 1H), 4.8 (s, 2H, CH$_2$).

MS m/z 384 [M+1].

Example 71

3-[4-(2-Chloro-phenylmethanesulfonyl)-1H-pyrrol-2-yl]-1H-pyrazolo[3,4-b]pyridine

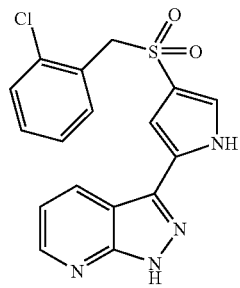

This compound was made using a procedure adapted from that described in Example 67, using 2-chlorobenzylbromide.

$^1$HNMR (400 MHz, DMSO-$d_6$) δ 13.77 (s, 1H, NH), 12.4 (s, 1H, NH), 8.55 (d, 1H), 8.45 (dd, 1H), 7.4 (m, 3H), 7.3 (m, 2H), 7.2 (m, 1H), 6.9 (s, 1H), 4.65 (s, 2H, CH$_2$).

MS m/z 373 [M+1].

Example 72

3-[4-(3-Chloro-phenylmethanesulfonyl)-1H-pyrrol-2-yl]-1H-pyrazolo[3,4-b]pyridine

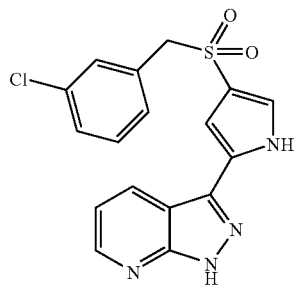

This compound was made using a procedure adapted from that described in Example 67, using 3-chlorobenzylbromide.

$^1$HNMR (400 MHz, DMSO-$d_6$) δ 13.77 (s, 1H, NH), 12.4 (s, 1H, NH), 8.55 (d, 1H), 8.45 (dd, 1H), 7.35 (m, 4H), 7.2 (m, 2H), 7.0 (s, 1H), 4.6 (s, 2H, CH$_2$).

MS m/z 373 [M+1].

Example 73

3-[4-(Biphenyl-2-ylmethanesulfonyl)-1H-pyrrol-2-yl]-1H-pyrazolo[3,4-b]pyridine

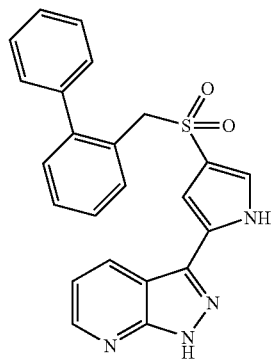

This compound was made using a procedure adapted from that described in Example 67, using 2-phenylbenzylbromide.

$^1$HNMR (400 MHz, DMSO-$d_6$) δ 13.77 (s, 1H, NH), 12.38 (s, 1H, NH), 8.55 (d, 1H), 8.45 (dd, 1H), 7.4 (m, 11H), 6.6 (s, 1H), 4.5 (s, 2H, CH$_2$).

MS m/z 415 [M+1].

Example 74

3-[4-(3-Trifluoromethoxy-phenylmethanesulfonyl)-1H-pyrrol-2-yl]-1H-pyrazolo[3,4-b]pyridine

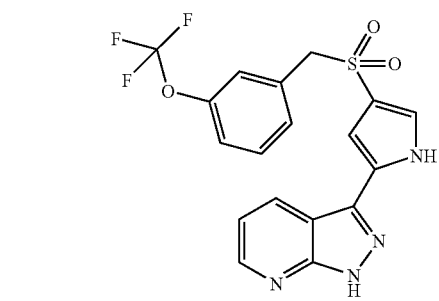

This compound was made using a procedure adapted from that described in Example 67, using 3-trifluoromethoxybenzylbromide.

$^1$HNMR (400 MHz, DMSO-$d_6$) δ 13.77 (s, 1H, NH), 12.4 (s, 1H, NH), 8.55 (d, 1H), 8.45 (dd, 1H), 7.45 (m, 1H), 7.35 (m, 3H), 7.2 (m, 2H), 7.0 (s, 1H), 4.65 (s, 2H, CH$_2$).

MS m/z 423 [M+1].

Example 75

3-[4-(2,6-Difluoro-phenylmethanesulfonyl)-1H-pyrrol-2-yl]-1H-pyrazolo[3,4-b]pyridine

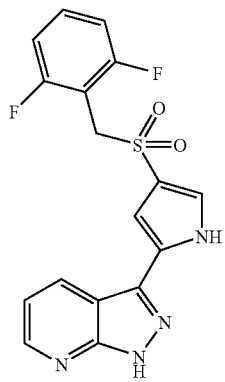

This compound was made using a procedure adapted from that described in Example 67, using 2,6-difluorobenzylbromide.

$^1$HNMR (400 MHz, DMSO-d$_6$) δ 13.77 (s, 1H, NH), 12.45 (s, 1H, NH), 8.55 (d, 1H), 8.45 (dd, 1H), 7.45 (m, 1H), 7.25 (m, 2H), 7.15 (m, 2H), 7.0 (s, 1H), 4.65 (s, 2H, CH$_2$).
MS m/z 375 [M+1].

Example 76

3-[4-(3,4-Difluoro-phenylmethanesulfonyl)-1H-pyrrol-2-yl]-1H-pyrazolo[3,4-b]pyridine

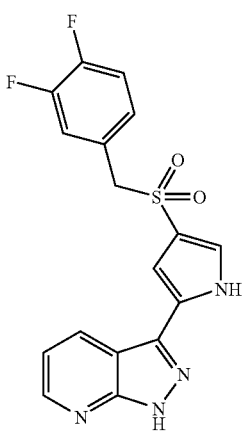

This compound was made using a procedure adapted from that described in Example 67, using 3,4-difluorobenzylbromide.

$^1$HNMR (400 MHz, DMSO-d$_6$) δ 13.77 (s, 1H, NH), 12.4 (s, 1H, NH), 8.55 (d, 1H), 8.45 (dd, 1H), 7.35 (m, 1H), 7.25 (m, 2H), 7.2 (m, 1H), 7.15 (m, 1H), 7.0 (s, 1H), 4.65 (s, 2H, CH$_2$).
MS m/z 375 [M+1].

Example 77

3-{4-[3-(4-Fluoro-phenoxy)-phenylmethanesulfonyl]-1H-pyrrol-2-yl}-1H-pyrazolo[3,4-b]pyridine

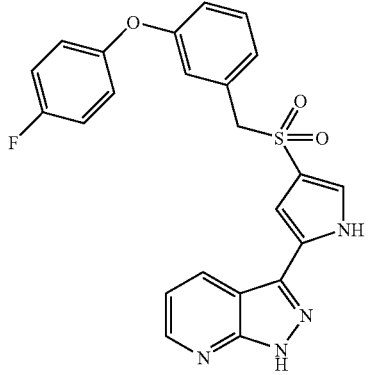

This compound was made using a procedure adapted from that described in Example 67, using 4-fluorobenzylbromide.

$^1$HNMR (400 MHz, DMSO-d$_6$) δ 13.77 (s, 1H, NH), 12.4 (s, 1H, NH), 8.55 (d, 1H), 8.4 (dd, 1H), 7.4 (m, 2H), 7.2 (m, 2H), 6.9 (m, 4H), 6.8 (m, 2H), 6.65 (s, 1H), 4.65 (s, 2H, CH$_2$).
MS m/z 449 [M+1].

Example 78

3-[4-(Pyridin-4-ylmethanesulfonyl)-1H-pyrrol-2-yl]-1H-pyrazolo[3,4-b]pyridine

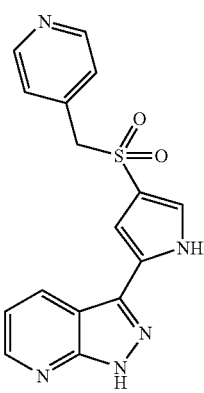

This compound was made using a procedure adapted from that described in Example 67, using 4-(bromomethyl)pyridine.

$^1$HNMR (400 MHz, DMSO-d$_6$) δ 13.77 (s, 1H, NH), 12.4 (s, 1H, NH), 8.55 (d, 1H), 8.4 (m, 3H), 7.2 (m, 4H), 7.0 (s, 1H), 4.65 (s, 2H, CH$_2$).
MS m/z 340 [M+1].

Example 79

3-[4-(3-Methoxy-phenylmethanesulfonyl)-1H-pyrrol-2-yl]-1H-pyrazolo[3,4-b]pyridine

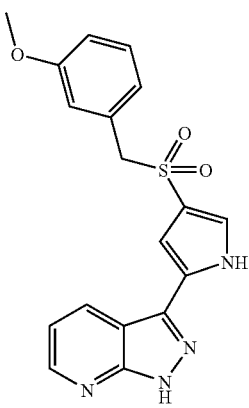

This compound was made using a procedure adapted from that described in Example 67, using 3-methoxybenzylbromide.

$^1$HNMR (400 MHz, DMSO-$d_6$) δ 13.77 (s, 1H, NH), 12.4 (s, 1H, NH), 8.55 (d, 1H), 8.45 (dd, 1H), 7.3 (m, 1H), 7.2 (m, 2H), 7.0 (s, 1H), 6.8 (m, 2H), 6.75 (s, 1H), 4.65 (s, 2H), 3.8 (s, 3H).

MS m/z 369 [M+1].

Example 80

3-(4-m-Tolylmethanesulfonyl-1H-pyrrol-2-yl)-1H-pyrazolo[3,4-b]pyridine

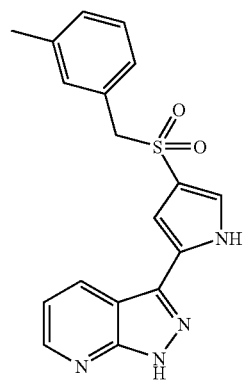

This compound was made using a procedure adapted from that described in Example 67, using 3-methylbenzylbromide.

$^1$HNMR (400 MHz, DMSO-$d_6$) δ 13.77 (s, 1H, NH), 12.4 (s, 1H, NH), 8.55 (d, 1H), 8.45 (dd, 1H), 7.5 (m, 1H), 7.2 (m, 5H), 6.95 (s, 1H), 4.6 (s, 2H), 2.25 (s, 3H).

MS m/z 353 [M+1].

Example 81

3-[4-(3,5-Difluoro-phenylmethanesulfonyl)-1H-pyrrol-2-yl]-1H-pyrazolo[3,4-b]pyridine

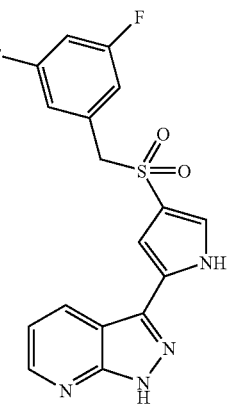

This compound was made using a procedure adapted from that described in Example 67, using 3,5-difluorobenzylbromide.

$^1$HNMR (400 MHz, DMSO-$d_6$) δ 13.77 (s, 1H, NH), 12.4 (s, 1H, NH), 8.55 (d, 1H), 8.45 (dd, 1H), 7.2 (m, 3H), 7.0 (s, 1H), 6.95 (m, 2H), 4.65 (s, 2H).

MS m/z 375 [M+1].

Example 82

3-[4-(2,6-Dimethyl-phenylmethanesulfonyl)-1H-pyrrol-2-yl]-1H-pyrazolo[3,4-b]pyridine

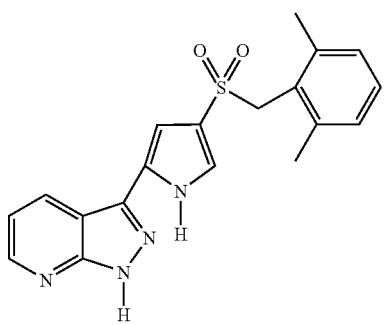

This compound was made using a procedure adapted from that described in Example 67, using 2,6-dimethylbenzylbromide.

MS m/z 367 [M+1].

Example 83

3-[4-(3-Nitro-phenylmethanesulfonyl)-1H-pyrrol-2-yl]-1H-pyrazolo[3,4-b]pyridine

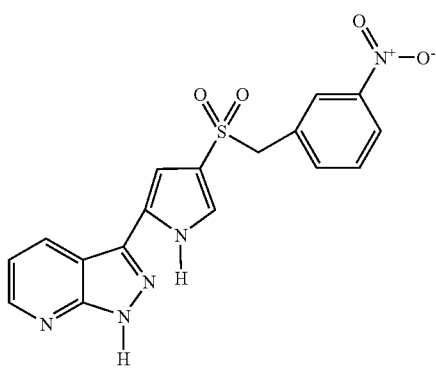

This compound was made using a procedure adapted from that described in Example 67, using 3-nitrobenzylbromide.
MS m/z 384 [M+1].

Example 84

3-[4-(4-Trifluoromethyl-phenylmethanesulfonyl)-1H-pyrrol-2-yl]-1H-pyrazolo[3,4-b]pyridine

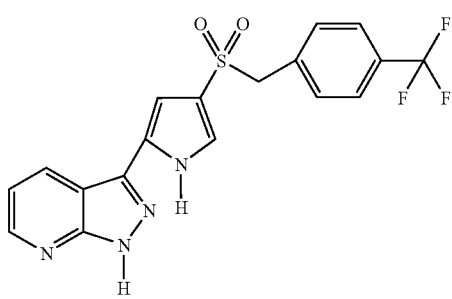

This compound was made using a procedure adapted from that described in Example 67, using 4-trifluoromethylbenzylbromide.
MS m/z 407 [M+1].

Example 85

5-(1H-pyrazolo[3,4-b]pyridin-3-yl)-1H-pyrrole-3-carboxylic acid, 4-chlorobenzylamide

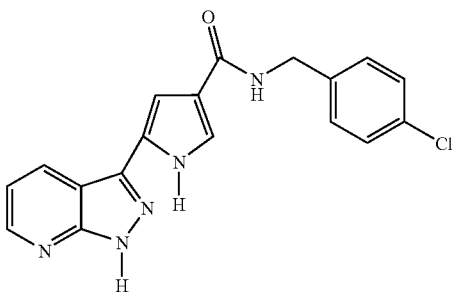

A mixture of 5-(1H-pyrazolo[3,4-b]pyridin-3-yl)-1H-pyrrole-3-carboxylic acid (50 mg, 0.22 mmol), HOBt (74 mg, 2.5 eq.), EDAC•HCl (105 mg, 2.5 eq.), 4-chlorobenzylamine (4 eq.) and TEA (0.5 mL) in DMF (1 mL) was heated at 40° C. overnight. The reaction was concentrated and the residue was purified on a silica gel column to give the titled compound as a white solid.

$^1$HNMR (400 MHz, DMSO-d$_6$) δ 13.6 (s, 1H), 11.9 (s, 1H), 8.4–8.55 (m, 2H), 7.39 (m, 4H), 7.25 (m, 2H), 4.43 (d, 2H, CH).
MS m/z 352 [M+1].

General Scheme for 5-aryl Pyrrole Pyridopyrazoles

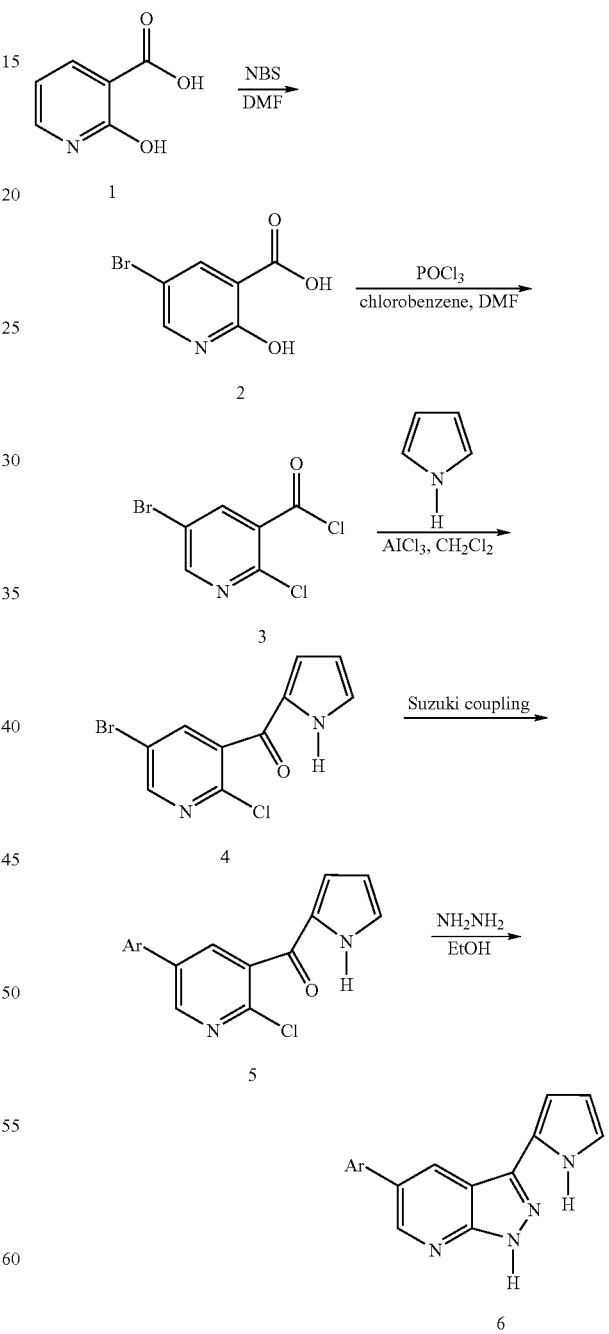

2-Hydroxy pyridine 3-carboxylic acid 1 and N-bromosuccinimide (NBS) (1 eq) were mixed in dimethyl formamide (DMF). The mixture was heated at 130° C. for two hours and concentrated, washed with dichloromethane (DCM) and ethylacetate (EtOAc) to obtain compound 2. A suspension of compound 2 in chlorobenzene/DMF was treated with phosphoryl chloride (POCl$_3$) and refluxed for 2 hours to form compound 3. After concentration, crude compound 3 was used directly for acylation of pyrrole to afford compound 4. Suzuki coupling of compound 4 with appropriate boronic acid or boronic ester. Microwaving (140° C. for 5 min) or warming (80° C. overnight) the appropriate boronic acid or ester followed by cyclization with hydrazine afforded the 5-aryl pyrrole pyridopyrazoles 6.

Example 86

5-(2-phenoxyphenyl)-3-(1H-pyrrol-2-yl)-1H-pyrazolo[3,4-b]pyridine

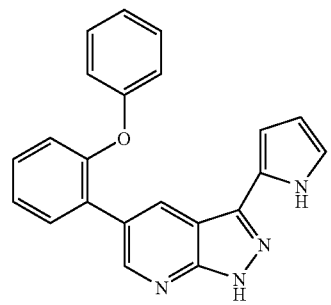

$^1$HNMR (400 MHz, DMSO-d$_6$) δ 9.6 (s, 1H), 8.8 (s, 1H), 8.5 (s, 1H), 7.55 (d, 1H), 7.4 (m, 1H), 7.3 (m, 2H), 7.17 (d, 1H), 7.05 (m, 1H), 6.95 (m, 3H), 6.65 (d, 1H), 6.35 (m, 1H).
MS m/z 352 [M+].

Example 87

5-(4-methoxyphenyl)-3-(1H-pyrrol-2-yl)-1H-pyrazolo[3,4-b]pyridine

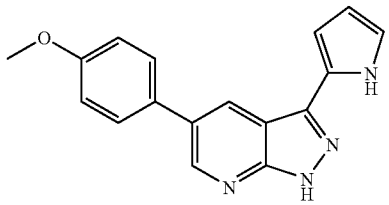

$^1$HNMR (400 MHz, DMSO-d$_6$) δ 9.57 (s, 1H), 8.78 (s, 1H), 8.40 (s, 1H), 7.56 (d, 2H), 7.05 (d, 2H), 6.98 (m, 1H), 6.85 (m, 1H), 6.38 (m, 1H), 3.88 (s, 3H).
MS m/z 291 [M+1].

Example 88

5-phenyl-3-(1H-pyrrol-2-yl)-1H-pyrazolo[3,4-b]pyridine

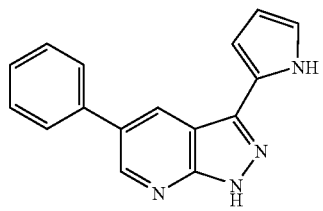

$^1$HNMR (400 MHz, DMSO-d$_6$) δ 10.0 (s, 1H), 8.81 (s, 1H), 8.45 (s, 1H), 7.64 (d, 2H), 7.52 (m, 2H), 7.42 (m, 2H), 7.0 (s, 1H), 6.85 (s, 1H), 6.37 (s, 1H).
MS m/z 261 [M+1].

Example 89

5-(3-nitrophenyl)-3-(1H-pyrrol-2-yl)-1H-pyrazolo[3,4-b]pyridine

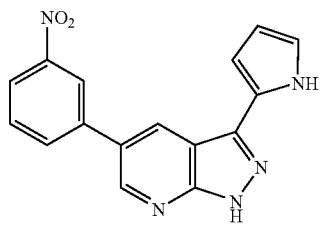

$^1$HNMR (400 MHz, DMSO-d$_6$) δ 9.33 (s, 1H), 8.85 (s, 1H), 8.52 (m, 2H), 8.29 (m, 1H), 7.99 (m, 1H), 7.71 (m, 1H), 6.99 (m, 1H), 6.88 (m, 1H), 6.41 (m, 1H).
MS m/z 306 [M+1].

Example 90

5-(4-phenoxyphenyl)-3-(1H-pyrrol-2-yl)-1H-pyrazolo[3,4-b]pyridine

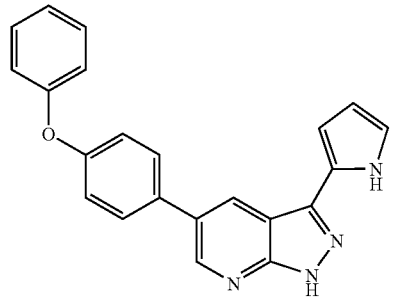

$^1$HNMR (400 MHz, DMSO-d$_6$) δ 9.8 (s, 1H), 8.88 (s, 1H), 8.51 (s, 1H), 7.67 (m, 2H), 7.45 (m, 2H), 7.22 (m, 3H), 7.17 (m, 2H), 7.06 (d, 1H), 6.93 (s, 1H), 6.45 (d, 1H).
MS m/z 353 [M+1].

Example 91

5-(1,1'-biphenyl-4-yl)-3-(1H-pyrrol-2-yl)-1H-pyrazolo[3,4-

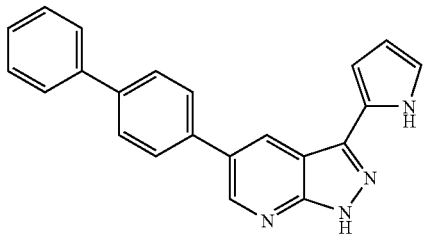

b]pyridine
MS m/z 337 [M+1].

Example 92

5-(1,1'-biphenyl-3-yl)-3-(1H-pyrrol-2-yl)-1H-pyrazolo[3,4-

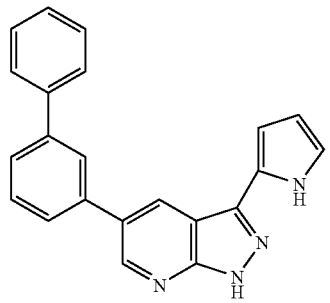

b]pyridine
MS m/z 337 [M+1].

Example 93

5-(1,1'-biphenyl-2-yl)-3-(1H-pyrrol-2-yl)-1H-pyrazolo[3,4-

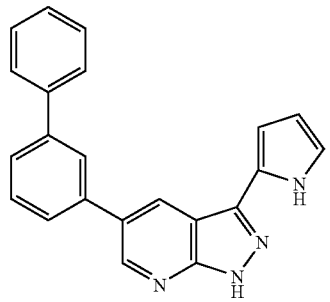

b]pyridine
MS m/z 337 [M+1].

Example 94

3-{4-[(3-chloro-4-fluorobenzyl)sulfonyl]-1H-pyrrol-2-yl}-1H-pyrazolo[3,4-b]pyridine

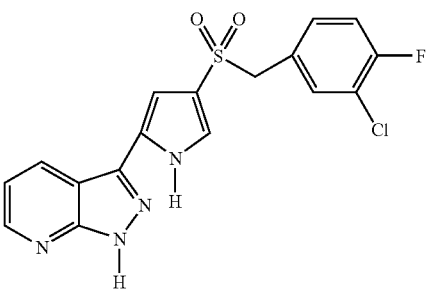

Using the same procedure for Example 67
MS m/z 391 [M+1].

Example 95

3-(4-{[3-fluoro-4-(trifluoromethyl)benzyl]sulfonyl}-1H-pyrrol-2-yl)-1H-pyrazolo[3,4-b]pyridine

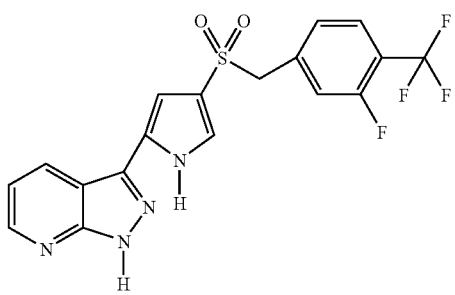

Using the same procedure for Example 67
MS m/z 425 [M+1].

Example 96

5-(3-chloro-4-fluorophenyl)-3-(1H-pyrrol-2-yl)-1H-pyrazolo[3,4-b]pyridine

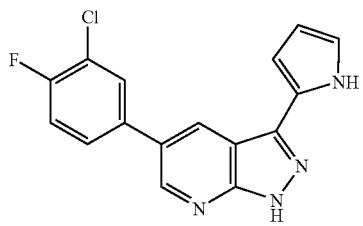

MS m/z 313 [M+1].

Example 97

5-[2-(benzyloxy)phenyl]-3-(1H-pyrrol-2-yl)-1H-pyrazolo[3,4-b]pyridine

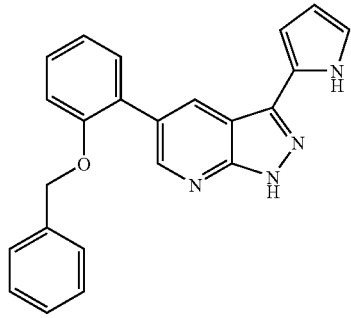

Obtained by Suzuki coupling with 2-benzyloxybenzeneboronic acid.

$^1$HNMR (400 MHz, DMSO-d$_6$) δ 13.46 (s, 1H), 11.41 (s, 1H), 8.65 (d, 1H), 8.56 (d, 1H), 7.49 (m, 1H), 7.40 (m, 3H), 7.38 (m, 4H), 7.10 (m, 1H), 6.85 (d, 1H), 6.68 (s, 1H), 6.16 (d, 1H), 5.14 (s, 2H).

MS m/z 367 [M+1].

Example 98

5-dibenzo[b,d]furan-4-yl-3-(1H-pyrrol-2-yl)-1H-pyrazolo[3,4-b]pyridine

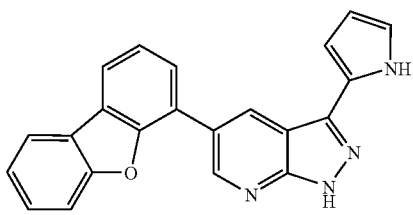

Obtained by Suzuki coupling with 4-dibenzofuranboronic acid.

$^1$HNMR (400 MHz, DMSO-d$_6$) δ 13.67 (s, 1H), 11.45 (s, 1H), 9.07 (d, 1H), 8.89 (d, 1H), 8.24 (m, 2H), 7.89 (m, 1H), 7.76 (d, 1H), 7.56 (m, 3H), 7.45 (m, 1H), 6.90 (m, 1H), 6.21 (m, 1H).

MS m/z 351 [M+1].

Example 99

3-(4-{[(5-chlorothien-2-yl)methyl]sulfonyl}-1H-pyrrol-2-yl)-1H-pyrazolo[3,4-b]pyridine

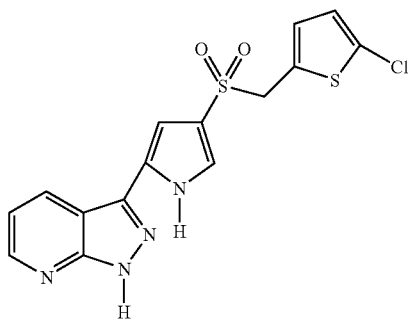

MS m/z 379 [M+1].

Example 100

3-{4-[(4-phenylpiperazin-1-yl)sulfonyl]-1H-pyrrol-2-yl}-1H-pyrazolo[3,4-b]pyridine

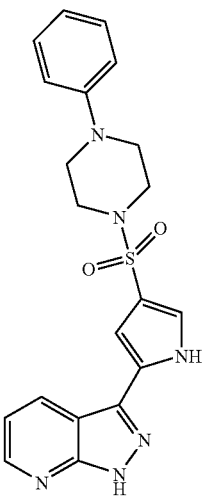

$^1$HNMR (400 MHz, DMSO-d$_6$) δ 13.77 (s, 1H), 12.45 (s, 1H), 8.56 (m, 2H), 7.39 (s, 1H), 7.16 (m, 3H), 7.01 (s, 1H), 6.91 (m, 2H), 6.74 (m, 1H), 3.21 (t, 4H), 3.02 (t, 4H).

MS m/z 409 [M+1].

Example 101

3-{4-[(4-pyridin-2-ylpiperazin-1-yl)sulfonyl]-1H-pyrrol-2-yl}1H-pyrazolo[3,4-b]pyridine

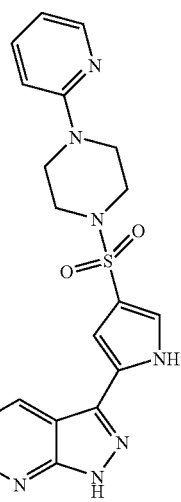

MS m/z 410 [M+1].

Example 102

5-[3-(benzyloxy)phenyl]-3-(1H-pyrrol-2-yl)-1H-pyrazolo[3,4-b]pyridine

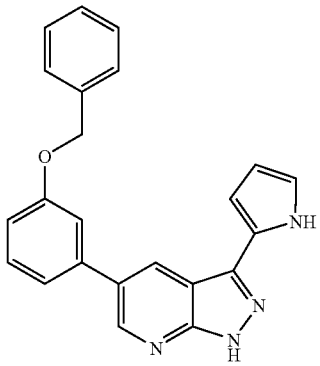

Obtained by Suzuki coupling with 3-benzyloxybenzeneboronic acid.

$^1$HNMR (400 MHz, DMSO-d$_6$) δ 13.56 (s, 1H), 11.45 (s, 1H), 8.8 (d, 1H), 8.6 (d, 1H), 7.49 (m, 5H), 7.40 (m, 3H), 7.15 (m, 1H), 6.88 (m, 2H), 6.20 (m, 1H), 5.22 (s, 2H).
MS m/z 367 [M+1].

Example 103

5-[4-(benzyloxy)phenyl]-3-(1H-pyrrol-2-yl)-1H-pyrazolo[3,4-b]pyridine

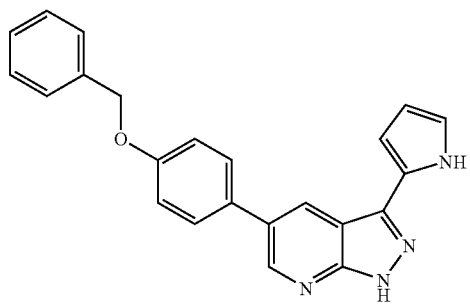

Obtained by Suzuki coupling with 4-benzyloxybenzeneboronic acid.
MS m/z 367 [M+1].

Example 104

5-[4-(benzyloxy)phenyl]-3-(1H-pyrrol-2-yl)-1H-pyrazolo[3,4-b]pyridine

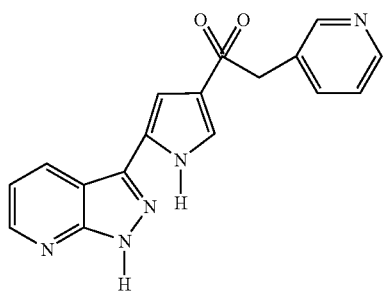

MS m/z 340 [M+1].

Example 105

3-{4-[3-Chloro-4-(2-morpholin-4-yl-ethoxy)-phenyl-methanesulfonyl]-1H-pyrrol-2-yl}-1H-pyrazolo[3,4-b]pyridine

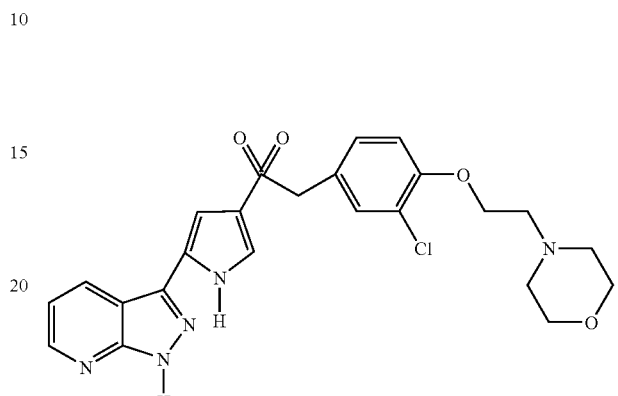

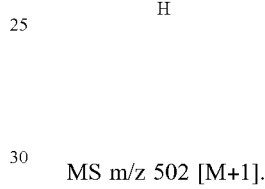

MS m/z 502 [M+1].

Example 106

2-[4-(4-Nitro-phenylmethanesulfonyl)-2-(1H-pyrazolo[3,4-b]pyridin-3-yl)-pyrrol-1-yl]-N-(2-morpholin-4-yl-ethyl)-acetamide

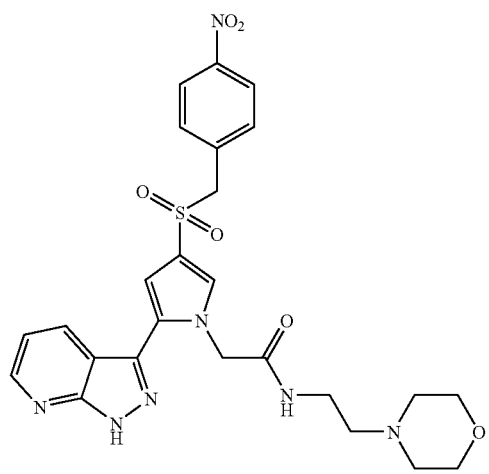

Example 107

5-(1H-Pyrazolo[3,4-b]pyridin-3-yl)-1H-pyrrole-3-sulfonic acid (4-chloro-benzyl)-(2-diethylamino-ethyl)-amide

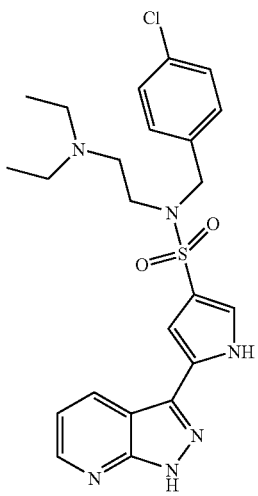

¹HNMR (400 MHz, DMSO-d₆) δ 13.77 (s, 1H), 12.45 (s, 1H), 8.56 (m, 2H), 7.43 (d, 1H), 7.40 (s, 4H), 7.26 (m, 1H), 7.1 (m, 1H), 4.30 (s, 2H), 3.06 (t, 2H), 2.27 (m, 6H), 0.8 (t, 6H)

MS m/z 487 [M+1].

Example 108

5-(4'-chloro-1,1'-biphenyl-3-yl)-3-(1H-pyrrol-2-yl)-1H-pyrazolo[3,4-b]pyridine

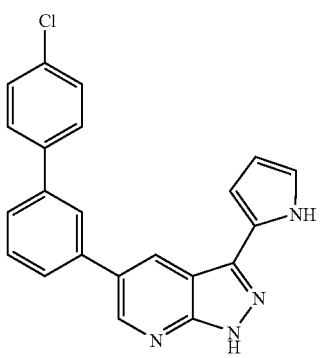

MS m/z 371 [M+1].

Example 109

N-(4-chlorobenzyl)-4,5-dimethyl-2-(1H-pyrazolo[3,4-b]pyridin-3-yl)-1H-pyrrole-3-carboxamide

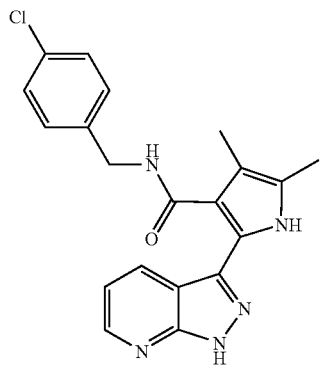

Obtained using the same method for example 2. N-(4-chlorobenzyl)-4,5-dimethyl-2-pyrrole-3-carboxamide was made according to Tetrahedron Lett. (1975), (40), 3487.
MS m/z 380 [M+1].

Example 110

3-{1-(2-morpholin-4-ylethyl)-4-[(4-nitrobenzyl)sulfonyl]-1H-pyrrol-2-yl}-1H-pyrazolo[3,4-b]pyridine

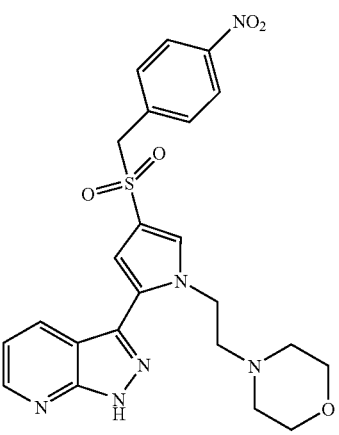

¹HNMR (400 MHz, DMSO-d₆) δ 13.86 (s, 1H), 8.59 (m, 1H), 8.30 (m, 1H), 8.17 (m, 2H), 7.47 (m, 2H), 7.43 (s, 1H), 7.25 (m, 1H), 6.87 (s, 1H), 4.82 (s, 2H), 4.47 (t, 2H), 3.37 (t, 4H), 2.48 (t, 2H), 2.27 (t, 4H).
MS m/z 497 [M+1].

Biological Evaluation

It will be appreciated that, in any given series of compounds, a range of biological activities will be observed. The following assays may be employed to select those compounds demonstrating the optimal degree of the desired activity.

PAK4 Kinase Activity

The present invention uses a biochemical-based cell lysate assay and a radioactive method to monitor, record and detect changes in phosphorylation of total GEF-H1 protein and GEF-H1-derived peptides by PAK4. In the cellular assay, phosphospecific antibodies to GEF-H1 are used to detect the presence of phosphorylated GEF-H1 in cell lysate preparations. Antibodies that are specific to GEF-H1 can be generated by any one of a number of techniques. For example, antibodies can be produced in rabbits. See, Nims et al., *Lab Anim. Sci.*, 23(3):391–6, 1973. Antibodies can be raised against epitopes that are unique or specific to a particular protein. For instance, one may raise antibodies against the KLH-conjugated peptide CSGDRRRAGPE-KRPKSS, as previously demonstrated for PAK4. See, Hashimura et al., *J. Immunol. Methods*, 55(3):375–87, 1982.

Measuring PAK4 Kinase Activity in Whole Cells Using ELISA

The level of PAK4-dependent phosphorylation of GEF-H1b can be determined by monitoring the binding of a phosphospecific antibody to GEF-H1b according to the following protocol. ELISA plates (Corning, 96 well plates, Cat. # 25805-96) were pre-coated with anti-HA monoclonal antibody at 5 mg/ml in PBS, using 100 ml final volume per well and stored overnight at 4° C. The coating buffer was then removed and replaced with blocking buffer (2% BSA in TBST) and the entire plate then shaken at room temperature for 60 minutes.

Tissue culture plates were then coated with poly-L-lysine, using 50 ml per well and then incubated at 37° C. for 30 minutes. The plates were then rinsed with PBS, extra liquid aspirated off and allowed to dry fully before use. When dry, TR-293-KDG cells were seeded into each well at $2\times10^{+4}$ cells per well in a 100 ml volume of DMEM and 10% Clontech-approved FBS, and left to incubate at room temperature for at least 2 hours. At that time, the medium was removed and replaced with 100 ml of low-serum medium (DMEM, 0.2% BSA and 1% Clontech-approved FBS), that was supplemented with 1 mg/ml of doxycycline. The negative control wells were not treated with doxycycline.

The next day, candidate substances were diluted as required in a solution containing 0.2% BSA, 10 mM HEPES and 1 mg/ml of doxycycline. A candidate substance were diluted by first preparing a 10 mM stock of the substance in 100% DMSO. 5 ml of that solution was then added to 15 ml of DMSO to prepare a 2.5 mM (50× concentration) solution. 6 ml of this final solution was then transferred to a well of a polypropylene plate, to which 300 ml of medium was added. 100 ml of the solution in the well was then added to each well containing cells, by removing the medium coating the cells and the solution containing the dilutions of the candidate substance gently added.

Fresh HNTG$^{plus}$ solution was then prepared by adding 1 tablet of "complete mini" protease inhibitor cocktail (Roche) to 10 ml water, 200 ml of b-glycerophosphate (final concentration, 1M), 100 ml of NaF (final concentration, 1M), and 10 ml of Na$_3$VO$_4$ (final concentration, 1M) and kept on ice. After the cells had been incubating for 3 hours with the diluted candidate substance, the medium was removed and the plate transferred onto ice. 100 ml of the fresh HNTG$^{plus}$ solution was then added to each well containing cells and shaken in a cold room for 10 minutes. During this time, the BSA from the ELISA plates was pipetted off and washed twice with TBST.

50 ml of a cell lysate was then transferred from the tissue culture plate to a washed well of the ELISA plate and shaken at room temperature for 60 minutes. Then, the cell lysate was removed and the wells of the ELISA plate washed three times with TBST. 100 ml of freshly-diluted anti-pGEF antibody (1:5000) was then transferred to each well of the ELISA plate and shaken at room temperature for 60 minutes. The antibody solution was removed and the wells washed four times with TBST. Then, 100 ml of freshly-diluted HRP-GaR (1:10,000) was added to each well of the ELISA plate and shaken at room temperature for 45 minutes. This solution was then removed and the wells washed four times with TBST, followed by one wash with PBS. ABTS solution was then added to the plate at 100 ml per well. The ELISA plate was then incubated at room temperature and shaken for between 10 and 20 minutes.

After that time, the ELISA plate was placed onto a Tecan Sunrise plate reader and measurements recorded using a measurement filter 405 nm with a reference filter of 620 nm.

Measuring the In Vitro Kinase Activity of Human PAK4 Using a Scintillation Proximity Assay The Scintillation Proximity Assay (SPA) is used to analyze protein serine/threonine kinase activity of PAK4 in vitro. The protocol involved adding 10 ml of inhibitor solution to each well of a flexiplate (Wallac 96-well polyethylene terephthalate ("flexi") plate, Cat. # 1450-401), using 10 ml of 5% DMSO for positive and negative controls.

PAK4 enzyme was added to the wells of the flexiplate at concentrations that were determined empirically. PAK4 enzyme was purified from BL21 cells. At the time of this experiment, the concentration of PAK4 kinase enzyme added to the wells was 0.1 m g per well in a volume of 20 ml. The concentration will vary with various preparations of enzyme. Accordingly, the skilled artisan would know how to titrate the enzyme preparation and determine a timecourse of linear kinase activity for particular preparations of the kinase. 20 ml of 0.5M EDTA is added to the negative control wells. The substrate was a PAK4 peptide that is known to be phosphorylated by PAK enzyme, consisting of the structure, biotin-LC-LC-RRKSLVG(pT)PYWMAPE (SEQ ID NO. 19)

The eighth amino acid of the PAK4 peptide, threonine, was a phosphothreonine, and the entire peptide was dissolved in water to a final concentration of 5 mg/ml and stored at –80° C. in 100 ml aliquots until needed. However, any peptide that is believed to be, or is, phosphorylated as a substrate by PAK kinase (e.g. PAK4) can be used instead of the PAK4 peptide. For instance, the GEF-H1b peptides represented by SEQ ID NOs. 3 and 4 can be used as a PAK4 substrate.

2.5× kinase buffer was used to facilitate PAK4 kinase activity and contained working concentrations per well of 50 mM HEPES (pH 7.4), 12.5 mM of MgCl$_2$, 375 mM KCl and 2.5 mM NaF. Typically, 10 ml of kinase buffer is sufficient for approximately 4.5 plates of reactions. The final concentrations of these constituents, following additions of candidate substance and ATP, are 20 mM HEPES (pH 7.4), 5 mM MgCl$_2$, 150 mM KCl and 1.0 mM NaF.

To start the kinase reaction, 20 ml of PAK4 biotinylated peptide/ATP solution was added to the wells of the plate and incubated at room temperature for 30 minutes, without shaking, and positioned behind a reactive shield. The peptide/ATP solution contained working concentrations (i.e., concentrations per well) of 1.4 mM cold (i.e., non-radioactive) ATP, 0.1 m g per well of Paktide and 0.33 m Ci per well of radiolabelled, g $^{33}$P-ATP (NEN Easy-Tide, Cat. # NEG602H). After 30 minutes, 200 ml of stop solution was added to each well and the plate allowed to stand for at least 15 minutes. "Stop" solution contained working concentrations per well of 50 m M ATP (unlabeled), 5 mM EDTA, 0.1% Triton X-100 and 0.5 mg of SPA beads, made up in PBS buffer solution. PBS (Dulbecco's Phosphate-Buffered Saline) without magnesium or calcium was obtained from Gibco BRL (Cat. # 14190-144). The beads were obtained from Amersham (Amersham streptavidin-coated polyvinyltoluene SPA beads, Cat. # NIF 1077). The beads were reconstituted in PBS without magnesium or calcium to a stock concentration of 20 mg/ml and stored at 4° C.

The plate was then centrifuged/spun at 2300 rpm for between 10 and 15 minutes and then transferred to a Trilux plate reader and the radioactivity counts recorded accordingly.

Assay Procedures

The following in vitro assays may be used to determine the level of activity and effect of the different compounds of the present invention on one or more of the PKs. Similar assays can be designed along the same lines for any PK using techniques well known in the art.

Several of the assays described herein are performed in an ELISA (Enzyme-Linked Immunosorbent Sandwich Assay) format (Voller, et al., 1980, "Enzyme-Linked Immunosorbent Assay," Manual of Clinical Immunology, 2d ed., Rose and Friedman, Am. Soc. Of Microbiology, Washington, D.C., pp. 359–371). The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphorylated residue compared with control cells that were not contacted with a test compound.

The presently preferred protocols for conducting the ELISA experiments for specific PKs is provided below. However, adaptation of these protocols for determining the activity of compounds against other STKs, as well as for CTKs and RTKs, is well within the scope of knowledge of those skilled in the art. Other assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as 5-bromodeoxyuridine (BrdU) or $H^3$-thymidine is added. The amount of labeled DNA is detected with either an anti-BrdU antibody or by measuring radioactivity and is compared to control cells not contacted with a test compound.

GST-FLK-1 Bioassay

This assay analyzes the tyrosine kinase activity of GST-Flk1 on poly(glu-tyr) peptides.

Materials and Reagents:
1. Corning 96-well ELISA plates (Corning Catalog No. 25805-96).
2. poly(glu-tyr) 4:1, lyophilizate (Sigma Catalog No. P0275), 1 mg/ml in sterile PBS.
3. PBS Buffer: for 1 L, mix 0.2 g $KH_2PO_4$, 1.15 g $Na_2HPO_4$, 0.2 g KCl and 8 g NaCl in approx. 900 ml $dH_2O$. When all reagents have dissolved, adjust the pH to 7.2 with HCl. Bring total volume to 1 L with $dH_2O$.
4. PBST Buffer: to 1 L of PBS Buffer, add 1.0 ml Tween-20.
5. TBB–Blocking Buffer: for 1 L, mix 1.21 g TRIS, 8.77 g NaCl, 1 ml TWEEN-20 in approximately 900 ml $dH_2O$. Adjust pH to 7.2 with HCl. Add 10 g BSA, stir to dissolve. Bring total volume to 1 L with $dH_2O$. Filter to remove particulate matter.
6. 1% BSA in PBS: add 10 g BSA to approx. 990 ml PBS buffer, stir to dissolve. Adjust total volume to 1 L with PBS buffer, filter to remove particulate matter.
7. 50 mM Hepes pH 7.5.
8. GST-Flk1cd purified from sf9 recombinant baculovirus transformation (SUGEN, Inc.).
9. 4% DMSO in $dH_2O$.
10. 10 mM ATP in $dH_2O$.
11. 40 mM $MnCl_2$
12. Kinase Dilution Buffer (KDB): mix 10 ml Hepes (pH 7.5), 1 ml 5M NaCl, 40 μL 100 mM sodium orthovanadate and 0.4 ml of 5% BSA in $dH_2O$ with 88.56 ml $dH_2O$.
13. NUNC 96-well V bottom polypropylene plates, Applied Scientific Catalog # AS-72092
14. EDTA: mix 14.12 g ethylenediaminetetraacetic acid (EDTA) with approx. 70 ml $dH_2O$. Add 10 N NaOH until EDTA dissolves. Adjust pH to 8.0. Adjust total volume to 100 ml with $dH_2O$.
15. 1° and 2° Antibody Dilution Buffer: mix 10 ml of 5% BSA in PBS buffer with 89.5 ml TBST.
16. Anti-phosphotyrosine rabbit polyclonal antisera (SUGEN, Inc.)
17. Goat anti-rabbit HRP conjugate.
18. ABST solution: To approx. 900 ml $dH_2O$ add 19.21 g citric acid and 35.49 g $Na_2HPO_4$. Adjust pH to 4.0 with phosphoric acid. Add 2,2'-Azinobis(3-ethyl-benzthiazoline-6-sulfonic acid (ABTS, Sigma, Cat. No. A-1888, hold for approx. ½ hour, filter.
19. 30% Hydrogen Peroxide.
20. ABST/$H_2O_2$: add 3 μl of $H_2O_2$ to 15 ml of ABST solution.
21. 0.2 M HCl.

Procedure:
1. Coat Corning 96-well ELISA plates with 2 μg of polyEY in 100 μl PBS/well, hold at room temperature for 2 hours or at 4° C. overnight. Cover plates to prevent evaporation.
2. Remove unbound liquid from wells by inverting plate. Wash once with TBST. Pat the plate on a paper towel to remove excess liquid.
3. Add 100 μl of 1% BSA in PBS to each well. Incubate, with shaking, for 1 hr. at room temperature.
4. Repeat step 2.
5. Soak wells with 50 mM HEPES (pH7.5, 150 μl/well).
6. Dilute test compound with $dH_2O$/4% DMSO to 4 times the desired final assay concentration in 96-well polypropylene plates.
7. Add 25 μl diluted test compound to each well of ELISA plate. In control wells, place 25 μl of $dH_2O$/4% DMSO.
8. Dilute GST-Flk1 0.005 μg (5 ng)/well in KDB.
9. Add 50 μl of diluted enzyme to each well.
10. Add 25 μl 0.5 M EDTA to negative control wells.
11. Add 25 μl of 40 mM $MnCl_2$ with 4×ATP (2 μM) to all wells (100 μl final volume, 0.5 μM ATP final concentration in each well).
12. Incubate, with shaking, for 15 minutes at room temperature.
13. Stop reaction by adding 25 μl of 500 mM EDTA to each well.
14. Wash 3× with TBST and pat plate on paper towel to remove excess liquid.

15. Add 100 µl per well anti-phosphotyrosine antisera, 1:10,000 dilution in antibody dilution buffer. Incubate, with shaking, for 90 min. at room temperature.
16. Wash as in step 14.
17. Add 100 µl/well of goat anti-rabbit HRP conjugate (1:6,000 in antibody dilution buffer). Incubate, with shaking, for 90 minutes are room temperature.
18. Wash as in Step 14.
19. Add 100 µl room temperature ABST/$H_2O_2$ solution to each well.
20. Incubate, with shaking for 15 to 30 minutes at room temperature.
21. If necessary, stop reaction by adding 100 µl of 0.2 M HCl to each well.
22. Read results on Dynatech MR7000 ELISA reader with test filter at 410 nM and reference filter at 630 nM.

PYK2 Bioassay

This assay is used to measure the in vitro kinase activity of HA epitope-tagged full length pyk2 (FL.pyk2-HA) in an ELISA assay.

Materials and Reagents:
1. Corning 96-well ELISA plates.
2. 12CA5 monoclonal anti-HA antibody (SUGEN, Inc.)
3. PBS (Dulbecco's Phosphate-Buffered Saline (Gibco Catalog # 450-1300EB)
4. TBST Buffer: for 1 L, mix 8.766 g NaCl, 6.057 g TRIS and 1 ml of 0.1% Triton X-100 in approx. 900 ml $dH_2O$. Adjust pH to 7.2, bring volume to 1 L.
5. Blocking Buffer: for 1 L, mix 100 g 10% BSA, 12.1 g 100 mM TRIS, 58.44 g 1M NaCl and 10 mL of 1% TWEEN-20.
6. FL.pyk2-HA from sf9 cell lysates (SUGEN, Inc.).
7. 4% DMSO in MilliQue $H_2O$.
8. 10 mM ATP in $dH_2O$.
9. 1M $MnCl_2$.
10. 1M $MgCl_2$.
11. 1M Dithiothreitol (DTT).
12. 10× Kinase buffer phosphorylation: mix 5.0 ml 1M Hepes (pH 7.5), 0.2 ml 1M $MnCl_2$, 1.0 ml 1 M $MgCl_2$, 1.0 ml 10% Triton X-100 in 2.8 ml $dH_2O$. Just prior to use, add 0.1 ml 1M DTT.
13. NUNC 96-well V bottom polypropylene plates.
14. 500 mM EDTA in $dH_2O$.
15. Antibody dilution buffer: for 100 mL, 1 mL 5% BSA/PBS and 1 mL 10% Tween-20 in 88 mL TBS.
16. HRP-conjugated anti-Ptyr (PY99, Santa Cruz Biotech Cat. No. SC-7020).
17. ABTS, Moss, Cat. No. ABST-2000.
18. 10% SDS.

Procedure:
1. Coat Corning 96 well ELISA plates with 0.5 µg per well 12CA5 anti-HA antibody in 100 µl PBS. Store overnight at 4° C.
2. Remove unbound HA antibody from wells by inverting plate. Wash plate with $dH_2O$. Pat the plate on a paper towel to remove excess liquid.
3. Add 150 µl Blocking Buffer to each well. Incubate, with shaking, for 30 min at room temperature.
4. Wash plate 4× with TBS-T.
5. Dilute lysate in PBS (1.5 µg lysate/100 µl PBS).
6. Add 100 µl of diluted lysate to each well. Shake at room temperature for 1 hr.
7. Wash as in step 4.
8. Add 50 µl of 2× kinase Buffer to ELISA plate containing captured pyk2-HA.
9. Add 25 µL of 400 µM test compound in 4% DMSO to each well. For control wells use 4% DMSO alone.
10. Add 25 µL of 0.5 M EDTA to negative control wells.
11. Add 25 µl of 20 µM ATP to all wells. Incubate, with shaking, for 10 minutes.
12. Stop reaction by adding 25 µl 500 mM EDTA (pH 8.0) to all wells.
13. Wash as in step 4.
14. Add 100 µL HRP conjugated anti-Ptyr diluted 1:6000 in Antibody Dilution Buffer to each well. Incubate, with shaking, for 1 hr. at room temperature.
15. Wash plate 3× with TBST and 1× with PBS.
16. Add 100 µL of ABST solution to each well.
17. If necessary, stop the development reaction by adding 20 µL 10% SDS to each well.
18. Read plate on ELISA reader with test filter at 410 nM and reference filter at 630 nM.

FGFR1 Bioassay

This assay is used to measure the in vitro kinase activity of FGF1-R in an ELISA assay.

Materials and Reagents:
1. Costar 96-well ELISA plates (Corning Catalog # 3369).
2. Poly(Glu-Tyr) (Sigma Catalog # P0275).
3. PBS (Gibco Catalog # 450-1300EB)
4. 50 mM Hepes Buffer Solution.
5. Blocking Buffer (5% BSA/PBS).
6. Purified GST-FGFR1 (SUGEN, Inc.)
7. Kinase Dilution Buffer. Mix 500 µl 1M Hepes (GIBCO), 20 µl 5% BSA/PBS, 10 µl 100 mM sodium orthovanadate and 50 µl 5M NaCl.
8. 10 mM ATP
9. ATP/$MnCl_2$ phosphorylation mix: mix 20 µL ATP, 400 µL 1M $MnCl_2$ and 9.56 ml $dH_2O$.
10. NUNC 96-well V bottom polypropylene plates (Applied Scientific Catalog # AS-72092).
11. 0.5M EDTA.
12. 0.05% TBST Add 500 µL TWEEN to 1 liter TBS.
13. Rabbit polyclonal anti-phosphotyrosine serum (SUGEN, Inc.).
14. Goat anti-rabbit IgG peroxidase conjugate (Biosource, Catalog # ALI0404).
15. ABTS Solution.
16. ABTS/$H_2O_2$ solution.

Procedure:
1. Coat Costar 96 well ELISA plates with 1 µg per well Poly(Glu-Tyr) in 100 µl PBS. Store overnight at 4° C.
2. Wash coated plates once with PBS.
3. Add 150 µL of 5% BSA/PBS Blocking Buffer to each well. Incubate, with shaking, for 1 hr at room temperature.
4. Wash plate 2× with PBS, then once with 50 mM Hepes. Pat plates on a paper towel to remove excess liquid and bubbles.
5. Add 25 µL of 0.4 mM test compound in 4% DMSO or 4% DMSO alone (controls) to plate.
6. Dilute purified GST-FGFR1 in Kinase Dilution Buffer (5 ng kinase/50 ul KDB/well).
7. Add 50 µL of diluted kinase to each well.
8. Start kinase reaction by adding 25 µl/well of freshly prepared ATP/Mn++ (0.4 ml 1M $MnCl_2$, 40 µL 10 mM ATP, 9.56 ml $dH_2O$), freshly prepared).
9. Stop reaction with 25 µL of 0.5M EDTA.
10. Wash plate 4× with fresh TBST.
11. Make up Antibody Dilution Buffer: For 50 ml, mix 5 ml of 5% BSA, 250 µl of 5% milk and 50 µl of 100 mM sodium vanadate, bring to final volume with 0.05% TBST.

12. Add 100 μl per well of anti-phosphotyrosine (1:10000 dilution in ADB). Incubate, with shaking for 1 hr. at room temperature.
13. Wash as in step 10.
14. Add 100 μl per well of Biosource Goat anti-rabbit IgG peroxidase conjugate (1:6000 dilution in ADB). Incubate, with shaking for 1 hr. at room temperature.
15. Wash as in step 10 and then with PBS to remove bubbles and excess TWEEN.
16. Add 100 μl of ABTS/$H_2O_2$ solution to each well.
17. Incubate, with shaking, for 10 to 20 minutes. Remove any bubbles.
18. Read assay on Dynatech MR7000 ELISA reader: test filter at 410 nM, reference filter at 630 nM.

EGFR Bioassay

This assay is used to the in vitro kinase activity of EGFR in an ELISA assay.

Materials and Reagents:
1. Corning 96-well ELISA plates.
2. SUMO1 monoclonal anti-EGFR antibody (SUGEN, Inc.).
3. PBS.
4. TBST Buffer.
5. Blocking Buffer: for 100 ml, mix 5.0 g Carnation® Instant Non-fat Milk with 100 ml of PBS.
6. A431 cell lysate (SUGEN, Inc.).
7. TBS Buffer.
8. TBS+10% DMSO: for 1L, mix 1.514 g TRIS, 2.192 g NaCl and 25 ml DMSO; bring to 1 liter total volume with $dH_2O$.
9. ATP (Adenosine-5'-triphosphate, from Equine muscle, Sigma Cat. No. A-5394), 1.0 mM solution in $dH_2O$. This reagent should be made up immediately prior to use and kept on ice.
10. 1.0 mM $MnCl_2$.
11. ATP/$MnCl_2$ phosphorylation mix: for 10 ml, mix 300 μl of 1 mM ATP, 500 μl $MnCl_2$ and 9.2 ml $dH_2O$. Prepare just prior to use, keep on ice.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. 30% Hydrogen peroxide.
18. ABTS/$H_2O_2$.
19. 0.2 M HCl.

Procedure:
1. Coat Corning 96 well ELISA plates with 0.5 μg SUMO1 in 100 μl PBS per well, hold overnight at 4° C.
2. Remove unbound SUMO1 from wells by inverting plate to remove liquid. Wash 1× with $dH_2O$. Pat the plate on a paper towel to remove excess liquid.
3. Add 150 μl of Blocking Buffer to each well. Incubate, with shaking, for 30 min. at room temperature.
4. Wash plate 3× with deionized water, then once with TBST. Pat plate on a paper towel to remove excess liquid and bubbles.
5. Dilute lysate in PBS (7 μg lysate/100 μl PBS).
6. Add 100 μl of diluted lysate to each well. Shake at room temperature for 1 hr.
7. Wash plates as in 4, above.
8. Add 120 μl TBS to ELISA plate containing captured EGFR.
9. Dilute test compound 1:10 in TBS, place in well 10. Add 13.5 μl diluted test compound to ELISA plate. To control wells, add 13.5 μl TBS in 10% DMSO.
11. Incubate, with shaking, for 30 minutes at room temperature.
12. Add 15 μl phosphorylation mix to all wells except negative control well. Final well volume should be approximately 150 μl with 3 μM ATP/5 mM $MnCl_2$ final concentration in each well. Incubate with shaking for 5 minutes.
13. Stop reaction by adding 16.5 μl of EDTA solution while shaking. Shake for additional 1 min.
14. Wash 4× with deionized water, 2× with TBST.
15. Add 100 μl anti-phosphotyrosine (1:3000 dilution in TBST) per well. Incubate, with shaking, for 30–45 min. at room temperature.
16. Wash as in 4, above.
17. Add 100 μl Biosource Goat anti-rabbit IgG peroxidase conjugate (1:2000 dilution in TBST) to each well. Incubate with shaking for 30 min. at room temperature.
18. Wash as in 4, above.
19. Add 100 μl of ABTS/$H_2O_2$ solution to each well.
20. Incubate 5 to 10 minutes with shaking. Remove any bubbles.
21. If necessary, stop reaction by adding 100 μl 0.2 M HCl per well.
22. Read assay on Dynatech MR7000 ELISA reader: test filter at 410 nM, reference filter at 630 nM.

PDGFR Bioassay

This assay is used to the in vitro kinase activity of PDGFR in an ELISA assay.

Materials and Reagents:
1. Corning 96-well ELISA plates
2. 28D4C10 monoclonal anti-PDGFR antibody (SUGEN, Inc.).
3. PBS.
4. TBST Buffer.
5. Blocking Buffer (same as for EGFR bioassay).
6. PDGFR-β expressing NIH 3T3 cell lysate (SUGEN, Inc.).
7. TBS Buffer.
8. TBS+10% DMSO.
9. ATP.
10. $MnCl_2$.
11. Kinase buffer phosphorylation mix: for 10 ml, mix 250 μl 1M TRIS, 200 μl 5M NaCl, 100 μl 1M $MnCl_2$ and 50 μl 100 mM Triton X-100 in enough $dH_2O$ to make 10 ml.
12. NUNC 96-well V bottom polypropylene plates.
13. EDTA.
14. Rabbit polyclonal anti-phosphotyrosine serum (SUGEN, Inc.).
15. Goat anti-rabbit IgG peroxidase conjugate (Biosource Cat. No. ALI0404).
16. ABTS.
17. Hydrogen peroxide, 30% solution.
18. ABTS/$H_2O_2$.
19. 0.2 M HCl.

Procedure:
1. Coat Corning 96 well ELISA plates with 0.5 μg 28D4C10 in 100 μl PBS per well, hold overnight at 4° C.
2. Remove unbound 28D4C 10 from wells by inverting plate to remove liquid. Wash 1× with $dH_2O$. Pat the plate on a paper towel to remove excess liquid.
3. Add 150 μl of Blocking Buffer to each well. Incubate for 30 min. at room temperature with shaking.

4. Wash plate 3× with deionized water, then once with TBST. Pat plate on a paper towel to remove excess liquid and bubbles.
5. Dilute lysate in HNTG (10 μg lysate/100 μl HNTG).
6. Add 100 μl of diluted lysate to each well. Shake at room temperature for 60 min.
7. Wash plates as described in Step 4.
8. Add 80 μl working kinase buffer mix to ELISA plate containing captured PDGFR.
9. Dilute test compound 1:10 in TBS in 96-well polypropylene plates.
10. Add 10 μl diluted test compound to ELISA plate. To control wells, add 10 μl TBS+10% DMSO. Incubate with shaking for 30 minutes at room temperature.
11. Add 10 μl ATP directly to all wells except negative control well (final well volume should be approximately 100 μl with 20 μM ATP in each well.) Incubate 30 minutes with shaking.
12. Stop reaction by adding 10 μl of EDTA solution to each well.
13. Wash 4× with deionized water, twice with TBST.
14. Add 100 μl anti-phosphotyrosine (1:3000 dilution in TBST) per well. Incubate with shaking for 30–45 min. at room temperature.
15. Wash as in Step 4.
16. Add 100 μl Biosource Goat anti-rabbit IgG peroxidase conjugate (1:2000 dilution in TBST) to each well. Incubate with shaking for 30 min. at room temperature.
17. Wash as in Step 4.
18. Add 100 μl of ABTS/$H_2O_2$ solution to each well.
19. Incubate 10 to 30 minutes with shaking. Remove any bubbles.
20. If necessary stop reaction with the addition of 100 μl 0.2 M HCl per well.
21. Read assay on Dynatech MR7000 ELISA reader with test filter at 410 nM and reference filter at 630 nM.

Cellular HER-2 Kinase Assay

This assay is used to measure HER-2 kinase activity in whole cells in an ELISA format.

Materials and Reagents:
1. DMEM (GIBCO Catalog #11965-092).
2. Fetal Bovine Serum (FBS, GIBCO Catalog #16000-044), heat inactivated in a water bath for 30 min. at 56° C.
3. Trypsin (GIBCO Catalog #25200-056).
4. L-Glutamine (GIBCO Catalog #25030-081).
5. HEPES (GIBCO Catalog #15630-080).
6. Growth Media: Mix 500 ml DMEM, 55 ml heat inactivated FBS, 10 ml HEPES and 5.5 ml L-Glutamine.
7. Starve Media: Mix 500 ml DMEM, 2.5 ml heat inactivated FBS, 10 ml HEPES and 5.5 ml L-Glutamine.
8. PBS.
9. Flat Bottom 96-well Tissue Culture Micro Titer Plates (Corning Catalog # 25860).
10. 15 cm Tissue Culture Dishes (Corning Catalog #08757148).
11. Corning 96-well ELISA Plates.
12. NUNC 96-well V bottom polypropylene plates.
13. Costar Transfer Cartridges for the Transtar 96 (Costar Catalog #7610).
14. SUMO 1: monoclonal anti-EGFR antibody (SUGEN, Inc.).
15. TBST Buffer.
16. Blocking Buffer: 5% Carnation Instant Milk® in PBS.
17. EGF Ligand: EGF-201, Shinko American, Japan. Suspend powder in 100 μL of 10 mM HCl. Add 100 uL 10 mM NaOH. Add 800 μL PBS and transfer to an Eppendorf tube, store at −20° C. until ready to use.
18. HNTG Lysis Buffer: For Stock 5×HNTG, mix 23.83 g Hepes, 43.83 g NaCl, 500 ml glycerol and 100 ml Triton X-100 and enough $dH_2O$ to make 1 L of total solution. For 1×HNTG*, mix 2 ml 5×HNTG, 100 μL 0.1M $Na_3VO_4$, 250 μL 0.2M $Na_4P_2O_7$ and 100 μL EDTA.
19. EDTA.
20. $Na_3VO_4$: To make stock solution, mix 1.84 g $Na_3VO_4$ with 90 ml $dH_2O$. Adjust pH to 10. Boil in microwave for one minute (solution becomes clear). Cool to room temperature. Adjust pH to 10. Repeat heating/cooling cycle until pH remains at 10.
21. 200 mM $Na_4P_2O_7$.
22. Rabbit polyclonal antiserum specific for phosphotyrosine (anti-Ptyr antibody, SUGEN, Inc.).
23. Affinity purified antiserum, goat anti-rabbit IgG antibody, peroxidase conjugate (Biosource Cat # ALI0404).
24. ABTS Solution.
25. 30% Hydrogen peroxide solution.
26. ABTS/$H_2O_2$.
27. 0.2 M HCl.

Procedure:
1. Coat Corning 96 well ELISA plates with SUMO1 at 1.0 μg per well in PBS, 100 μl final volume/well. Store overnight at 4° C.
2. On day of use, remove coating buffer and wash plate 3 times with $dH_2O$ and once with TBST buffer. All washes in this assay should be done in this manner, unless otherwise specified.
3. Add 100 μL of Blocking Buffer to each well. Incubate plate, with shaking, for 30 min. at room temperature. Just prior to use, wash plate.
4. Use EGFr/HER-2 chimera/3T3-C7 cell line for this assay.
5. Choose dishes having 80–90% confluence. Collect cells by trypsinization and centrifuge at 1000 rpm at room temperature for 5 min.
6. Resuspend cells in starve medium and count with trypan blue. Viability above 90% is required. Seed cells in starve medium at a density of 2,500 cells per well, 90 μL per well, in a 96 well microtiter plate. Incubate seeded cells overnight at 37° under 5% $CO_2$.
7. Start the assay two days after seeding.
8. Test compounds are dissolved in 4% DMSO. Samples are then further diluted directly on plates with starve-DMEM. Typically, this dilution will be 1:10 or greater. All wells are then transferred to the cell plate at a further 1:10 dilution (10 μl sample and media into 90 μl of starve media). The final DMSO concentration should be 1% or lower. A standard serial dilution may also be used.
9. Incubate under 5% $CO_2$ at 37° C. for 2 hours.
10. Prepare EGF ligand by diluting stock EGF (16.5 μM) in warm DMEM to 150 nM.
11. Prepare fresh HNTG* sufficient for 100 μL per well; place on ice.
12. After 2 hour incubation with test compound, add prepared EGF ligand to cells, 50 μL per well, for a final concentration of 50 nM. Positive control wells receive the same amount of EGF. Negative controls do not receive EGF. Incubate at 37° C. for 10 min.
13. Remove test compound, EGF, and DMEM. Wash cells once with PBS.
14. Transfer HNTG* to cells, 100 μL per well. Place on ice for 5 minutes. Meanwhile, remove blocking buffer from ELISA plate and wash.

15. Scrape cells from plate with a micropipettor and homogenize cell material by repeatedly aspirating and dispensing the HNTG* lysis buffer. Transfer lysate to a coated, blocked, washed ELISA plate.
16. Incubate, with shaking, at room temperature for 1 hr.
17. Remove lysate, wash. Transfer freshly diluted anti-Ptyr antibody (1:3000 in TBST) to ELISA plate, 100 µL per well.
18. Incubate, with shaking, at room temperature, for 30 min.
19. Remove anti-Ptyr antibody, wash. Transfer freshly diluted BIOSOURCE antibody to ELISA plate (1:8000 in TBST, 100 µL per well).
20. Incubate, with shaking, at room temperature for 30 min.
21. Remove BIOSOURCE antibody, wash. Transfer freshly prepared ABTS/$H_2O_2$ solution to ELISA plate, 100 µL per well.
22. Incubate, with shaking, for 5–10 minutes. Remove any bubbles.
23. Stop reaction by adding 100 µL of 0.2M HCl per well.
24. Read assay on Dynatech MR7000 ELISA reader with test filter set at 410 nM and reference filter at 630 nM.

Cdk2/Cyclin A Assay

This assay is used to measure the in vitro serine/threonine kinase activity of human cdk2/cyclin A in a Scintillation Proximity Assay (SPA).

Materials and Reagents.
1. Wallac 96-well polyethylene terephthalate (flexi) plates (Wallac Catalog # 1450-401).
2. Amersham Redivue [$\gamma^{33}$P] ATP (Amersham catalog #AH 9968).
3. Amersham streptavidin coated polyvinyltoluene SPA beads (Amersham catalog #RPNQ0007). The beads should be reconstituted in PBS without magnesium or calcium, at 20 mg/ml.
4. Activated cdk2/cyclin A enzyme complex purified from Sf9 cells (SUGEN, Inc.).
5. Biotinylated peptide substrate (Debtide). Peptide biotin-X-PKTPKKAKKL is dissolved in $dH_2O$ at a concentration of 5 mg/ml.
6. 20% DMSO in $dH_2O$.
7. Kinase buffer: for 10 ml, mix 9.1 ml $dH_2O$, 0.5 ml TRIS(pH 7.4), 0.2 ml 1M $MgCl_2$, 0.2 ml 10% NP40 and 0.02 ml 1M DTT, added fresh just prior to use.
8. 10 mM ATP in $dH_2O$.
9. 1M Tris, pH adjusted to 7.4 with HCl.
10. 1M $MgCl_2$.
11. 1M DTT.
12. PBS (Gibco Catalog # 14190-144).
13. 0.5M EDTA.
14. Stop solution: For 10 ml, mix 9.25 ml PBS, 0.05 ml 10 mM ATP, 0.1 ml 0.5 M EDTA, 0.1 ml 10% Triton X-100 and 1.5 ml of 50 mg/ml SPA beads.

Procedure:
1. Prepare solutions of test compounds at 4× the desired final concentration in 5% DMSO. Add 10 µL to each well. For positive and negative controls, use 10 µL 20% DMSO alone in wells.
2. Dilute the peptide substrate (deb-tide) 1:250 with $dH_2O$ to give a final concentration of 0.02 mg/ml.
3. Mix 24 µL 0.1 mM ATP with 24 µCi $\gamma^{33}$P ATP and enough $dH_2O$ to make 600 µL.
4. Mix diluted peptide and ATP solutions 1:1 (600 µL+600 µL per plate). Add 10 µL of this solution to each well.
5. Dilute 5 µL of cdk2/cyclin A solution into 2.1 ml 2× kinase buffer (per plate). Add 20 µL enzyme per well. For negative controls, add 20 µL 2× kinase buffer without enzyme.
6. Mix briefly on a plate shaker; incubate for 60 minutes.
7. Add 200 µL stop solution per well.
8. Let stand at least 10 min.
9. Spin plate at approx. 2300 rpm for 10–15 min.
10. Count plate on Trilux reader.

Met Transphosphorylation Assay

This assay is used to measure phosphotyrosine levels on a poly(glutamic acid:tyrosine, 4:1) substrate as a means for identifying agonists/antagonists of met transphosphorylation of the substrate.

Materials and Reagents:
1. Corning 96-well ELISA plates, Corning Catalog # 25805-96.
2. Poly(glu-tyr), 4:1, Sigma, Cat. No; P 0275.
3. PBS, Gibco Catalog # 450-1300EB
4. 50 mM HEPES
5. Blocking Buffer: Dissolve 25 g Bovine Serum Albumin, Sigma Cat. No A-7888, in 500 ml PBS, filter through a 4 µm filter.
6. Purified GST fusion protein containing the Met kinase domain, SUGEN, Inc.
7. TBST Buffer.
8. 10% aqueous (MilliQue $H_2O$) DMSO.
9. 10 mM aqueous ($dH_2O$) Adenosine-5'-triphosphate, Sigma Cat. No. A-5394.
10. 2× Kinase Dilution Buffer: for 100 ml, mix 10 mL 1M HEPES at pH 7.5 with 0.4 mL 5% BSA/PBS, 0.2 mL 0.1 M sodium orthovanadate and 1 mL 5M sodium chloride in 88.4 mL $dH_2O$.
11. 4×ATP Reaction Mixture: for 10 mL, mix 0.4 mL 1 M manganese chloride and 0.02 mL 0.1 M ATP in 9.56 mL $dH_2O$.
12. 4× Negative Controls Mixture: for 10 mL, mix 0.4 mL 1 M manganese chloride in 9.6 mL $dH_2O$.
13. NUNC 96-well V bottom polypropylene plates, Applied Scientific Catalog # S-72092
14. 500 mM EDTA.
15. Antibody Dilution Buffer: for 100 mL, mix 10 mL 5% BSA/PBS, 0.5 mL 5% Carnation® Instant Milk in PBS and 0.1 mL 0.1 M sodium orthovanadate in 88.4 mL TBST.
16. Rabbit polyclonal antophosphotyrosine antibody, SUGEN, Inc.
17. Goat anti-rabbit horseradish peroxidase conjugated antibody, Biosource, Inc.
18. ABTS Solution: for 1 L, mix 19.21 g citric acid, 35.49 g $Na_2HPO_4$ and 500 mg ABTS with sufficient $dH_2O$ to make 1 L.
19. ABTS/$H_2O_2$: mix 15 mL ABST solution with 2 µL $H_2O_2$ five minutes before use.
20. 0.2 M HCl Procedure:
1. Coat ELISA plates with 2 µg Poly(Glu-Tyr) in 100 µL PBS, hold overnight at 4° C.
2. Block plate with 150 µL of 5% BSA/PBS for 60 min.
3. Wash plate twice with PBS then once with 50 mM Hepes buffer pH 7.4.
4. Add 50 µl of the diluted kinase to all wells. (Purified kinase is diluted with Kinase Dilution Buffer. Final concentration should be 10 ng/well.)

5. Add 25 μL of the test compound (in 4% DMSO) or DMSO alone (4% in dH₂O) for controls to plate.
6. Incubate the kinase/compound mixture for 15 minutes.
7. Add 25 μL of 40 mM MnCl₂ to the negative control wells.
8. Add 25 μL ATP/MnCl₂ mixture to the all other wells (except the negative controls). Incubate for 5 min.
9. Add 25 μL 500 mM EDTA to stop reaction.
10. Wash plate 3× with TBST.
11. Add 100 μL rabbit polyclonal anti-Ptyr diluted 1:10,000 in Antibody Dilution Buffer to each well. Incubate, with shaking, at room temperature for one hour.
12. Wash plate 3× with TBST.
13. Dilute Biosource HRP conjugated anti-rabbit antibody 1:6,000 in Antibody Dilution buffer. Add 100 μL per well and incubate at room temperature, with shaking, for one hour.
14. Wash plate 1× with PBS.
15. Add 100 μl of ABTS/H₂O₂ solution to each well.
16. If necessary, stop the development reaction with the addition of 100 μl of 0.2M HCl per well.
17. Read plate on Dynatech MR7000 ELISA reader with the test filter at 410 nM and the reference filter at 630 nM.

BrdU Incorporation Assays

The following assays use cells engineered to express a selected receptor and then evaluate the effect of a compound of interest on the activity of ligand-induced DNA synthesis by determining BrdU incorporation into the DNA.

The following materials, reagents and procedure are general to each of the following BrdU incorporation assays. Variances in specific assays are noted.

General Materials and Reagents:
1. The appropriate ligand.
2. The appropriate engineered cells.
3. BrdU Labeling Reagent: 10 mM, in PBS, pH7.4 (Roche Molecular Biochemicals, Indianapolis, Ind.).
4. FixDenat: fixation solution (Roche Molecular Biochemicals, Indianapolis, Ind.).
5. Anti-BrdU-POD: mouse monoclonal antibody conjugated with peroxidase (Chemicon, Temecula, Calif.).
6. TMB Substrate Solution: tetramethylbenzidine (TMB, ready to use, Roche Molecular Biochemicals, Indianapolis, Ind.).
7. PBS Washing Solution: 1×PBS, pH 7.4.
8. Albumin, Bovine (BSA), fraction V powder (Sigma Chemical Co., USA).

General Procedure:
1. Cells are seeded at 8000 cells/well in 10% CS, 2 mM Gln in DMEM, in a 96 well plate. Cells are incubated overnight at 37° C. in 5% CO₂.
2. After 24 hours, the cells are washed with PBS, and then are serum-starved in serum free medium (0%CS DMEM with 0.1% BSA) for 24 hours.
3. On day 3, the appropriate ligand and the test compound are added to the cells simultaneously. The negative control wells receive serum free DMEM with 0.1% BSA only; the positive control cells receive the ligand but no test compound. Test compounds are prepared in serum free DMEM with ligand in a 96 well plate, and serially diluted for 7 test concentrations.
4. After 18 hours of ligand activation, diluted BrdU labeling reagent (1:100 in DMEM, 0.1% BSA) is added and the cells are incubated with BrdU (final concentration is 10 μM) for 1.5 hours.
5. After incubation with labeling reagent, the medium is removed by decanting and tapping the inverted plate on a paper towel. FixDenat solution is added (50 μl/well) and the plates are incubated at room temperature for 45 minutes on a plate shaker.
6. The FixDenat solution is removed by decanting and tapping the inverted plate on a paper towel. Milk is added (5% dehydrated milk in PBS, 200 μl/well) as a blocking solution and the plate is incubated for 30 minutes at room temperature on a plate shaker.
7. The blocking solution is removed by decanting and the wells are washed once with PBS. Anti-BrdU-POD solution is added (1:200 dilution in PBS, 1% BSA, 50 μl/well) and the plate is incubated for 90 minutes at room temperature on a plate shaker.
8. The antibody conjugate is removed by decanting and rinsing the wells 5 times with PBS, and the plate is dried by inverting and tapping on a paper towel.
9. TMB substrate solution is added (100 μl/well) and incubated for 20 minutes at room temperature on a plate shaker until color development is sufficient for photometric detection.
10. The absorbance of the samples are measured at 410 nm (in "dual wavelength" mode with a filter reading at 490 nm, as a reference wavelength) on a Dynatech ELISA plate reader.

EGF-Induced BrdU Incorporation Assay

Materials and Reagents:
1. Mouse EGF, 201 (Toyobo Co., Ltd., Japan).
2. 3T3/EGFRc7.

Remaining Materials and Reagents and Procedure, as above.

EGF-Induced Her-2-Driven BrdU Incorporation Assay

Materials and Reagents:
1. Mouse EGF, 201 (Toyobo Co., Ltd., Japan).
2. 3T3/EGFr/Her2/EGFr (EGFr with a Her-2 kinase domain).

Remaining Materials and Reagents and Procedure, as above.

EGF-Induced Her-4-driven BrdU Incorporation Assay

Materials and Reagents:
1. Mouse EGF, 201 (Toyobo Co., Ltd., Japan).
2. 3T3/EGFr/Her4/EGFr (EGFr with a Her-4 kinase domain).

Remaining Materials and Reagents and Procedure, as above.

PDGF-Induced BrdU Incorporation Assay

Materials and Reagents:
1. Human PDGF B/B (Boehringer Mannheim, Germany).
2. 3T3/EGFRc7.

Remaining Materials and Reagents and Procedure, as above.

FGF-Induced BrdU Incorporation Assay

Materials and Reagents:
1. Human FGF2/bFGF (Gibco BRL, USA).
2. 3T3c7/EGFr

Remaining Materials and Reagents and Procedure, as above.

HGF-Induced BrdU Incorporation Assay

Materials and Reagents:
1. Recombinant human HGF (Cat. No. 249-HG, R&D Systems, Inc. USA).
2. BxPC-3 cells (ATCC CRL-1687).

Remaining Materials and Reagents, as above.

141

Procedure:

1. Cells are seeded at 9000 cells/well in RPMI 10% FBS in a 96 well plate. Cells are incubated overnight at 37° C. in 5% $CO_2$.
2. After 24 hours, the cells are washed with PBS, and then are serum starved in 100 μl serum-free medium (RPMI with 0.1% BSA) for 24 hours.
3. On day 3, 25 μl containing ligand (prepared at 1 μg/ml in RPMI with 0.1% BSA; final HGF conc. is 200 ng/ml) and test compounds are added to the cells. The negative control wells receive 25 μl serum-free RPMI with 0.1% BSA only; the positive control cells receive the ligand (HGF) but no test compound. Test compounds are prepared at 5 times their final concentration in serum-free RPMI with ligand in a 96 well plate, and serially diluted to give 7 test concentrations. Typically, the highest final concentration of test compound is 100 μM, and 1:3 dilutions are used (i.e. final test compound concentration range is 0.137–100 μM).
4. After 18 hours of ligand activation, 12.5 μl of diluted BrdU labeling reagent (1:100 in RPMI, 0.1% BSA) is added to each well and the cells are incubated with BrdU (final concentration is 10 μM) for 1 hour.
5. Same as General Procedure.
6. Same as General Procedure.
7. The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.
8. Same as General Procedure.
9. Same as General Procedure.
10. Same as General Procedure.

HUV-EC-C Assay

This assay is used to measure a compound's activity against PDGF-R, FGF-R, VEGF, aFGF or Flk-1/KDR, all of which are naturally expressed by HUV-EC cells.

Day 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 $cm^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of $0.8–1.0 \times 10^5$ cells/ml.

142

3. Add cells to 96-well flat-bottom plates at 100 μl/well or $0.8–1.0 \times 10^4$ cells/well, incubate ~24 h at 37° C., 5% $CO_2$.

Day 1

1. Make up two-fold test compound titrations in separate 96-well plates, generally 50 μM on down to 0 μM. Use the same assay medium as mentioned in day 0, step 2 above. Titrations are made by adding 90 μl/well of test compound at 200 μM (4× the final well concentration) to the top well of a particular plate column. Since the stock test compound is usually 20 mM in DMSO, the 200 μM drug concentration contains 2% DMSO.

A diluent made up to 2% DMSO in assay medium (F12K+ 0.5% fetal bovine serum) is used as diluent for the test compound titrations in order to dilute the test compound but keep the DMSO concentration constant. Add this diluent to the remaining wells in the column at 60 μl/well. Take 60 μl from the 120 μl of 200 μM test compound dilution in the top well of the column and mix with the 60 μl in the second well of the column. Take 60 μl from this well and mix with the 60 μl in the third well of the column, and so on until two-fold titrations are completed. When the next-to-the-last well is mixed, take 60 μl of the 120 μl in this well and discard it. Leave the last well with 60 μl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 μl/well of the test compound dilutions to the 96-well assay plates containing the $0.8–1.0 \times 10^4$ cells/100 μl/well of the HUV-EC-C cells from day 0 and incubate ~2 h at 37° C., 5% $CO_2$.
3. In triplicate, add 50 μl/well of 80 μg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 μl test compound dilution, 50 μl growth factor or media, and 100 μl cells, which calculates to 200 μl/well total. Thus the 4× concentrations of test compound and growth factors become 1× once everything has been added to the wells.

Day 2

1. Add $^3$H-thymidine (Amersham, catalogue no. TRK-686) at 1 μCi/well (10 μl/well of 100 μCi/ml solution made up in RPMI media+10% heat-inactivated fetal bovine serum) and incubate ~24 h at 37° C., 5% $CO_2$. RPMI is obtained from Gibco BRL, catalogue no. 11875-051.

Day 3

1. Freeze plates overnight at −20° C.

Day 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models

Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, Acta Pathol. Microbial. Scand. 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include HT-29 (ATCC # HTB-38), C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

9–12 week old female athymic mice (BALB/c, nu/nu) are obtained from Charles River Laboratories (Wilmington, Mass.). All animals are maintained under clean-room conditions in sterile cages (Lab Products, Maywood, N.J.) with Sani Chips (Montville, N.J.). They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×$10^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 µL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject $10^7$ tumor cells in a volume of 100 µl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

MTT Proliferation Assay

MO7E cells are serum starved and pre-treated with compound as described for the phosphorylation experiments. Cells areplated @ 4×$10^5$ cells/well in a 96 well dish, in 100 µl RPMI+10% serum. rh-SCF (100 ng/mL) is added and the plate is incubated for 48 hours. After 48 hours, 10 µl of 5 mg/ml MTT [3-(4,5-dimethythiazol-2-yl)-2,5-diphenyl tetrazolium bromide) is added and allowed to incubate for 4 hours. Acid isopropanol (100 µl of 0.04N HCl in isopropanol) is added and the optical density was measured at a wavelength of 550 nm.

Apoptosis Assay

MO7E cells are incubated +/− SCF and +/− compound in 10% FBS with rh-GM-CSF (10 ng/mL) and rh-IL-3 (10 ng/mL). Samples are assayed at 24 and 48 hours. To measure activated caspase-3, samples are washed with PBS and permeabilized with ice-cold 70% ethanol. The cells are then stained with PE-conjugated polyclonal rabbit anti-active caspase-3 and analyzed by FACS. To measure cleaved PARP, samples are lysed and analyzed by western blotting with an anti-PARP antibody.

GST-Kinase Bioassay with Poly-Glutamic Acid Tyrosine Substrate Phosphorylation Assay:

The method below describes the bioassay for use in the screening for inhibitors of GST-Abl kinase activity. The assay can be modified to screen for inhibitors of GST-Lyn, GST-LCK, and GST-DDR1 kinase activity.

GST-Abl Bioassay

1. Coat plates overnight at 4° C. or 2 hours at room temperature with 100 µl of 20 µg/ml polyGlu.Tyr (Sigma #P0275) in PBS.
2. Remove liquid from wells by inverting plate; wash 1× with TBS-TWEEN; pat the plate on a paper towel to remove excess liquid.
3. Block with 150 µl of 1% BSA in TBS for 30 minutes at RT.
4. Wash plates once with TBS-TWEEN, leave to soak with 150 µl 50 mM HEPES pH7.4.

5. Plate test compounds (2 mM in DMSO) 5 µl/well in a Costar plate ready for dilution with dH$_2$O and plating to reaction plates.
6. Add 120 µl of distilled water to the 5 µl of each compound in the dilution plate and carry out the required serial dilution, then add 25 µl/well of this to the reaction plate. This will ultimately give a final top concentration of 20 µM in the reaction if the original was 2 mM in DMSO.
7. Dilute GST-Abl 1:10,000 in 2× kinase buffer.
For 5 plates prepare 25 mL solution as follows:
  25 mL 2× kinase buffer.
  50 µl 1.0M DTT (stored frozen at −20° C.).
  2.5 µl GST-Abl (stored frozen at −80° C.).
Add 50 µl to each well.
8. Add 25µl 0.5M EDTA to negative control wells.
9. Dilute 10 mM ATP with H$_2$O.
For 5 plates prepare 12.5 mL as follows:
  10 µl 10 mM ATP.
  12.49 mL distilled water.
Add 25 µl to each well. (The final ATP concentration is 2 µM).
10. Incubate at RT for 5 minutes, on plate shaker. Terminate reaction by addition of 25µl of 0.5mM EDTA.
11. Wash x4 with TBS-TWEEN. (Wash#1 program).
12. Add 100 µl PY99 HRP (1:5,000 in TBS-TWEEN) and incubate at RT for one hour on plate shaker.
13. Wash plates x4 with TBS-TWEEN (Wash#1 program) and once with distilled water.
14. Develop plate using 100 µl Moss stable ABTS and stop using 20□1 of 10%SDS/well.

GST-Lyn Bioassay

Assay conditions for GST-Lyn are the same as those described above for Abl except that GST-Lyn is used in place of GST-Abl. The final ATP concentration used in the assay is adjusted to 4.0 micromolar.

GST-LCK Bioassay

Assay conditions for GST-LCK are same as those described above for Abl except that poly Lysine-Tyrosine is substituted for poly Glutamic acid-Tyrosine as substrate AND GST-LCK is used in place of GST-Abl. The final ATP concentration used in the assay is adjusted to 2.0 micromolar.

GST-DDR1 Bioassay

Assays conditions for GST-DDR1 are the same as those describing GST-Abl bioassay except that GST-Abl is replaced with GST-DDR1. The final ATP concentration is adjusted to 600 micromolar.

ZC1 Scintillation Proximity Assay

The Scintillation Proximity assay (SPA) is used to analyze the protein serine/threonine kinase activity of ZC1 in vitro to screen for inhibitors of ZC1 in a homogeneous assay. The assay described below is amenable for high throughput screening of ZC1 Inhibitors.

Materials and Solutions:
1. Wallac 96-well polyethylene terephthalate (flexi) plates (Wallac Catalog #1450-401)
2. NEN Easy-Tide [γ$^{33}$P] ATP (NEN Catalog #NEG602H)
3. Amersham streptavidin coated polyvinyltoluene SPA beads (Amersham catalog #NIF 107)—Reconstitute beads in PBS without magnesium or calcium, at 50 mg/mL. Store reconstituted beads at 4° C. (To achieve optimal counts, it is important that excess streptavidin SPA bead should be present in order to bind all of the biotinylated molecules in the assay.) Activated ZC1 enzyme purified from Sf9 cells—Final concentration of 300 ng/well.
4. Peptide substrate #902B (biotin-KRTLRRKRTLR-RKRTLRR)—Final concentration of 0.5 µM/well (2×Km)

Procedure:
1. Prepare solutions of inhibitors at 5× the desired final concentration in 5% DMSO. Add 10 µL to each well of the flexiplate. For positive and negative controls, add 10 µL 5% DMSO.
2. Prepare ATP mix as shown above (2.1 ml of ATP mix is sufficient for one assay plate). Add 20 µL to all wells.
3. Add 20 µL of 5M EDTA to negative control wells.
4. Prepare the enzyme solution in 2.5× kinase buffer (50 mM HEPES pH 7.4, 12.5 mM MnCl$_2$, 500 mM NaCl, and 1 mM DTT. The final enzyme concentration will be 0.30 µg/well (For example, given a 0.5 mg/mL stock, add 302 µL ZC1 enzyme to 10 mL Kinase Buffer.) Add 20 µL per well to start the reaction.
5. Allow kinase reaction to proceed at room temperature for 60 minutes.
6. To each well, add 200 µL of a stop solution containing 0.05 mM ATP, 5 mM EDTA, 0.1% Triton x-100, and 5 mg per ml Amersham streptavidin-coated polyvinyltoluene SPA beads (Cat # NIF 1077) in PBS. Incubate for 15 minutes.
7. Spin plate at 2300 rpm for 15 min.
8. Count plate on Trilux reader using SPA flexiplate protocol (including quench curve).

Additional Assays

Additional assays which may be used to evaluate the compounds of this invention include, without limitation, a bio-flk-1 assay, an EGF receptor-HER2 chimeric receptor assay in whole cells and an assay measuring the phosphorylation function of raf. The protocols for each of these assays may be found in U.S. Pat. No. 6,130,238 to Peng et al. which is incorporated by reference, including any drawings, herein.

Measurement of Cell Toxicity

Therapeutic compounds should be more potent in inhibiting kinase activity than in exerting a cytotoxic effect. A measure of the effectiveness and cell toxicity of a compound can be obtained by determining the therapeutic index, i.e., IC$_{50}$/LD$_{50}$. IC$_{50}$, the dose required to achieve 50% inhibition, can be measured using standard techniques such as those described herein. LD$_{50}$, the dosage which results in 50% toxicity, can also be measured by standard techniques as well (Mossman, 1983, *J. Immunol. Methods*, 65:55–63), by measuring the amount of LDH released (Korzeniewski and Callewaert, 1983, *J. Immunol. Methods*, 64:313, Decker and Lohmann-Matthes, 1988, *J. Immunol. Methods*, 115: 61), or by measuring the lethal dose in animal models. Compounds with a large therapeutic index are preferred. The therapeutic index should be greater than 2, preferably at least 10, more preferably at least 50.

Plasma Stability Test:

The plasma stability of the compounds of the preferred embodiments of the present invention is conducted by spiking the compound in blank plasma at 37° C. The compound concentration is approximately 1 µg/mL or 10 µg/mL. 100 µL of plasma sample is taken at different time points and immediately added to acidified acetonitrile, folllowed by filtration and dilution in a mixture containing 0.7% formic acid in 50% acetonitrile in water. The amount of remaining compound is analyzed by LC/MS/MS.

This application claims priority to and incorporates by reference, U.S. Ser. Nos. 60/449,552 (Feb. 25, 2003), 60/406,334 (Aug. 28, 2002) and 60/402,547 (Aug. 12, 2002).

What is claimed is:

1. A compound of the formula I

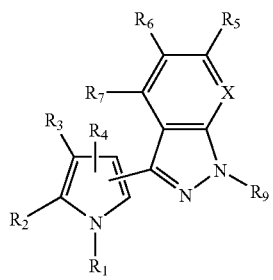

(I)

wherein X is N;

$R_1$ and $R_9$ are independently selected from the group consisting of H, alkyl, aryl, arylsulfonyl, alkylsulfonyl, and a prodrug group selected from the group consisting of C(O)NRR', C(O)OR', SO$_2$R and C(O)R';

$R_2$ and $R_4$ are independently selected from the group consisting of H, alkyl, aryl, heteroaryl, halogen, cyano, NO$_2$, NHR', C(O)R, NHC(O)R, NHSO$_2$R', (CH$_2$)$_2$SO$_2$ (CH$_2$)$_n$R, (CH$_2$)$_m$SO$_2$N(R)(CH$_2$)$_n$R', C(O)NHNRR', (CH$_2$)$_n$CO$_2$R, (CH$_2$)$_n$C(O)NRR', NHC(O)NHR, (CH$_2$)$_n$ NRR', (CH$_2$)$_n$OR', and (CH$_2$)$_n$OC(O)R' wherein said alkyl, aryl or heteroaryl may be further substituted with halogen, NO$_2$, hydroxy, carboxylic acid, amino or a heteroalicyclic;

$R_3$ is selected from the group consisting of halogen, NHC(O)R, (CH$_2$)$_m$SO$_2$(CH$_2$)$_n$R, (CH$_2$)SO$_2$N(R) (CH$_2$)$_n$ R', (CH$_2$)$_n$CO$_2$R and (CH$_2$)$_n$C(O)NRR';

$R_5$, $R_6$, $R_7$ and $R_8$ are independently selected from the group consisting of H, alkyl, alkoxy, aryl, aryloxy, heteroaryl, halogen, cyano, NO$_2$, NRR', C(O)R, NHC (O)R, (CH$_2$)$_m$SO$_2$(CH$_2$)$_n$R, (CH$_2$)$_n$SO$_2$NRR', NHSO$_2$R', (CH$_2$)$_n$CO$_2$R', (CH$_2$)$_n$C(O)NRR', NHC(O) NHR, (CH$_2$)$_n$NRR', (CH$_2$)$_n$OR' trihalomethyl and (CH$_2$)$_n$OC(O)R';

n is 0–3;

m is 0–3;

R and R' are independently selected from the group consisting of H, alkyl, heteroaryl, and aryl, wherein alkyl or aryl may be further substituted with halogen, NO$_2$, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, a heteroalicyclic ring, alkyl, alkoxy, —CZ$_3$, —OCZ$_3$, aryloxy, C(O)NH$_2$ or heteroaryl;

R" is H, alkyl or aryl;

Z is a halogen;

alternatively, R and R', together with the nitrogen to which they are attached, form a 5–7 membered heteroalicyclic ring or a 5–6 membered heteroaryl ring, wherein the heteroalicyclic ring or heteroaryl ring may contain a N, O or S atom in said heteroalicyclic or heteroaryl ring and wherein said heteroalicyclic or heteroaryl ring may be substituted with a moiety selected from the group consisting of alkyl, haloalkyl, alkoxy, hydroxy and halogen;

provided that $R_4$ is bonded to either the 2 or 3 position of the pyrrole ring and the pyrazole ring is bonded to the 2 or 3 position, provided that both $R_4$ and the pyrazole ring are not bonded to the same position; or a pharmaceutically acceptable salt thereof.

2. A compound of Formula I

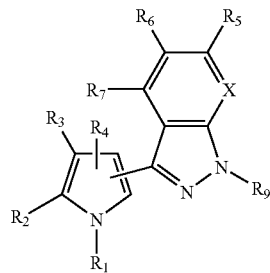

(I)

wherein X is N;

$R_1$ and $R_9$ are independently selected from the group consisting of H, alkyl, aryl, arylsulfonyl, alkylsulfonyl, and a prodrug group selected from the group consisting of C(O)NRR', C(O)OR', SO$_2$R and C(O)R';

$R_2$, $R_3$ and $R_4$ are independently selected from the group consisting of H, alkyl, aryl, heteroaryl, halogen, cyano, NO$_2$, NHR', C(O)R, NHC(O)R, NHSO$_2$R', (CH$_2$)$_m$SO$_2$ (CH$_2$)$_n$R, (CH$_2$)$_m$SO$_2$N(R)(CH$_2$)$_n$R', C(O)NHNRR', (CH$_2$)$_n$CO$_2$R; (CH$_2$)$_n$C(O)NRR', NHC(O)NHR, (CH$_2$)$_n$ NRR', (CH$_2$)$_n$OR', and (CH$_2$)$_n$OC(O)R' wherein said alkyl, aryl or heteroaryl may be further substituted with halogen, NO$_2$, hydroxy, carboxylic acid, amino or a heteroalicyclic;

$R_6$ is selected from the group consisting of NO$_2$, NHC (O)R, (CH$_2$)$_m$SO$_2$(CH$_2$)$_n$R, and trihalomethyl;

$R_5$, $R_7$ and $R_8$ are independently selected from the group consisting of H, alkyl, alkoxy, aryl, aryloxy, heteroaryl, halogen, cyano, NO$_2$, NRR', C(O)R, NHC(O)R, (CH$_2$)$_m$ SO$_2$(CH$_2$)$_n$R, (CH$_2$)$_n$SO$_2$NRR', NHSO$_2$R', (CH$_2$)$_n$CO$_2$R', (CH$_2$)$_n$C(O)NRR', NHC(O)NHR, (CH$_2$)$_n$ NRR', (CH$_2$)$_n$OR' trihalomethyl and (CH$_2$)$_n$OC (O)R';

n is 0–3;

m is 0–3;

R and R' are independently selected from the group consisting of H, alkyl, heteroaryl, and aryl, wherein alkyl or aryl may be further substituted with halogen, NO$_2$, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, heteroalicyclic ring, alkyl, alkoxy, —CZ$_3$, —OCZ$_3$, aryloxy, C(O)NH$_2$ or heteroaryl;

R" is H, alkyl or aryl;

Z is a halogen;

alternatively, R and R', together with the nitrogen to which they are attached, form a 5–7 membered heteroalicyclic ring or a 5–6 membered heteroaryl ring, wherein the heteroalicyclic ring or said heteroaryl ring may contain a N, O or S atom in teroalicyclic or heteroaryl ring and wherein said heteroalicyclic or heteroaryl ring may be substituted with a moiety selected from the group consisting of alkyl, haloalkyl, alkoxy, hydroxy and halogen;

provided that $R_4$ is bonded to either the 2 or 3 position of the pyrrole ring and the pyrazole ring is bonded to the 2 or 3 position, provided that both $R_4$ and the pyrazole ring are not bonded to the same position; or a pharmaceutically acceptable salt thereof.

3. The compound of claim 1, wherein $R_5$ is selected from the group consisting of halogen, amino and heteroalicyclic ring.

4. The compound of claim 3, wherein $R_1$ and $R_9$ are selected from the group consisting of H, alkyl, C(O)OR' and SO$_2$R.

5. The compound of any one of claims 1 or 2 wherein $R_3$ is selected from the group consisting of NHC(O)R, (CH$_2$)$_m$SO$_2$(CH$_2$)$_n$R, (CH$_2$)$_m$SO$_2$N(R)(CH$_2$)$_n$R', (CH$_2$)$_n$CO$_2$R, and (CH$_2$)$_n$C(O)NRR'.

6. The compound of any one of claims 1 or 2, wherein $R_6$ is selected from the group consisting of NHC(O)R and NO2.

7. A compound of Formula II:

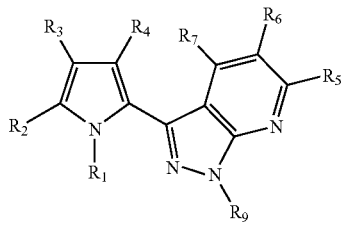

(II)

$R_1$ and $R_9$ are independently selected from the group consisting of H, alkyl, arylsulfonyl, alkylsulfonyl, or a prodrug group selected from the group consisting of C(O)NRR', C(O)OR', SO$_2$R and C(O)R';

$R_2$ and $R_4$ are independently selected from the group consisting of H, alkyl, aryl, heteroaryl, halogen, cyano, NO$_2$, NHR', C(O)R, NHC(O)R, NHSO$_2$R', (CH$_2$)$_m$SO$_2$(CH$_2$)$_n$R, (CH$_2$)$_m$SO$_2$N(R)(CH$_2$)$_n$R', C(O)NHNRR', (CH$_2$)$_n$CO$_2$R, (CH$_2$)$_n$C(O)NRR', NHC(O)NHR, (CH$_2$)$_n$ NRR', (CH$_2$)$_n$OR', or (CH$_2$)$_n$OC(O)R' wherein said alkyl, aryl or heteroaryl may be further substituted with halogen, NO$_2$, hydroxy, carboxylic acid, amino or a heteroalicyclic;

$R_3$ is selected from the group consisting of halogen, NHC(O)R, (CH$_2$)$_m$SO$_2$(CH$_2$)$_n$R, (CH$_2$)$_m$SO$_2$N(R)(CH$_2$)$_n$R', (CH$_2$)$_n$CO$_2$R and (CH$_2$)$_n$C(O)NRR';

$R_5$, $R_6$, $R_7$ and $R_8$ are independently selected from the group consisting of H, alkyl, alkoxy, aryl, aryloxy, heteroaryl, halogen, cyano, NO$_2$, NRR', C(O)R, NHC(O)R, (CH$_2$)$_m$SO$_2$(CH$_2$)$_n$R, (CH$_2$)$_n$SO$_2$NRR', NHSO$_2$R', (CH$_2$)$_n$CO$_2$R', (CH$_2$)$_n$C(O)NRR', NHC(O)NHR, (CH$_2$)$_n$NRR', (CH$_2$)$_n$OR' trihalomethyl and (CH$_2$)$_n$OC(O)R';

n is 0–3;

m is 0–3;

R and R' are independently selected from the group consisting of H, alkyl, heteroaryl, and aryl, wherein alkyl or aryl may be further substituted with halogen, NO$_2$, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, a heteroalicyclic ring, alkyl, alkoxy, —CZ$_3$, —OCZ$_3$, aryloxy, C(O)NH$_2$ or heteroaryl;

R" is H, alkyl or aryl;

Z is a halogen;

alternatively, R and R', together with the nitrogen to which they are attached, form a 5–7 membered heteroalicyclic ring or a 5–6 membered heteroaryl ring, wherein the heteroalicyclic ring or heteroaryl ring may contain a N, O or S atom in said heteroalicyclic or heteroaryl ring and wherein said heteroalicyclic or heteroaryl ring may be substituted with a moiety selected from the group consisting of alkyl, haloalkyl, alkoxy, hydroxy and halogen; or a pharmaceutically acceptable salt thereof.

8. A compound selected from the group consisting of:

3-(3,5-Dimethyl-1H-pyrrol-2-yl)-1H-pyrazolo[3,4-b]pyridine;

3-(1H-Pyrrol-2-yl)-1H-pyrazolo[3,4-b]pyridine;

3-(5-Morpholin-4-ylmethyl-1H-pyrrol-2-yl)-1H-pyrazolo[3,4-b]pyridine;

3-(4-Bromo-1H-pyrrol-2-yl)-1H-pyrazolo[3,4-b]pyridine;

3-(3-Phenyl-1H-pyrrol-2-yl)-1H-pyrazolo[3,4-b]pyridine;

3-[4-(2,6-Dichloro-phenyl)-1H-pyrrol-2-yl]-1H-pyrazolo[3,4-b]pyridine;

3-[3-(2,6-Dichloro-phenyl)-1H-pyrrol-2-yl]-1H-pyrazolo[3,4-b]pyridine;

(2,6-Difluoro-phenyl)-[5-(1H-pyrazolo[3,4-b]pyridin-3-yl)-1H-pyrrol-3-yl]-methanone;

6-Chloro-3-(1H-pyrrol-2-yl)-1H-pyrazolo[3,4-b]pyridine;

6-Chloro-3-(1H-pyrrol-3-yl)-1H-pyrazolo[3,4-b]pyridine;

5-(1H-Pyrazolo[3,4-b]pyridin-3-yl)-1H-pyrrole-3-carboxylic acid ethyl ester;

5-(1H-Pyrazolo[3,4-b]pyridin-3-yl)-1H-pyrrole-3-carboxylic acid;

5-(1H-Pyrazolo[3,4-b]pyridin-3-yl)-1H-pyrrole-3-carboxylic acid (2-morpholin-4-yl-ethyl)-amide;

5-(1H-Pyrazolo[3,4-b]pyridin-3-yl)-1H-pyrrole-3-carboxylic acid amide;

5-(1H-Pyrazolo[3,4-b]pyridin-3-yl)-1H-pyrrole-3-carboxylic acid benzylamide;

5-(1H-Pyrazolo[3,4-b]pyridin-3-yl)-1H-pyrrole-3-carboxylic acid isobutyl-amide;

5-(1H-Pyrazolo[3,4-b]pyridin-3-yl)-1H-pyrrole-3-sulfonic acid (2-morpholin-4-yl-ethyl)-amide;

5-(1H-Pyrazolo[3,4-b]pyridin-3-yl)-1H-pyrrole-3-sulfonic acid benzylamide;

5-(1H-Pyrazolo[3,4-b]pyridin-3-yl)-1H-pyrrole-3-carboxylic acid carbamoylmethyl-amide;

5-(1H-Pyrazolo[3,4-b]pyridin-3-yl)-1H-pyrrole-3-carboxylic acid phenethyl-amide;

5-(1H-Pyrazolo[3,4-b]pyridin-3-yl)-1H-pyrrole-3-carboxylic acid phenylamide;

5-(1H-Pyrazolo[3,4-b]pyridin-3-yl)-1H-pyrrole-2-carboxylic acid;

5-(1H-Pyrazolo[3,4-b]pyridin-3-yl)-1H-pyrrole-2-carboxylic acid ethyl ester;

5-(1H-Pyrazolo[3,4-b]pyridin-3-yl)-1H-pyrrole-2-carboxylic acid methylamide;

5-(1H-Pyrazolo[3,4-b]pyridin-3-yl)-1H-pyrrole-2-carboxylic acid (3-fluoro-phenyl)-amide;

5-(1H-Pyrazolo[3,4-b]pyridin-3-yl)-1H-pyrrole-2-carboxylic acid ((S)-1-phenyl-ethyl)-amide;

4-(1H-Pyrazolo[3,4-b]pyridin-3-yl)-1H-pyrrole-3-carboxylic acid ethyl ester;

6-Morpholin-4-yl-3-(1H-pyrrol-2-yl)-1H-pyrazolo[3,4-b]pyridine;

6-(4-Methyl-piperazin-1-yl)-3-(1H-pyrrol-2-yl)-1H-pyrazolo[3,4-b]pyridine;

5-(6-Chloro-1H-pyrazolo[3,4-b]pyridin-3-yl)-1H-pyrrole-3-sulfonic acid benzylamide;

5-(1H-Pyrazolo[3,4-b]pyridin-3-yl)-1H-pyrrole-3-sulfonic acid 4-methoxy-benzylamide;
5-(1H-Pyrazolo[3,4-b]pyridin-3-yl)-1H-pyrrole-3-sulfonic acid 2,4-dichloro-benzylamide;
5-(1H-Pyrazolo[3,4-b]pyridin-3-yl)-1H-pyrrole-3-sulfonic acid 4-chloro-benzylamide;
5-(1H-Pyrazolo[3,4-b]pyridin-3-yl)-1H-pyrrole-3-sulfonic acid (biphenyl-4-ylmethyl)-amide;
5-(1H-Pyrazolo[3,4-b]pyridin-3-yl)-1H-pyrrole-3-sulfonic acid 2,6-difluoro-benzylamide;
Benzyl-[3-(1H-pyrrol-2-yl)-1H-pyrazolo[3,4-b]pyridin-6-yl]-amine;
3-(4-Nitro-1H-pyrrol-2-yl)-1H-pyrazolo[3,4-b]pyridine;
5-(1H-Pyrazolo[3,4-b]pyridin-3-yl)-1H-pyrrole-3-sulfonic acid 3-chloro-benzylamide;
5-(1H-Pyrazolo[3,4-b]pyridin-3-yl)-1H-pyrrole-3-sulfonic acid [1-(4-chloro-phenyl)-ethyl]-amide;
5-(1H-Pyrazolo[3,4-b]pyridin-3-yl)-1H-pyrrole-3-sulfonic acid 4-trifluoromethyl-benzylamide;
5-(1H-Pyrazolo[3,4-b]pyridin-3-yl)-1H-pyrrole-2-carboxylic acid hydrazide;
5-(1H-Pyrazolo[3,4-b]pyridin-3-yl)-1H-pyrrole-3-sulfonic acid 4-fluoro-benzylamide;
5-(1H-Pyrazolo[3,4-b]pyridin-3-yl)-1H-pyrrole-3-sulfonic acid 4-dimethylamino-benzylamide;
1-[5-(1H-Pyrazolo[3,4-b]pyridin-3-yl)-1H-pyrrole-3-sulfonyl]-piperidin-3-ol;
3-[4-(4-Chloro-phenylmethanesulfonyl)-1H-pyrrol-2-yl]-1H-pyrazolo[3,4-b]pyridine;
3-[4-(4-Fluoro-phenylmethanesulfonyl)-1H-pyrrol-2-yl]-1H-pyrazolo[3,4-b]pyridine;
3-[4-(4-Trifluoromethoxy-phenylmethanesulfonyl)-1H-pyrrol-2-yl]-1H-pyrazolo[3,4-b]pyridine;
3-[4-(4-Nitro-phenylmethanesulfonyl)-1H-pyrrol-2-yl]-1H-pyrazolo[3,4-b]pyridine;
3-[4-(2-Chloro-phenylmethanesulfonyl)-1H-pyrrol-2-yl]-1H-pyrazolo[3,4-b]pyridine;
3-[4-(3-Chloro-phenylmethanesulfonyl)-1H-pyrrol-2-yl]-1H-pyrazolo[3,4-b]pyridine;
3-[4-(Biphenyl-2-ylmethanesulfonyl)-1H-pyrrol-2-yl]-1H-pyrazolo[3,4-b]pyridine;
3-[4-(3-Trifluoromethoxy-phenylmethanesulfonyl)-1H-pyrrol-2-yl]-1H-pyrazolo[3,4-b]pyridine;
3-[4-(2,6-Difluoro-phenylmethanesulfonyl)-1H-pyrrol-2-yl]-1H-pyrazolo[3,4-b]pyridine;
3-[4-(3,4-Difluoro-phenylmethanesulfonyl)-1H-pyrrol-2-yl]-1H-pyrazolo[3,4-b]pyridine;
3-{4-[3-(4-Fluoro-phenoxy)-phenylmethanesulfonyl]-1H-pyrrol-2-yl}-1H-pyrazolo[3,4-b]pyridine;
3-[4-(Pyridin-4-ylmethanesulfonyl)-1H-pyrrol-2-yl]-1H-pyrazolo[3,4-b]pyridine;
3-[4-(3-Methoxy-phenylmethanesulfonyl)-1H-pyrrol-2-yl]-1H-pyrazolo[3,4-b]pyridine;
3-(4-m-Tolylmethanesulfonyl-1H-pyrrol-2-yl)-1H-pyrazolo[3,4-b]pyridine;
3-[4-(3,5-Difluoro-phenylmethanesulfonyl)-1H-pyrrol-2-yl]-1H-pyrazolo[3,4-b]pyridine;
3-[4-(2,6-Dimethyl-phenylmethanesulfonyl)-1H-pyrrol-2-yl]-1H-pyrazolo[3,4-b]pyridine;
3-[4-(3-Nitro-phenylmethanesulfonyl)-1H-pyrrol-2-yl]-1H-pyrazolo[3,4-b]pyridine;
3-[4-(4-Trifluoromethyl-phenylmethanesulfonyl)-1H-pyrrol-2-yl]-1H-pyrazolo[3,4-b]pyridine;
5-(1H-pyrazolo[3,4-b]pyridin-3-yl)-1H-pyrrole-3-carboxylic acid 4-chlorobenzylamide;
5-(2-phenoxyphenyl)-3-(1H-pyrrol-2-yl)-1H-pyrazolo[3,4-b]pyridine;
5-(4-methoxyphenyl)-3-(1H-pyrrol-2-yl)-1H-pyrazolo[3,4-b]pyridine;
5-phenyl-3-(1H-pyrrol-2-yl)-1H-pyrazolo[3,4-b]pyridine;
5-(3-nitrophenyl)-3-(1H-pyrrol-2-yl)-1H-pyrazolo[3,4-b]pyridine;
5-(4-phenoxyphenyl)-3-(1H-pyrrol-2-yl)-1H-pyrazolo[3,4-b]pyridine;
5-(1,1'-biphenyl-4-yl)-3-(1H-pyrrol-2-yl)-1H-pyrazolo[3,4-b]pyridine;
5-(1,1'-biphenyl-3-yl)-3-(1H-pyrrol-2-yl)-1H-pyrazolo[3,4-b]pyridine;
5-(1,1'-biphenyl-2-yl)-3-(1H-pyrrol-2-yl)-1H-pyrazolo[3,4-b]pyridine;
3-{4-[(3-chloro-4-fluorobenzyl)sulfonyl]-1H-pyrrol-2-yl}-1H-pyrazolo[3,4-b]pyridine;
3-(4-{[3-fluoro-4-(trifluorormethyl)benzyl]sulfonyl}-1H-pyrrol-2-yl)-1H-pyrazolo[3,4-b]pyridine;
5-(3-chloro-4-fluorophenyl)-3-(1H-pyrrol-2-yl)-1H-pyrazolo[3,4-b]pyridine;
5-[2-(benzyloxy)phenyl]-3-(1H-pyrrol-2-yl)-1H-pyrazolo[3,4-b]pyridine;
5-dibenzo[b,d]furan-4-yl-3-(1H-pyrrol-2-yl)-1H-pyrazolo[3,4-b]pyridine;
3-(4-{[(5-chlorothien-2-yl)methyl]sulfonyl}-1H-pyrrol-2-yl)-1H-pyrazolo[3,4-b]pyridine;
3-{4-[(4-phenypiperazin-1-yl)sulfonyl]-1H-pyrro-2-yl}-1H-pyrazo[3,4-b]pyridine;
3-{4-[(4-pyridin-2-ylpiperazin-1-yl)sulfonyl]-1H-pyrrol-2-yl}-1H-pyrazolo[3,4-b]pyridine;
5-[3-(benzyloxy)phenyl]-3-(1H-pyrrol-2-yl)-1H-pyrazolo[3,4-b]pyridine;
5-[4-(benzyloxy)phenyl]-3-(1H-pyrrol-2-yl)-1H-pyrazolo[3,4-b]pyridine;
5-[4-(benzyloxy)phenyl]-3-(1H-pyrrol-2-yl)-1H-pyrazolo[3,4-b]pyridine;
3-{4-[3-chloro-4-(2-morpholin-4-yl-ethoxy)-phenylmethanesulfonyl]-1H-pyrrol-2-yl}-1H-pyrazolo[3,4-b]pyridine;
2-[4-(4-nitro-phenylmethanesulfonyl)-2-(1H-pyrazolo[3,4-b]pyridin-3-yl)-pyrrol-1-yl]-N-(2-morpholin-4-yl-ethyl)-acetamide;
5-(1H-Pyrazolo[3,4-b]pyridin-3-yl)-1H-pyrrole-3-sulfonic acid (4-chloro-benzyl)-(2-diethylamino-ethyl)-amide;
5-(4'-chloro-1,1'-biphenyl-3-yl)-3-(1H-pyrrol-2-yl)-1H-pyrazolo[3,4-b]pyridine;
N-(4-chlorobenzyl)-4,5-dimethyl-2-(1H-pyrazolo[3,4-b]pyridin-3-yl)-1H-pyrrole-3-carboxamide; and 3-{1-(2-morpholin-4-ylethyl)-4-[(4-nitrobenzyl)sulfonyl]-1H-pyrrol-2-yl}-1H-pyrazolo[3,4-]pyridine;

or a pharmaceutically acceptable salt thereof.

9. The compound of claim 2, selected from the group consisting of:

3-(1H-Pyrrol-2-yl)-1H-pyrazolo[3,4-b]pyridine;
3-(4-Bromo-1H-pyrrol-2-yl)-1H-pyrazolo[3,4-b]pyridine;
3-(3-Phenyl-1H-pyrrol-2-yl)-1H-pyrazolo[3,4-b]pyridine;
(2,6-Difluoro-phenyl)-[5-(1H-pyrazolo[3,4-b]pyridin-3-yl)-1H-pyrrol-3-yl]-methanone;
5-(1H-Pyrazolo[3,4-b]pyridin-3-yl)-1H-pyrrole-3-carboxylic acid phenethyl-amide;

5-(1H-Pyrazolo[3,4-b]pyridin-3-yl)-1H-pyrrole-2-carboxylic acid;
5-(1H-Pyrazolo[3,4-b]pyridin-3-yl)-1H-pyrrole-2-carboxylic acid ethyl ester;
5-(1H-Pyrazolo[3,4-b]pyridin-3-yl)-1H-pyrrole-2-carboxylic acid methylamide;
5-(1H-Pyrazolo[3,4-b]pyridin-3-yl)-1H-pyrrole-2-carboxylic acid (3-fluoro-phenyl)-amide; and
5-(1H-Pyrazolo[3,4-b]pyridin-3-yl)-1H-pyrrole-2-carboxylic acid ((S)-1-phenyl-ethyl)-amide; or
a pharmaceutically acceptable salt thereof.

10. A pharmaceutical composition comprising a compound of any one of claims 1, 2, 7, 8, or 9 and a pharmaceutically acceptable carrier or excipient.

11. The compound of claim 2, wherein $R_5$ is selected from the group consisting of halogen, amino and heteroalicyclic ring.

12. The compound of claim 11, wherein $R_1$ and $R_9$ are selected from the group consisting of H, alkyl, C(O)OR' and SO2R.

* * * * *